US012599650B2

(12) United States Patent (10) Patent No.: US 12,599,650 B2

Hu et al. (45) Date of Patent: Apr. 14, 2026

(54) INHIBITION OF SIRP-GAMMA FOR CANCER TREATMENT

(71) Applicant: AMGEN INC., Thousand Oaks, CA (US)

(72) Inventors: Ruozhen Hu, Thousand Oaks, CA (US); Paolo Manzanillo, Thousand Oaks, CA (US); Wenjun Ouyang, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 834 days.

(21) Appl. No.: 17/618,922

(22) PCT Filed: Jun. 23, 2020

(86) PCT No.: PCT/US2020/039079

§ 371 (c)(1),
(2) Date: Dec. 14, 2021

(87) PCT Pub. No.: WO2020/263793

PCT Pub. Date: Dec. 30, 2020

(65) Prior Publication Data

US 2022/0305081 A1 Sep. 29, 2022

Related U.S. Application Data

(60) Provisional application No. 62/865,537, filed on Jun. 24, 2019.

(51) Int. Cl.
| | |
|---|---|
| *A61K 38/17* | (2006.01) |
| *A61K 47/02* | (2006.01) |
| *A61P 35/00* | (2006.01) |

(52) U.S. Cl.
CPC .......... *A61K 38/1774* (2013.01); *A61K 47/02* (2013.01); *A61P 35/00* (2018.01)

(58) Field of Classification Search
CPC .. A61K 38/1774; A61K 47/02; A61K 38/177; A61P 35/00; C07K 2317/76; C07K 16/2803
See application file for complete search history.

(56) References Cited

U.S. PATENT DOCUMENTS

2018/0312587 A1* 11/2018 Van Eenennaam ..... A61P 35/00

FOREIGN PATENT DOCUMENTS

| WO | 2016187226 A1 | 11/2016 | |
|---|---|---|---|
| WO | WO-2018118887 A1 * | 6/2018 | ......... C07K 16/2803 |

OTHER PUBLICATIONS

Barclay, et al., Nature Reviews Immunology, 2006, 6, 459-464 (Year: 2006).*
Brooke, et.al, J Immunol, 2004, 173, 2562-2570 (Year: 2004).*
Sick, et al., British Journal of Pharmacology, 2012, 167, 1415-1430 (Year: 2012).*
Piccio, et al, Blood, 2005, 105, 2421-2427 (Year: 2005).*
Van Beek, etal, J Immunol, 2005, 175, 7781-7787 (Year: 2005).*
Stefanidakis, et al, Blood 2008, 112, 1280-1289 (Year: 2008).*
Rudikoff, et al., PNAS, 1982, 79, p. 1979-1983 (Year: 1982).*
Nettleship, et al, BMC Structural Biology, 2013, 13:13, (Year: 2013).*
Zhang, et al., Brain Res, 2015, 1623, 74-80 (Year: 2015).*
Nettleship, et al, Protein Expression and Purification, 2008, 83-89 (Year: 2008).*
Hatherley, et al., Molecular Cell, 2008, 31, 266-277 (Year: 2008).*
Janeway, et al., Immunobiology: The Immune System in Health and Disease, 5th edition, 2001 (Year: 2001).*
Rudikoff, et al., PNAS, 1982, 79, 1979-1983 (Year: 1982).*
Lescar et al., J Biol Chem, 1995, 270, 18067-18076 (Year: 1995).*
Edwards, et al., J Mol Biol, 2003, 334, 103-118 (Year: 2003).*
Goel, et al., J Immunol, 2004, 173, 7358-7367 (Year: 2004).*
Nettleship, et al. BMC Structural Biology, 2013, 13, 1-8 (Year: 2013).*
Brooke et al.: "Human Lymphocytes Interact Directly with CD47 Through a Novel Member of the Signal Regulatory Protein (SIRP) Family", The Journal of Immunology, American Association of Immunologists, US, vol. 173, No. 4, (2004-01-01), pp. 2562-2570.
PCT/US2020/039079 International Search Report and Written Opinion (2020-09-30), 11 pages.
Piccio Laura et al.: "Adhesion of human T 1-32 cells to antigen-presenting cells through SIRPbeta2-CD47 interaction costimulates T-cell proliferation", Blood, the American Society of Hematology, US, vol. 105, No. 6, Mar. 15, 2005 (2005- 03-15) pp. 2421-2427.
Stefanidakis et al.: "Endothelial CD47 1-32 interaction with SIRP? is required for human T-cell transendothelial migration under shear flow conditions in vitro", BLOOD, vol. 112, No. 4, May 13, 2008 (2008-05-13), pp. 1280-1289.
EPO Examination Report issued to Application No. 20740126.6, dated Sep. 5, 2024.
Santa Cruz Biotechnology Inc .: "SIRP-gamma (LSB2.20): sc-53604", Datasheet.

* cited by examiner

*Primary Examiner* — Michael Szperka
*Assistant Examiner* — Samantha Lake Hopkins
(74) *Attorney, Agent, or Firm* — Melissa E. Karabinis

(57) ABSTRACT

Provided herein are methods of treating a subject with a tumor or cancer. In exemplary embodiments, the method comprises increasing an immune response against the tumor or cancer in the subject or increasing effector activity or reducing suppressive activity of T-cells in the subject. In exemplary embodiments, the method comprises administering to the subject a SIRPγ binder, e.g., SIRPγ inhibitor, in an amount effective to treat the tumor or cancer in the subject.

9 Claims, 16 Drawing Sheets

Specification includes a Sequence Listing.

HCC
SIRPγ Expression

CRC
SIRPγ Expression

Lung Cancer
SIRPγ Expression

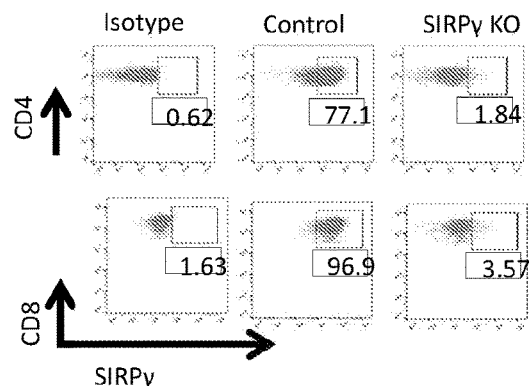
FIGURE 6D
FIGURE 6E
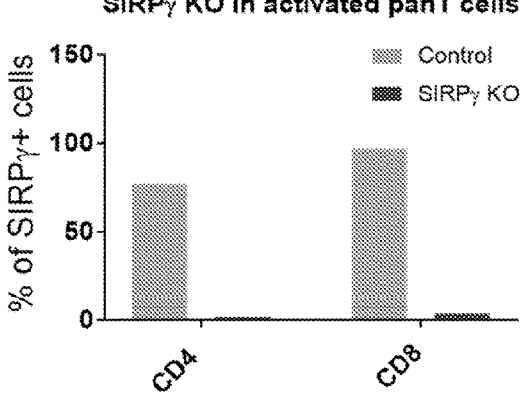
FIGURE 6F
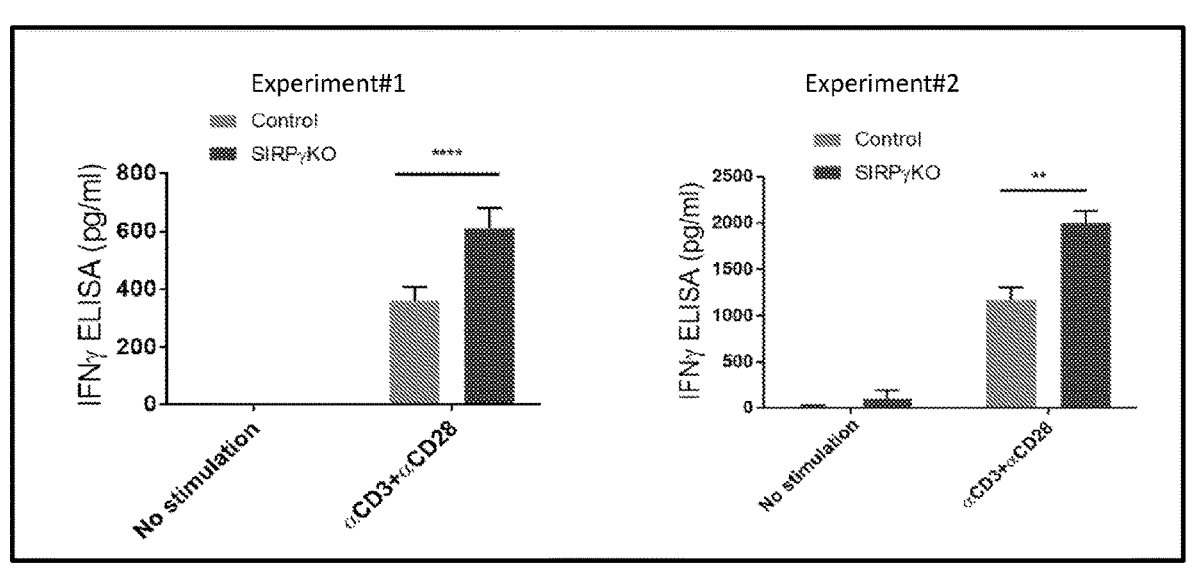

| Cat# | Clone# | Species | Vendor | Binding to SIRPγ | Binding domain on SIRPγ | Blocking interaction between SIRPγ and CD47 | Enhance T cell proliferation and cytokine secretion |
|---|---|---|---|---|---|---|---|
| LS-C484765 | NA | Mouse | LS bio | Yes | ND | No | No |
| LS-C777553 | OX117 | Mouse | LS bio | Yes | D1/D2 of SIRPG | ND | Yes |
| LS-C58159 | OX119 | Mouse | LS bio | Yes | D1 of SIRPG | Yes | No |
| MAB21425 | 4F8C10 | mouse IGG1 | R&D aa29-360 | No | ND | No | No |
| 336602 | LSB2.20 | Mouse | Biolegend | Yes | D1 of SIRPG | Yes | No |
| AF4486 | Polyclonal POLY | SHEEP | R&D 64-364 | Yes | ND | No | No |

ND = not determined

INHIBITION OF SIRP-GAMMA FOR CANCER TREATMENT

CROSS-REFERENCE TO RELATED APPLICATIONS

This application claims priority to U.S. Provisional Patent Application No. 62/865,537, filed on Jun. 24, 2019, the entire contents of which are incorporated herein by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 91,302 bytes ASCII (Text) file named "A-2396-US-PCT_Revised_SequenceListing_ST25," created on Jan. 27, 2025.

BACKGROUND

Immune checkpoint blockade has shown to induce durable immune responses against various cancers. However, the patient responses to immunotherapies, such as anti-PD1/PDL1, are limited to only a small percentage of patients. PD1 is one of many co-inhibitory receptors expressed on T cells that are upregulated during T cell activation and its interaction with PD-L1 limits T cell activation. Although anti-PD-1 sufficiently blocks the inhibitory pathway and rejuvenates T cells inside various tumors, it is possible that many other inhibitory receptors are expressed on T cells. Therefore, exploration and further identification of novel inhibitory receptors on T cells will broaden the targets of immunotherapy and highly advance the efficacy to treat cancer.

SUMMARY

Provided herein for the first time are data demonstrating that SIRPγ is a potential novel inhibitory receptor in human T cells. These data were surprising given previous studies suggesting SIRPγ as a T cell co-stimulatory molecule (Piccio et al., Blood 105(6): 2421-2427 (2005); Leitner et al., Immunol Letters 128(2): 89-97 (2010)). The expression, regulation, and function of SIRPγ were evaluated and it was demonstrated that SIRPγ is mainly expressed on T cells and activated NK cells, and is highly expressed in memory CD8 T cells and tumor infiltrating exhausted T cells. It was also demonstrated herein that overexpression of SIRPγ inhibited CD8 T cell effector cytokine release, while knocked-out expression of SIRPγ (via CRISPR) enhanced the effector states of T cells as measured by T-cell proliferation and T-cell-mediated cytokine production. In addition, overexpression of SIRPγ in human Treg cells lead to enhanced Treg cell suppressive function. Furthermore, the data herein support that blocking the interaction between CD47 and SIRPγ is not a requirement for achieving enhanced T cell proliferation and IFNγ secretion, that the T-cell inhibitory function of SIRPγ may be mediated through a unique epitope of SIRPγ, and that molecules that bind to the interface of D1 and D2 of SIRPγ may be useful in enhancing T cell function.

Without being bound to any particular theory, these data support the use of SIRPγ binders, e.g., SIRPγ inhibitors, for increasing effector activity or reducing suppressive activity of T-cells in a subject ultimately for the treatment of a tumor or cancer in the subject. Accordingly, in one embodiment, the present invention relates to a method of treating a tumor or cancer in a subject comprising administering to the subject an effective amount of a SIRPγ binder, e.g., SIRPγ inhibitor. The present disclosure also provides methods of increasing effector activity or reducing suppressive activity of T-cells in a subject with a tumor or cancer. In exemplary embodiments, the method comprises administering to the subject a SIRPγ binder, e.g., SIRPγ inhibitor, in an amount effective to increase the effector activity or reduce the suppressive activity in the subject. Methods of increasing an immune response against a tumor or cancer in a subject are additionally provided herein. In exemplary embodiments, the method comprises administering to the subject a SIRPγ binder, e.g., SIRPγ inhibitor, in an amount effective to increase an immune response against a tumor or cancer. In various aspects, the subject has hepatocellular carcinoma (HCC), colorectal cancer (CRC), lung cancer, or breast cancer, optionally, wherein the subject has non-small-cell lung cancer (NSCLC).

In various instances, the SIRPγ binder binds to Immunoglobulin (Ig) Domain 1 (D1) of SIRPγ. In various aspects, the SIRPγ binder binds to D1 and Ig Domain 2 (D2) of SIRPγ. In exemplary aspects, the SIRPγ binder binds to both D1 and D2, optionally at the interface between D1 and D2. In exemplary instances, the SIRPγ binder binds to the epitope to which SIRPγ monoclonal antibody OX117 binds, optionally, wherein the SIRPγ binder competes with a reference antibody known to bind to SIRPγ (e.g., OX117) for binding to SIRPγ. The SIRPγ binder in various instances binds to SIRPγ with the same or higher affinity as OX117, optionally, wherein the SIRPγ binder is OX117, or an antigen binding fragment thereof. The SIRPγ binder in various aspects forms hydrogen bonds with one or more of amino acid residues Q8, E10, G109, K11, L12, and D149 of SIRPγ. The SIRPγ binder causes a conformational change of SIRPγ, upon binding to SIRPγ in some aspects. In various instances, the SIRPγ binder simultaneously binds to two SIRPγ molecules or promotes SIRPγ dimerization. Optionally, the SIRPγ binder binds to an epitope which does not overlap with the CD47 binding site. In various aspects, the SIRPγ binder is an antigen-binding protein which binds SIRPγ. Optionally, the antigen-binding protein is an antibody, an antigen-binding antibody fragment, or an antibody protein product. In some aspects, the antigen-binding protein binds at an epitope within the CD47 binding site of SIRPγ.

In various instances of the presently disclosed methods, the SIRPγ binder is a SIRPγ inhibitor. In some aspects, the SIRPγ inhibitor reduces expression of SIRPγ in cells of the subject, optionally, wherein the SIRPγ inhibitor reduces cell surface expression of SIRPγ on T-cells of the subject. Optionally, the T cells are effector T-cells of the subject. In various instances, the SIRPγ inhibitor reduces a binding interaction between SIRPγ and a SIRPγ binding partner, optionally, CD47.

In exemplary aspects of the presently disclosed methods of increasing effector activity or reducing suppressive activity of T-cells in a subject with a tumor or cancer, the T-cells are located within a tumor or a tumor microenvironment. In various instances, the T-cells are tumor-infiltrating T-cells. In some aspects, the T-cells are T regulatory cells (Tregs). In exemplary instances, the T-cells are exhausted T-cells, optionally, exhausted CD8+ T-cells. In exemplary instances, the T-cells are memory cells, optionally, CD8+ memory cells or CD4+ central memory cells.

In exemplary aspects of the presently disclosed methods of increasing an immune response against a tumor or cancer in a subject, the immune-response is mediated by T-cells. In various aspects, the T-cells are located within a tumor or a tumor microenvironment. In various instances, the T-cells are tumor-infiltrating T-cells. In some aspects, the T-cells are T regulatory cells (Tregs). In exemplary instances, the T-cells are exhausted T-cells, optionally, exhausted CD8+ T-cells. In exemplary instances, the T-cells are memory cells, optionally, CD8+ memory cells or CD4+ central memory cells.

The present disclosure additionally provides methods of treating a subject with a tumor or cancer. In exemplary embodiments, the method comprises increasing an immune response against the tumor or cancer in the subject in accordance with any one of the presently disclosed methods of increasing an immune response against a tumor or cancer in a subject. In exemplary embodiments, the method comprises increasing effector activity or reducing suppressive activity of T-cells in the subject in accordance with any one of the presently disclosed methods of increasing effector activity or reducing suppressive activity of T-cells in a subject with a tumor or cancer.

Additional embodiments and aspects of the presently disclosed pharmaceutical compositions and methods are provided below.

BRIEF DESCRIPTION OF THE DRAWINGS

FIG. 1A is a series of FACS plots showing antibody against SIRPγ specifically detected SIRPγ overexpressed on 293T cells. FIG. 1B is a series of FACS plots showing SIRPγ expression on different types of cells from human peripheral blood mononuclear cells (PBMCs). FIG. 1C shows that SIRPγ expression level on T cells is not changed by TCR stimulation.

FIG. 2A is a series of FACS plots showing expression in different subsets of T cells. CD8+ memory T cells have higher SIRPγ expression than CD8+ effector T cells in human PBMC samples. FIG. 2B is a quantification of mean fluorescence intensity (MFI) of SIRPγ expression in different subsets of T cells from 4 different healthy donor PBMCs. Significance is denoted as *p≤0.0002, p≤0.0021, *p≤0.0332, and ns p>0.05 using a paired t test. Error bars represent±SEM.

FIG. 3A is a graph comparing the expression of SIRPγ on different subsets of tumor infiltrated T cells from HCC samples. FIG. 3B is a graph comparing the expression of SIRPγ on different subsets of tumor infiltrated T cells from CRC samples. FIG. 3C is a graph comparing the expression of SIRPγ on different subsets of tumor infiltrated T cells from lung cancer samples. SIRPγ exhibited a highly specific expression pattern in both tumor Tregs (CD4-CTLA4) and exhausted CD8 T cells (CD8-LAYN), marked with star.

FIG. 4 is a series of FACS plots showing expression of SIRPγ on in vitro restimulated exhausted T cells and conventional T cells from three different healthy donors.

FIG. 5A is a schematic diagram showing the experimental flow of SIRPγ overexpression and T cell restimulation. PanT cells were isolated from human PBMCs and activated by αCD3/CD28 Dynabeads for 3 days. Activated T cells were infected with retrovirus (RV) to overexpress SIRPγ (RV-SIRPγ) on T cells or infected with an RV vector without SIRPγ coding sequence as a control (RV-Vec). 5 days post spin-infection, GFP+ CD4 or CD8 T cells were FACS sorted and rested 2 days with human IL2. Rested T cells were then restimulated with plate bounded αCD3 and soluble CD28 antibodies for 24 hours. Cell supernatant was collected for ELISA analysis. FIG. 5B is a series of flow cytometry plots showing human SIRPγ expression on both CD4+ T cells and CD8+ T cells. 3 days post spin-infection, cells were stained with human SIRPγ antibody. FIG. 5C is an ELISA of human IFNγ in the cell supernatant. Significance is denoted as **p≤0.00001, *p≤0.0002, **p≤0.0021, *p≤0.0332, and ns p>0.05 using two-way ANOVA test from Graphpad Prism. Error bars represent±SEM. Data represent at least five independent experiments. FIG. 5D is a paired T test of ELISA of human IFNγ in the cell supernatant from five independent experiments. * denotes a p value of <0.05 using a paired T test.

FIGS. 6A-6F demonstrate that SIRPγ knockdown on T cells enhanced IFNγ secretion. FIG. 6A is a schematic diagram showing the experimental flow of SIRPγ knockdown and T cell restimulation. PanT cells were isolated from human PBMCs and activated by αCD3/CD28 Dynabeads for 2 days. Activated T cells were transfected with CRISPR gRNAs (guide RNAs) that targeted to SIRPγ genomic region to knockdown SIRPγ expression (SIRPγ KO) on T cells or transfected with a control. 3 days post transfection, T cells were activated with αCD3/CD28 for 24 hours before FACS sort. SIRPγ-CD4 or CD8 T cells were FACS sorted and rested 2 days with human IL2. Rested T cells were then restimulated with plate bounded αCD3 and soluble CD28 antibodies for 24 hours. Cell supernatant was collected for ELISA analysis. FIG. 6B are gel analyses of PCR product amplified from targeted genomic region. The arrow indicates the deletion on the gRNA targeted genomic region. FIG. 6C are qPCR analyses of expression of SIRPγ after knockout. Significance is denoted as **p≤0.0001, *p≤0.0002, **p≤0.0021, *p≤0.0332, and ns p>0.05 using unpaired t test from Graphpad Prism. Error bars represent±SEM. FIG. 6D is a series of flow cytometry plots showing human SIRPγ expression on both CD4+ T cells and CD8+ T cells after CRISPR knockdown. 4 days post spin-infection, cells were stained with human SIRPγ antibody. FIG. 6E is a quantification of percentage of SIRPγ+ cells in total CD4 or CD8 T cells after CRISPR knockout. FIG. 6F is an ELISA of human IFNγ in the cell supernatant from two independent experiments. Significance is denoted as **p≤0.0001, *p≤0.0002, **p≤0.0021, *p≤0.0332, and ns p>0.05 using two-way ANOVA test from Graphpad Prism. Error bars represent±SEM.

FIG. 7A is a series of FACS plots and histogram showing expression of SIRPγ on tumor infiltrated lymphocytes from non-small-cell lung cancer tissues. FIG. 7B is a schematic diagram showing the experimental flow of SIRPγ overexpression and Treg cells suppression assay. Tregs cells were FACS sorted from panT cells isolated from human PBMCs and activated by αCD3/CD28 Dynabeads for 2 days. Activated Treg cells were transfected with retrovirus to overexpress SIRPγ (RV-SIRPγ) on Treg cells or infected with an RV vector without SIRPγ coding sequence as a control (RV-Vec). 5 days post spin-infection, GFP+ Treg cells were FACS sorted and rested overnight with human IL2 (200 U/ml) before adding to the suppression assay. On the day of setting up the suppression assay, responder CD4 T cells were isolated from a different healthy donor PBMCs and labelled with Cell- Trace Violet (CTV). Rested Treg cells were mixed with CTV labelled responder CD4 T cells at different ratios. Allogenic DCs were added and CD4 T cells proliferation was measured by CTV dilution. FIG. 7C is a series of flow cytometry plots showing human SIRPγ expression on Treg cells after retrovirus spin infection. 5 days post spin-infection, cells were stained with human SIRPγ antibody. FIG. 7D is a series of flow cytometry plots showing human FOXP3 expression on FACS sorted control or SIRPγ overexpression Treg cells. FIG. 7E is a series of flow cytometry plots showing CTV dilution on T cells that mixed with either control and SIRPγ overexpression Tregs. FIG. 7F is a graph showing the percentage of cell proliferation at different ratios of Treg vs responder cells. * denotes a p value of <0.05 using a Student's t test. Error bars represent±SEM.

FIG. 8A is a series of FACS plots showing expression of SIRPγ (left plot) and CD47 (right plot) on Jurkat T cells after CRISPR knockout of SIRPγ (SIRPγ KO), CD47 (CD47 KO) or both SIRPγ and CD47 (DKO). The plot using an isotype matched control antibody (Isotype) or non-transfected control cells (NT control) are shown in each panel. FIG. 8B shows binding analyses of SIRPγ-Fc and SIRPα-Fc proteins on Jurkat T cells. All Fc fusion proteins were added at 5 μg/ml. Binding of fusion proteins to cells was detected by flow cytometry using a PE conjugated anti-human IgG-Fc. FIG. 8C shows antagonist activity study of anti-SIRPγ antibodies (LSB2.20 and OX119) on SIRPγ-Fc binding on Jurkat T cells. All IgG-Fc proteins were added at 5 μg/ml and all antibodies were added at 10 μg/ml. An IgG antibody (mIgG) was used as a control. Binding of fusion proteins to cells was detected by flow cytometry using a PE conjugated anti-human IgG-Fc. FIG. 8D is a graph showing counts per minute (CPM) of human panT cells isolated from PBMCs from healthy donors stimulated with allogeneic dendritic cells (DCs) at a 10 T cell: 1 DC ratio for 7 days. Antibodies were added at day 0 of the culture at 10 μg/ml. T cell proliferation was measured by standard 3H-thymidine incorporation assay. FIG. 8E is a graph showing CPM of control T cells, SIRPγ knockout or CD47 knockout panT cells stimulated with allogeneic dendritic cells (DCs) at a 10 T cell: 1 DC ratio for 7 days. Antibodies were added at day 0 of the culture at 10 μg/ml. T cell proliferation was measured by standard 3H-thymidine incorporation assay. FIG. 8F is human panT cells or CD8 T cells isolated from PBMCs from healthy donors were stimulated with different concentrations of plate bounded anti-CD3 for 3 days. Antibodies against SIRPγ or CD47 were added at day 0 of the culture at 10 μg/ml. T cell proliferation was measured by standard 3H-thymidine incorporation assay.

FIGS. 9A-9E demonstrate that SIRPγ antibody clone OX117, which binds to a specific epitope of SIRPγ, enhances T cell proliferation and cytokine secretion. FIG. 9A is a series of FACS plots showing binding of SIRPγ antibodies on parental Jurkat T cells and Jurkat T cells that overexpress SIRPγ. FIG. 9B shows only antibody OX117 alters the binding of SIRPγ-Fc proteins on Jurkat T cells. Jurkat T cells were pre-treated with SIRPγ antibodies at 10 μg/ml. SIRPγ-Fc proteins were added at 10 μg/ml. Binding of fusion proteins to cells was detected by flow cytometry using a PE conjugated anti-human IgG-Fc. FIGS. 9C and 9D show specific anti-SIRPγ antibody clone OX117 has the strongest antagonist activity on human panT cell in promoting proliferation and cytokine production. Plates were coated with SIRPγ antibodies at 10 μg/ml. Human panT cells isolated from PBMCs from healthy donors were stimulated with IMMUNOCULT™ CD3/CD28 T cell activator along with plate bounded SIRPγ antibodies for 3 days. In FIG. 9C, T cell proliferation was measured by standard 3H-thymidine incorporation assay. FIG. 9D is an CBA analyses of human IFNγ in the cell supernatant from human panT cells stimulated for 48 hrs. FIG. 9E is the overview of the binding epitopes between SIRPγ: FabOX117 and between SIRPα: CD47 complexes, showing that CD47 and FabOX117 bind to different residues on SIRPγ (Nettleship et al., BMC Structural Biology 13: 13 (2013)).

FIG. 10 provides a table summarizing the commercial SIRPγ antibodies properties and their functions on T cells.

DETAILED DESCRIPTION

SIRPγ, SIRPγ Binders, and SIRPγ Inhibitors

Figure 1A:
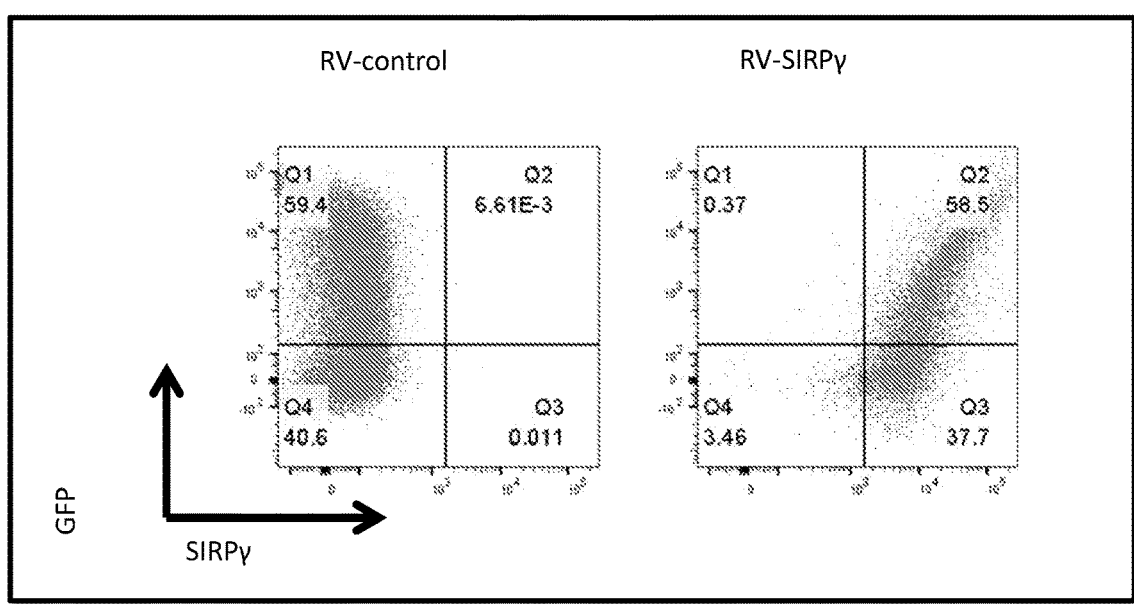
FIGS. 1A-1C demonstrate that SIRPγ is expressed on human T cells and NKT cells.

Signal regulatory protein gamma (SIRPγ or SIRPG)—also known as, CD172g, SIRPB2, SIRP-B2, and bA77C3.1—is a member of the signal-regulatory protein (SIRP) family and also belongs to the immunoglobulin (Ig) superfamily. Like other members of the SIRP family, SIRPγ, has three Type I transmembrane glycoproteins, each comprising three Ig-like domains that make up an extracellular region, a single transmembrane domain, and a short cytoplasmic domain. Unlike other members of SIRP receptor family, SIRPγ lacks cytoplasmic immunoreceptor tyrosine based inhibitory motifs (ITIMs) to recruit the downstream signaling molecules to mediate cell signaling. SIRPγ functions in the negative regulation of receptor tyrosine kinase-coupled signaling processes and integrin-independent adhesion of lymphocytes to antigen-presenting cells. SIRPγ is highly expressed in human blood, thymus and splenic tissue. Within human PBMCs, SIRPγ is mainly expressed on T cells and activated natural killer (NK) cells. Additionally, several recent studies on RNAseq profiling of tumor and adjacent tissue sho wed that SIRPγ is highly expressed on T cells isolated from various tumors. Like SIRPα, SIRPγ binds to CD47, though with lower affinity than SIRPα (Brooke et al., J Immunol 173(4): 2562-2570 (2004)). SIRPγ and its role in the immune system is reviewed in van Beek et al., J Immunol 175(12): 7781-7787 (2005). The crystal structure of SIRPγ is described in Nettleship et al., BMC Structural Biology 13: 13 (2013).

The SIRPγ gene is a polymorphic gene and is found on human chromosome 20 (arm p13) and comprises 8 exons. Several SIRPγ variants have been described in human population and the protein sequences of such SIRPγ variants may be found at the National Center for Biotechnology Information (NCBI) website as Accession No. NP_001034597.1 (Isoform3 precursor; SEQ ID NO: 1), NP_061026.2 (Isoform 1 precursor; SEQ ID NO: 3), and NP 543006.2 (Isoform 2 precursor; SEQ ID NO: 5). The messenger RNA (mRNA) sequences of SIRPγ may be found at the NCBI website as Accession No. NM_001039508.1 (Transcript variant 3; SEQ ID NO: 2); Accession No. NM_018556.4 (Transcript variant 1; SEQ ID NO: 4); and Accession No. NM_080816.2 (Transcript variant 2; SEQ ID NO: 6). Among the variants, a protective intron variant rs2281808 within SIRPγ intron has been identified to be associated with decreased risk in Type 1 diabetes (T1D) development through several genome-wide association studies. A recent study of the rs2281808 intron variant indicated that the SNP variant resulted in the reduction of SIRPγ expression on T cells. However, the biological activity of SIRPγ is still largely unknown, partially because of the lack of homolog gene in mouse.

Previous studies have shown that anti-SIRPγ or anti-CD47 antibody can inhibit T cell proliferation and T-cell secretion of IFNγ triggered by allogeneic immature DCs in mixed lymphocyte reactions (Piccio et al., Blood, 105:2421-2427, 2005). However, in these previous studies, the binding epitope of anti-SIRPγ antibody is unknown and the mechanisms of anti-SIRPγ antibody's inhibitory effect on T cell proliferation are unclear. In such studies, it is unknown whether the blocking of CD47 and SIRPγ interaction by the antibody is the cause of decreased T cell proliferation, and it is unclear whether there are additional biological functions of SIRPγ beyond those involving its interaction with CD47.

In exemplary embodiments of the presently disclosed methods, a SIRPγ binder is administered to a subject. As used herein, the term "SIRPγ binder" refers to any compound or molecule that binds to SIRPγ to form a binding interaction with SIRPγ. In exemplary aspects, the SIRPγ binder comprises or is a small molecular weight compound, an amino acid, a peptide, a polypeptide, a protein, a polymer, a carbohydrate, a lipid, a nucleic acid, an oligonucleotide, a DNA or RNA. Optionally, the SIRPγ binder is a protein, such as, for instance, an antigen binding protein described herein. In some embodiments, the SIRPγ binder is an antibody or antigen binding fragment thereof.

In various instances, the binding interaction formed between SIRPγ and the SIRPγ binder is a non-covalent binding interaction. For example, the SIRPγ binder may in various aspects form ionic bonds, van der Waals interactions, hydrophobic bonds, and/or hydrogen bonds with one or more amino acid residues of SIRPγ. Optionally, the non-covalent binding interaction is a reversible, non-covalent binding interaction. The binding interaction may be described in terms of $K_D$, the equilibrium dissociation constant, a ratio of $k_{off}/k_{on}$, between SIRPγ and the SIRPγ binder. The lower the $K_D$ value of the SIRPγ binder the higher the affinity of the SIRPγ binder for SIRPγ. In exemplary aspects, the $K_D$ value of the SIRPγ binder for SIRPγ is micromolar, nanomolar, picomolar or femtomolar. In exemplary aspects, the $K_D$ of the antigen binding proteins provided herein is within a range of about $10^{-4}$ to $10^{-6}$ M, or $10^{-7}$ to $10^{-9}$ M, or $10^{-10}$ to $10^{-12}$ M, or $10^{-13}$ to $10^{-15}$ M. In exemplary aspects, the SIRPγ binder binds to SIRPγ with a $K_D$ of about 0.01 nM to about 20 nM, 0.02 nM to 20 nM, 0.05 nM to 20 nM, 0.05 nM to 15 nM, 0.1 nM to 15 nM, 0.1 nM to 10 nM, 1 nM to 10 nM, or 5 nM to 10 nM.

In various instances, the SIRPγ binder binds to D1 and/or binds to the CD47 binding site of SIRPγ. In various aspects, the SIRPγ binder binds to D1 and Ig Domain 2 (D2) of SIRPγ. In exemplary aspects, the SIRPγ binder binds to both D1 and D2, optionally at the interface between D1 and D2. Optionally, the SIRPγ binder binds to the binding site of a SIRPγ binding partner other than CD47. FIG. 9E provides an illustration of SIRPγ, its Ig domains thereof and the CD47 binding site. In exemplary instances, the SIRPγ binder binds to the epitope to which SIRPγ monoclonal antibody OX117 binds. In some embodiments, the SIRPγ binder competes with a reference antibody known to bind to SIRPγ (e.g., OX117) for binding to SIRPγ. The SIRPγ binder in various instances binds to SIRPγ with the same or higher affinity as OX117. In some embodiments, the SIRPγ binder is OX117, or an antigen binding fragment thereof. FIG. 9E provides an illustration of the binding interaction between SIRPγ and the fab of the OX117 antibody. The SIRPγ binder in various aspects forms hydrogen bonds with one or more of amino acid residues Q8, E10, G109, K11, L12, and D149 of SIRPγ. In some embodiments, the SIRPγ binder forms hydrogen bonds with each of amino acid residues Q8, E10, G109, K11, L12, and D149 of SIRPγ. In some embodiments, the SIRPγ binder binds to an epitope which does not overlap with the CD47 binding site.

In exemplary instances, upon binding to SIRPγ, the SIRPγ binder enhances T cell activation, T cell proliferation and cytokine secretion. In some instances, the methods of the disclosure increase the T cell activation, T cell proliferation and cytokine secretion to any degree or level relative to a control. For example, in some aspects, the increase provided by the methods of the disclosure is at least or about a 1% to about a 10% increase (e.g., at least or about a 1% increase, at least or about a 2% increase, at least or about a 3% increase, at least or about a 4% increase, at least or about a 5% increase, at least or about a 6% increase, at least or about a 7% increase, at least or about a 8% increase, at least or about a 9% increase, at least or about a 9.5% increase, at least or about a 9.8% increase, at least or about a 10% increase) relative to a control. In exemplary embodiments, the increase provided by the methods of the disclosure is over 100%, e.g., 200%, 300%, 400%, 500%, 600%, 700%, 800%, 900% or even 1000% relative to a control. In exemplary embodiments, the T cell activation, T cell proliferation and cytokine secretion increases by at least or about 1.5-fold, at least or about 2.0 fold, at least or about 3.0 fold, at least or about 4.0 fold, at least or about 5.0 fold, at least or about 10.0 fold, at least or about 25 hold, at least or about 50 fold, at least or about 75 fold, or at least or about 100 fold or mor, relative to a control. The control in various aspects is the T cell activation, T cell proliferation and cytokine secretion without the SIRPγ binder binding to SIRPγ.

In exemplary instances, the SIRPγ binder causes a conformational change of SIRPγ, upon binding to SIRPγ. The conformational change of SIRPγ may alter the accessibility of binding sites of binding partners. The conformational may also allow different binding partners to bind to SIRPγ. Additionally or alternatively, the conformational change may cause dimerization or multimerization of SIRPγ molecules. In exemplary aspects, the dimerization or multimerization of SIRPγ prevents one or more binding partners from binding to SIRPγ. In exemplary aspects, the dimerization or multimerization of SIRPγ enhances the binding of one or more binding partners binding to SIRPγ. In various instances, the SIRPγ binder simultaneously binds to two SIRPγ molecules or promotes SIRPγ dimerization.

In some embodiments, the SIRPγ binder blocks the function of SIRPγ, e.g., the SIRPγ binder is a SIRPγ inhibitor. Accordingly, in exemplary embodiments of the presently disclosed methods, a SIRPγ inhibitor is administered to a subject. As used herein, the term "SIRPγ inhibitor" refers to any compound or molecule that reduces or inhibits the function of SIRPγ. In exemplary instances, the SIRPγ inhibitor reduces the signal transduction that ensues upon the binding of a SIRPγ binding partner to SIRPγ. In various instances, the SIRPγ inhibitor reduces a binding interaction between SIRPγ and a SIRPγ binding partner. In various aspects, the SIRPγ inhibitor reduces expression of SIRPγ in cells of the subject. In some embodiments, the SIRPγ inhibitor binds SIRPγ. In other embodiments, the SIRPγ inhibitor binds a SIRPγ binding partner.

As used herein, the terms "inhibit" and "reduce" and words stemming therefrom do not necessarily mean a 100% or complete inhibition or abrogation or reduction. Rather, there are varying degrees of inhibition and/or reduction of which one of ordinary skill in the art recognizes as having a potential benefit or therapeutic effect. In this respect, the SIRPγ inhibitors of the present disclosure may reduce or inhibit the SIRPγ function to any amount or level. In exemplary embodiments, the reduction or inhibition provided by the SIRPγ inhibitor is at least or about a 10% reduction or inhibition (e.g., at least or about a 20% reduction or inhibition, at least or about a 30% reduction or inhibition, at least or about a 40% reduction or inhibition, at least or about a 50% reduction or inhibition, at least or about a 60% reduction or inhibition, at least or about a 70% reduction or inhibition, at least or about a 80% reduction or inhibition, at least or about a 90% reduction or inhibition, at least or about a 95% reduction or inhibition, at least or about a 98% reduction or inhibition, at least or about a 99% reduction or inhibition, or about a 100% reduction or inhibition).

In exemplary aspects, the SIRPγ inhibitor reduces expression of SIRPγ in cells of the subject. In certain instances, the SIRPγ inhibitor reduces cell surface expression of SIRPγ on T-cells. In exemplary aspects, the T cells are located within a tumor or a tumor microenvironment. In various instances, the T-cells are tumor-infiltrating T-cells. In exemplary aspects, the T-cells are T regulatory cells (Tregs). In various aspects, the T-cells are exhausted T-cells, optionally, exhausted CD8+ T-cells. Optionally, the T-cells are memory cells. In various aspects, the memory cells are CD8+ memory cells or CD4+ central memory cells. In exemplary instances, the SIRPγ inhibitor is a molecule that targets a nucleic acid encoding SIRPγ. In exemplary instances, the SIRPγ inhibitor is an antisense molecule which mediates RNA interference (RNAi). RNAi is a ubiquitous mechanism of gene regulation in plants and animals in which target mRNAs are degraded in a sequence-specific manner (Sharp, Genes Dev., 15, 485-490 (2001); Hutvagner et al., Curr. Opin. Genet. Dev., 12, 225-232 (2002); Fire et al., Nature, 391, 806-811 (1998); Zamore et al., Cell, 101, 25-33 (2000)). The natural RNA degradation process is initiated by the dsRNA-specific endonuclease Dicer, which promotes cleavage of long dsRNA precursors into double-stranded fragments between 21 and 25 nucleotides long, termed small interfering RNA (siRNA; also known as short interfering RNA) (Zamore, et al., Cell. 101, 25-33 (2000); Elbashir et al., Genes Dev., 15, 188-200 (2001); Hammond et al., Nature, 404, 293-296 (2000); Bernstein et al., Nature, 409, 363-366(2001)). siRNAs are incorporated into a large protein complex that recognizes and cleaves target mRNAs (Nykanen et al., Cell, 107, 309-321(2001). The requirement for Dicer in maturation of siRNAs in cells can be bypassed by introducing synthetic 21-nucleotide siRNA duplexes, which inhibit expression of transfected and endogenous genes in a variety of mammalian cells (Elbashir et al., Nature, 411: 494-498 (2001)). In exemplary aspects, the SIRPγ inhibitor mediates RNAi and in various instances is a siRNA molecule specific for inhibiting the expression of the nucleic acid (e.g., the mRNA) encoding the SIRPγ protein. The term "siRNA" as used herein refers to an RNA (or RNA analog) comprising from about 10 to about 50 nucleotides (or nucleotide analogs) which is capable of directing or mediating RNAi. In exemplary embodiments, a siRNA molecule comprises about 15 to about 30 nucleotides (or nucleotide analogs) or about 20 to about 25 nucleotides (or nucleotide analogs), e.g., 21-23 nucleotides (or nucleotide analogs). The siRNA can be double or single stranded, preferably double-stranded.

In alternative aspects, the SIRPγ inhibitor is a short hairpin RNA (shRNA)molecule specific for inhibiting the expression of the nucleic acid (e.g., the mRNA) encoding the SIRPγ protein. The term "shRNA" as used herein refers to a molecule of about 20 or more base pairs in which a single-stranded RNA partially contains a palindromic base sequence and forms a double-strand structure therein (i.e., a hairpin structure). An shRNA can be a siRNA (or siRNA analog) which is folded into a hairpin structure. shRNAs typically comprise about 45 to about 60 nucleotides, including the approximately 21 nucleotide antisense and sense portions of the hairpin, optional overhangs on the non-loop side of about 2 to about 6 nucleotides long, and the loop portion that can be, e.g., about 3 to 10 nucleotides long. The shRNA can be chemically synthesized. Alternatively, the shRNA can be produced by linking sense and antisense strands of a DNA sequence in reverse directions and synthesizing RNA in vitro with T7 RNA polymerase using the DNA as a template. Though not wishing to be bound by any theory or mechanism, it is believed that after shRNA is introduced into a cell, the shRNA is degraded into a length of about 20 bases or more (e.g., representatively 21, 22, 23 bases), and causes RNAi, leading to an inhibitory effect. Thus, shRNA elicits RNAi and therefore can be used as an effective component of the disclosure. shRNA may preferably have a 3'-protruding end. The length of the double-stranded portion is not particularly limited, but is preferably about 10 or more nucleotides, and more preferably about 20 or more nucleotides. Here, the 3'-protruding end may be preferably DNA, more preferably DNA of at least 2 nucleotides in length, and even more preferably DNA of 2-4 nucleotides in length.

In exemplary aspects, the SIRPγ inhibitor is a microRNA (miRNA). As used herein the term "microRNA" refers to a small (e.g., 15-22 nucleotides), non-coding RNA molecule which base pairs with mRNA molecules to silence gene expression via translational repression or target degradation. microRNA and the therapeutic potential thereof are described in the art. See, e.g., Mulligan, *MicroRNA: Expression, Detection, and Therapeutic Strategies*, Nova Science Publishers, Inc., Hauppauge, NY, 2011; Bader and Lammers, "The Therapeutic Potential of microRNAs" *Innovations in Pharmaceutical Technology*, pages 52-55 (March 2011).

In exemplary instances, the SIRPγ inhibitor reduces the signal transduction that ensues upon the binding of a SIRPγ binding partner to SIRPγ. In various aspects, the SIRPγ inhibitor reduces the signal transduction that ensues upon the binding of CD47 to SIRPγ, e.g., the signaling in endothelial cells induced by CD47-SIRPγ binding interactions that lead to T-cell transendothelial migration (Stefanidakis et al., Blood 112: 1280-1289 (2008)). In various aspects, the SIRPγ inhibitor reduces the signal transduction that ensues upon the binding of a SIRPγ binding partner to SIRPγ immunoglobulin domain D1 (D1) and/or immunoglobulin domain D2 (D2). In one instance, the SIRPγ inhibitor reduces the signal transduction that ensues upon the binding of a SIRPγ binding partner to the interface between SIRPγ immunoglobulin domain D1 and immunoglobulin domain D2. In various aspects, the SIRPγ inhibitor enhances secretion of IFNγ by activated T cells.

In various instances, the SIRPγ inhibitor reduces a binding interaction between SIRPγ and a SIRPγ binding partner. In exemplary aspects, the SIRPγ inhibitor inhibits at least or about 10% of the binding interactions between SIRPγ and the SIRPγ binding partner (e.g., at least or about 20% of the binding interactions, at least or about 30% of the binding interactions, at least or about 40% of the binding interactions, at least or about 50% of the binding interactions, at least or about 60% of the binding interactions, at least or about 70% of the binding interactions, at least or about 80% of the binding interactions, at least or about 90% of the binding interactions, at least or about 95% of the binding interactions, at least or about 98% of the binding interactions, at least or about 99% of the binding interactions, or about 100% of the binding interactions). In other instances, the SIRPγ binding partner binds to the interface between SIRPγ immunoglobulin domain D1 and immunoglobulin domain D2. In various instances, the SIRPγ binding partner is CD47. In various aspects, the SIRPγ binding partner binds to D1 and/or D2.

In exemplary aspects, the SIRPγ inhibitor is a soluble portion of SIRPγ which binds to CD47 or another SIRPγ binding partner. In various aspects, the soluble portion of SIRPγ is a decoy which, upon binding to CD47 or other SIRPγ binding partner, leads to a null response, e.g., a lack of SIRPγ-CD47-mediated signaling. In various aspects, the soluble portion of SIRPγ comprises at least amino acids 29-360 of the SIRPγ amino acid sequence. In exemplary aspects, the soluble portion of SIRPγ comprises at least amino acids 29-360 of SEQ ID NO: 3 (NCBI Accession No. NP_061026.2), the human SIRPγ amino acid sequence.

In some embodiments, the SIRPγ inhibitor is a SIRPγ-Fc which binds to CD47 or other SIRPγ binding partners. In various aspects, the SIRPγ-Fc is a decoy which, upon binding to CD47 or other SIRPγ binding partners, leads to a null response, e.g., a lack of SIRPγ-CD47-mediated signaling. In various aspects, the SIRPγ-Fc comprises at least amino acids 29-360 of the SIRPγ amino acid sequence.

In some embodiments, the SIRPγ inhibitor is a CRISPR gRNA. CRISPR knockout systems contain a guide RNA (gRNA) and a CRISPR-associated endonuclease (Cas protein). The term "gRNA" as used herein refers to a short RNA molecule of about 100 or more base pairs. The gRNA contains ~20 base pairs of nucleotide spacer and a scaffold sequence required for Cas protein binding. By altering the 20 base pairs towards the 5' end of the gRNA, the gRNA can be targeted towards any genomic region complementary to that sequence. The 20 base pairs long nucleotide spacer can be chemically synthesized and annealed to scaffold RNA to form gRNA in vitro. Full length of gRNA can be chemically synthesized in vitro. Alternatively, the gRNA can be produced by viral vectors that driven by U6 RNA polymerase III promoter. The desired 20 base pair target sequence immediately precede s a protospacer adjacent motif (PAM). The gRNA guides the Cas nuclease to the target sequence by complementary base pairing and Cas nuclease mediates a double strand break a few nucleotides upstream of the PAM sequence. Targeted cells will use non-homologous end joining (NHEJ) or homology directed repair (HDR) to repair the double strand break. In many cases, NHEJ causes deletions, insertions, or frameshift mutations in the targeted DNA region and results a loss-of function mutation of the targeted gene.

In exemplary aspects, the SIRPγ inhibitor is a soluble portion of CD47 which binds to SIRPγ. In various aspects, the soluble portion of CD47 is a decoy which, upon binding to SIRPγ, leads to a null response, e.g., a lack of SIRPγ-CD47-mediated signaling. In various aspects, the soluble portion of CD47 comprises at least amino acids 26-133 of the CD47 amino acid sequence. In exemplary aspects, the soluble portion of CD47 comprises at least amino acids 26-133 of NCBI Accession No. NP_001768.1, the human CD47 amino acid sequence.

Antigen-Binding Proteins

In exemplary instances, the SIRPγ binder, e.g., SIRPγ inhibitor, is an antigen-binding protein that binds to SIRPγ. In exemplary aspects, the SIRPγ inhibitor, is an antigen-binding protein that binds to SIRPγ or the SIRPγ binding partner (e.g., CD47). The antigen-binding protein in various aspects is an antibody, an antigen-binding antibody fragment, or an antibody protein product. As used herein, the term "antibody" refers to a protein having a known immunoglobulin format, comprising heavy and light chains, and comprising variable and constant regions. For example, an antibody can be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has variable regions and constant regions. In IgG formats, the variable region is generally about 100-110 or more amino acids, comprises three complementarity determining regions (CDRs), is primarily responsible for antigen recognition, and substantially varies among other antibodies that bind to different antigens. The constant region allows the antibody to recruit cells and molecules of the immune system. The variable region is made of the N-terminal regions of each light chain and heavy chain, while the constant region is made of the C-terminal portions of each of the heavy and light chains. (Janeway et al., "Structure of the Antibody Molecule and the Immunoglobulin Genes", *Immunobiology: The Immune System in Health and Disease,* 4th ed. Elsevier Science Ltd./Garland Publishing, (1999)).

The general structure and properties of CDRs of antibodies have been described in the art. Briefly, in an antibody scaffold, the CDRs are embedded within the heavy and light chain variable regions where they constitute the regions largely responsible for antigen binding and recognition. A variable region typically comprises at least three heavy or light chain CDRs (Kabat et al., 1991, *Sequences of Proteins of Immunological Interest,* Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991; see also Chothia and Lesk, 1987, supra).

Antibodies can comprise any constant region known in the art. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the present disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in exemplary embodiments, the antibody is an antibody of isotype IgA, IgD, IgE, IgG, or IgM, including anyone of IgG1, IgG2, IgG3 or IgG4. In some embodiments, the antibody is an IgG1, IgG2, IgG3, or IgG4 antibody.

The antibody can be a monoclonal antibody or a polyclonal antibody. In some embodiments, the antibody comprises a sequence that is substantially similar to a naturally-occurring antibody produced by a mammal, e.g., mouse, rabbit, goat, horse, chicken, hamster, human, and the like. In this regard, the antibody can be considered as a mammalian antibody, e.g., a mouse antibody, rabbit antibody, goat antibody, horse antibody, chicken antibody, hamster antibody, human antibody, and the like. In certain aspects, the antibody is a human antibody. In certain aspects, the antibody is a chimeric antibody or a humanized antibody. The term "chimeric antibody" refers to an antibody containing domains from two or more different antibodies. A chimeric antibody can, for example, contain the constant domains from one species and the variable domains from a second, or more generally, can contain stretches of amino acid sequence from at least two species. A chimeric antibody also can contain domains of two or more different antibodies within the same species. The term "humanized" when used in relation to antibodies refers to antibodies having at least CDR regions from a non-human source which are engineered to have a structure and immunological function more similar to true human antibodies than the original source antibodies. For example, humanizing can involve grafting a CDR from a non-human antibody, such as a mouse antibody, into a human antibody. Humanizing also can involve select amino acid substitutions to make a non-human sequence more similar to a human sequence.

An antibody can be cleaved into fragments by enzymes, such as, e.g., papain and pepsin. Papain cleaves an antibody to produce two Fab fragments and a single Fc fragment. Pepsin cleaves an antibody to produce a $F(ab')_2$ fragment and a pFc' fragment. In exemplary aspects of the present disclosure, the antigen-binding protein is an antigen binding fragment of an antibody. As used herein, the term "antigen binding antibody fragment" refers to a portion of an antibody that is capable of binding to the antigen of the antibody and is also known as "antigen-binding fragment" or "antigen-binding portion". In exemplary instances, the antigen binding antibody fragment is a Fab fragment or a $F(ab')_2$ fragment.

In various aspects, the antigen-binding protein is an antibody protein product. As used herein, the term "antibody protein product" refers to anyone of several antibody alternatives which in various instances is based on the architecture of an antibody but is not found in nature. In some aspects, the antibody protein product has a molecular-weight within the range of at least about 12-150 kDa. In certain aspects, the antibody protein product has a valency (n) range from monomeric (n=1), to dimeric (n=2), to trimeric (n=3), to tetrameric (n=4), if not higher order valency. Antibody protein products in some aspects are those based on the full antibody structure and/or those that mimic antibody fragments which retain full antigen-binding capacity, e.g., scFvs, Fabs and VHH/VH (discussed below).

The smallest antigen binding antibody fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab fragments can be easily produced in host cells, e.g., prokaryotic host cells. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., *mAbs* 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, BsAb fragments, bispecific fusion proteins and BsAb conjugates. See, e.g., Spiess et al., *Molecular Immunology* 67(2) Part A: 97-106 (2015).

In exemplary aspects, the antigen-binding protein is a bispecific T cell engager (BiTE®) molecule. BiTE® molecules are fusion proteins comprising two scFvs of different antibodies. One binds to CD3 and the other binds to a target antigen. BiTE® molecules are known in the art. See, e.g., Huehls et al., *Immuno Cell Biol* 93(3): 290-296 (2015); Rossi et al., *MAbs* 6(2): 381-91 (2014); Ross et al., *PLoS One* 12(8): e0183390.

In various aspects, the antigen-binding protein (e.g., an antibody or antigen binding fragment thereof) binds to a SIRPγ. The antigen-binding protein in some aspects binds to SIRPγ in a non-covalent and reversible manner. In exemplary embodiments, the binding strength of the antigen-binding proteins may be described in terms of its affinity, a measure of the strength of interaction between the binding site of SIRPγ and the SIRPγ binding partner. In exemplary aspects, the antigen-binding proteins have high-affinity for SIRPγ and thus will bind a greater amount of SIRPγ in a shorter period of time than low-affinity antigen-binding proteins. In exemplary aspects, the antigen-binding proteins have low-affinity for SIRPγ and thus will bind a lesser amount of SIRPγ in a longer period of time than high-affinity antigen-binding proteins. In exemplary aspects, the antigen-binding proteins have an equilibrium association constant, KA, which is at least $10^5$ M$^{-1}$, at least $10^6$ M$^{-1}$, at least $10^7$ M$^{-1}$, at least $10^8$ M$^{-1}$, at least $10^9$ M$^{-1}$, or at least $10^{10}$ M$^{-1}$. As understood by the artisan of ordinary skill, KA can be influenced by factors including pH, temperature and buffer composition.

In exemplary embodiments, the binding strength of the antigen-binding protein (e.g., an antibody or antigen binding fragment thereof) to SIRPγ may be described in terms of its sensitivity. $K_D$ is the equilibrium dissociation constant, a ratio of $k_{off}/k_{on}$, between the antigen-binding protein and SIRPγ. $K_D$ and KA are inversely related. The $K_D$ value relates to the concentration of the antigen-binding protein (the amount of antigen-binding protein needed for a particular experiment); the lower the $K_D$ value (lower concentration needed) the higher the affinity of the antigen-binding protein. In exemplary aspects, the binding strength of the antigen-binding protein to SIRPγ may be described in terms of $K_D$. In exemplary aspects, the $K_D$ of the antigen-binding proteins is about $10^{-1}$ M, about $10^{-2}$ M, about $10^{-3}$ M, about $10^{-4}$ M, about $10^{-5}$ M, about $10^{-6}$ M, or less. In exemplary aspects, the $K_D$ of the antigen-binding protein is micromolar, nanomolar, picomolar or femtomolar. In exemplary aspects, the $K_D$ of the antigen-binding proteins is within a range of about $10^{-4}$ to $10^{-6}$ M, or $10^{-7}$ to $10^{-9}$ M, or $10^{-10}$ to $10^{-12}$ M, or $10^{-13}$ to $10^{-15}$ M. In exemplary aspects, the antigen-binding protein binds to the human SIRPγ with a $K_D$ that is greater than or is about 0.04 nM. In exemplary aspects, the antigen-binding protein binds to the human SIRPγ with a $K_D$ of about 0.01 nM to about 20 nM, 0.02 nM to 20 nM, 0.05 nM to 20 nM, 0.05 nM to 15 nM, 0.1 nM to 15 nM, 0.1 nM to 10 nM, 1 nM to 10 nM, or 5 nM to 10 nM. In various aspects, the $K_D$ is less than the $K_D$ that SIRPγ has for CD47, optionally, less than about 23 μM.

Optionally, the antigen-binding protein comprises a fully human antibody or antigen binding fragment thereof, a humanized antibody or antigen binding fragment thereof, a chimeric antibody or antigen binding fragment thereof. The antigen-binding protein may also comprise a Fab, Fab', F(ab')2, or a single chain Fv. In various aspects, the SIRPγ inhibitor comprises one, two, three, four, five or more of the heavy and light chain complementarity determining region (CDR) of an anti-SIRPγ antibody.

In certain aspects, the antigen-binding protein binds to an epitope on SIRPγ, optionally, wherein the epitope is located within or near or different from the CD47 binding site of SIRPγ. In various aspects, the antigen-binding protein binds to an epitope comprising the amino acid sequence of SLLPVGP (SEQ ID NO: 21; amino acids 29-35 of the SIRPγ amino acid sequence, LTKRNNMDF (SEQ ID NO: 22), and KFRKGS (SEQ ID NO: 23).

In exemplary aspects, the antigen-binding protein comprises a fully human antibody or antigen binding fragment thereof, a humanized antibody or antigen binding fragment thereof, a chimeric antibody or antigen binding fragment thereof, or a Fab, Fab', F(ab')2, or a single chain Fv, that competes with a reference antibody, which reference antibody is known to bind to SIRPγ (e.g., OX117), for binding to SIRPγ. In exemplary aspects, the antigen-binding protein binds to an epitope to which the reference antibody (e.g., OX117) binds. In exemplary aspects, the antigen-binding protein exhibits a $K_D$ for SIRPγ that is similar to, or the same as, the $K_D$ of the reference antibody (e.g., OX117). In exemplary aspects, the antigen-binding protein exhibits a $K_D$ for SIRPγ that is lower than the $K_D$ of the reference antibody (e.g., OX117) and thus exhibits higher affinity for SIRPγ relative to the reference antibody. Suitable techniques for determining binding affinity for a ligand or target of an antigen binding protein are known in the art and include, e.g., surface plasmon resonance (SPR)-based methods, flow cytometry- or fluorescence microscopy-based methods, KinExA® method (see, e.g., International Patent Application Publication No. WO2019140196, Azimzadeh and Regenmortel, J Mol Recognit 3(3): 108-116 (1990); Schuck et al., Curr Protoc Cell Biol Chapter 17: Unit 17.6 (2004); Tseng et al., Electrophoresis 23(6): 836-846 (2002); Van Regenmortel et al., Immunol Invest 26(1-2): 67-82 (1997)).

In exemplary instances, the antigen-binding protein that competes with a reference antibody (e.g., OX117) for binding to SIRPγ reduces the amount of the anti-SIRPγ antibody (e.g., OX117) bound to SIRPγ in an in vitro competitive binding assay. In exemplary aspects, the amount of the reference antibody (e.g., OX117) bound to SIRPγ in the presence of the antigen binding protein of the present disclosure is reduced by at least or about 25%, at least or about 30%, at least or about 35%, at least or about 40%, at least or about 45%, at least or about 50%, at least or about 55%, at least or about 60%, at least or about 65%, at least or about 70%, at least or about 75%, at least or about 80%, at least or about 85%, at least or about 90% or more (e.g., at least or about 95%, at least or about 98%). In various aspects, the antigen-binding proteins of the present disclosure inhibit the binding interaction between SIRPγ and the reference antibody and the inhibition are characterized by an $IC_{50}$. In various aspects, the antigen-binding proteins exhibit an $IC_{50}$ of less than about 250 nM for inhibiting the binding interaction between SIRPγ and the reference antibody. In various aspects, the antigen-binding proteins exhibit an $IC_{50}$ of less than about 200 nM, less than about 150 nM, less than about 100 nM, less than about 50 nm, less than about 25 nm, less than about 10 nm, less than about 5 nM, less than about 1 nM, less than 0.5 nM or less than 0.1 nM.

A suitable competitive binding assay that can be used to determine the reduced amount of the reference antibody (e.g., OX117) bound to SIRPγ comprises the steps of incubating the reference antibody (e.g., OX117) with SIRPγ or cells expressing SIRPγ in the presence of a presently disclosed antigen-binding protein (e.g., an antibody or antigen binding fragment thereof) that competes with the reference antibody (e.g., OX117) for binding to SIRPγ. The amount of the reference antibody (e.g., OX117) bound to SIRPγ is measured with and without the antigen-binding protein (e.g., an antibody or antigen binding fragment thereof) of the present disclosure that competes for binding to SIRPγ.

In various instances, the antigen-binding proteins of the present disclosure compete with the reference antibody for binding to SIRPγ and thereby reduce the amount of SIRPγ bound to the reference antibody as determined by a FACS-based assay in which the fluorescence of a fluorophore-conjugated secondary antibody which binds to the Fc of the reference antibody is measured in the absence or presence of a particular amount of the antigen-binding protein of the present disclosure. In various aspects, the FACS-based assay is carried out with the reference antibody, fluorophore-conjugated secondary antibody and cells which express SIRPγ. In various aspects, the cells are genetically-engineered to overexpress SIRPγ. In some aspects, the cells are HEK293T cells transduced with a viral vector to express SIRPγ. In alternative aspects, the cells endogenously express SIRPγ. Before the FACS-based assay is carried out, in some aspects, the cells which endogenously express SIRPγ are pre-determined as low SIRPγ-expressing cells or high SIRPγ-expressing cells.

Other binding assays, e.g., competitive binding assays or competition assays, which test the ability of an antibody to compete with another antigen-binding protein for binding to an antigen, or to an epitope thereof, are known in the art. For example, suitable receptor-ligand competition assays are described in International Patent Application Publication No. WO2019140196, incorporated herein by reference. See, e.g., Trikha et al., Int J Cancer 110: 326-335 (2004); Tam et al., Circulation 98(11): 1085-1091 (1998); U.S. Patent Application Publication No. US20140178905, Chand et al., Biologicals 46: 168-171 (2017); Liu et al., Anal Biochem 525: 89-91 (2017); Goolia et al., J Vet Diagn Invest 29(2): 250-253 (2017); Hunter and Cochran, Methods Enzymol 250: 21-44 (2016); Cox et al., Immunoassay Methods, Immunoassay Methods. 2012 May 1 [Updated 2019 Jul. 8]. In: Sittampalam G S, Grossman A, Brimacombe K, et al., editors. Assay Guidance Manual [Internet]. Bethesda (MD): Eli Lilly & Company and the National Center for Advancing Translational Sciences; 2004-. Available from: www.ncbi.nlm.nih.gov/books/NBK92434/; Clarke, William, "Immunoassays for Therapeutic Drug Monitoring and Clinical Toxicology", *Handbook of Analytical Separations*, Volume 5, pages 95-112 (2004), and Goolia et al., J Vet Diagn Invest 29(2): 250-253 (2017). In exemplary aspects, the SIRPγ binder competes with OX117 for binding to SIRPγ as determined by any of the assays described in these references.

Treatment of Cancer

The present disclosure provides methods of treating a subject with a tumor or cancer. In exemplary embodiments, the method of treating cancer comprises administering to the subject a SIRPγ binder (e.g., an antibody or antigen binding fragment thereof) in an amount effective to treat the tumor or cancer in the subject. In some embodiments, the SIRPγ binder is a SIRPγ inhibitor. In some embodiments, the method of treating cancer comprises administering to the subject an antigen-binding protein (e.g., an antibody or antigen binding fragment thereof) that binds to an epitope on SIRPγ in an amount effective to treat the tumor or cancer in the subject.

Any of the antigen-binding proteins that bind to an epitope on SIRPγ (e.g., SIRPγ binders and SIRPγ inhibitors) discussed herein may be used in such methods. In certain aspects, the SIRPγ binder or SIRPγ inhibitor (e.g., an antibody or antigen binding fragment thereof) binds to an epitope on SIRPγ. In some embodiments, the epitope on SIRPγ is located within or near or different from the CD47 binding site of SIRPγ. In various aspects, the SIRPγ binder or SIRPγ inhibitor (e.g., an antibody or antigen binding fragment thereof) binds to an epitope comprising the amino acid sequence of SLLPVGP (SEQ ID NO: 21; amino acids 29-35 of the SIRPγ amino acid sequence, LTKRNNMDF (SEQ ID NO: 22), and KFRKGS (SEQ ID NO: 23).

In various instances, the SIRPγ binder binds to D1 and/or binds to the CD47 binding site of SIRPγ. In various aspects, the SIRPγ binder binds to D1 and Ig Domain 2 (D2) of SIRPγ. In exemplary aspects, the SIRPγ binder binds to both D1 and D2, optionally at the interface between D1 and D2. Optionally, the SIRPγ binder binds to the binding site of a SIRPγ binding partner other than CD47. FIG. 9E provides an illustration of SIRPγ, its Ig domains thereof and the CD47 binding site. In exemplary instances, the SIRPγ binder binds to the epitope to which SIRPγ monoclonal antibody OX117 binds, optionally, wherein the SIRPγ binder competes with a reference antibody known to bind to SIRPγ (e.g., OX117) for binding to SIRPγ. In some embodiments, the SIRPγ binder competes with OX117 for binding to SIRPγ. The SIRPγ binder in various instances binds to SIRPγ with the same or higher affinity as OX117. In some embodiments, the SIRPγ binder is OX117 or an antigen binding fragment thereof. FIG. 9E provides an illustration of the binding interaction between SIRPγ and the fab of the OX117 antibody. The SIRPγ binder in various aspects forms hydrogen bonds with one or more of amino acid residues Q8, E10, G109, K11, L12, and D149 of SIRPγ. The SIRPγ binder in various aspects forms hydrogen bonds with each of amino acid residues Q8, E10, G109, K11, L12, and D149 of SIRPγ. Optionally, the SIRPγ binder binds to an epitope which does not overlap with the CD47 binding site.

In exemplary instances, upon binding to SIRPγ, the SIRPγ binder enhances T cell activation, T cell proliferation and cytokine secretion. In some instances, the methods of the disclosure increase the T cell activation, T cell proliferation and cytokine secretion to any degree or level relative a control. For example, in some aspects, the increase provided by the methods of the disclosure is at least or about a 1% to about a 10% increase (e.g., at least or about a 1% increase, at least or about a 2% increase, at least or about a 3% increase, at least or about a 4% increase, at least or about a 5% increase, at least or about a 6% increase, at least or about a 7% increase, at least or about a 8% increase, at least or about a 9% increase, at least or about a 9.5% increase, at least or about a 9.8% increase, at least or about a 10% increase) relative a control. In exemplary embodiments, the increase provided by the methods of the disclosure is over 100%, e.g., 200%, 300%, 400%, 500%, 600%, 700%, 800%, 900% or even 1000% relative a control. In exemplary embodiments, the T cell activation, T cell proliferation and cytokine secretion increases by at least or about 1.5-fold, at least or about 2.0 fold, at least or about 3.0 fold, at least or about 4.0 fold, at least or about 5.0 fold, at least or about 10.0 fold, at least or about 25 hold, at least or about 50 fold, at least or about 75 fold, at least or about 100 fold or more, relative to a control. The control in various aspects is the T cell activation, T cell proliferation and cytokine secretion without the SIRPγ binder binding to SIRPγ.

In exemplary instances, the SIRPγ binder causes a conformational change of SIRPγ, upon binding to SIRPγ. The conformational change of SIRPγ in various instances may alter the accessibility of binding sites of binding partners. Optionally, the conformational change in various aspects allows different binding partners to bind to SIRPγ. Additionally or alternatively, the conformational change may cause dimerization or multimerization of SIRPγ molecules. In exemplary aspects, the dimerization or multimerization of SIRPγ prevents one or more binding partners from binding to SIRPγ. In exemplary aspects, the dimerization or multimerization of SIRPγ enhances the binding of one or more binding partners binding to SIRPγ. In various instances, the SIRPγ binder simultaneously binds to two SIRPγ molecules or promotes SIRPγ dimerization.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating cancer of the present disclosure can provide any amount or any level of treatment. Furthermore, the treatment provided by the methods of the present disclosure can include treatment of one or more conditions or symptoms or signs of the cancer being treated. Also, the treatment provided by the methods of the present disclosure can encompass slowing the progression of the cancer. For example, the methods can treat cancer by virtue of increasing T cell activity (e.g., T cell effector activity) or increasing an immune response against the tumor or cancer, reducing tumor or cancer growth or tumor burden, reducing metastasis of tumor cells, increasing cell death of tumor or cancer cells or increasing tumor regression, reducing T cell suppressive activity, and the like. In accordance with the foregoing, provided herein are methods of increasing effector activity or reducing suppressive activity of T-cells in a subject with a tumor or cancer. In exemplary embodiments, the method comprises administering to the subject a SIRPγ inhibitor in an amount effective to increase the effector activity or reduce the suppressive activity in the subject. Also, in accordance with the foregoing, provided herein are methods of increasing an immune response against a tumor or cancer in a subject. In exemplary embodiments, the method comprises administering to the subject a SIRPγ inhibitor in an amount effective to increase an immune response against a tumor or cancer.

In various aspects, the methods treat by way of delaying the onset or recurrence of the cancer by at least 1 day, 2 days, 4 days, 6 days, 8 days, 10 days, 15 days, 30 days, two months, 3 months, 4 months, 6 months, 1 year, 2 years, 3 years, 4 years, or more. In various aspects, the methods treat by way increasing the survival of the subject. In exemplary aspects, the methods of the present disclosure provide treatment by way of delaying the occurrence or onset of metastasis. In various instances, the methods provide treatment by way of delaying the occurrence or onset of a new metastasis.

SIRPγ Binder Pharmaceutical Compositions, Routes and Timing of Administration

The following embodiments disclose pharmaceutical compositions, routes and timing of administration of the antigen-binding proteins (e.g., an antibody or antigen binding fragment thereof) of the present invention that bind to SIRPγ. In some embodiments the antigen-binding protein is a SIRPγ binder or a SIRPγ inhibitor (e.g., an antibody or antigen binding fragment thereof).

In some embodiments, the SIRPγ binder or SIRPγ inhibitor (e.g., an antibody or antigen binding fragment thereof) that binds to SIRPγ is administered to a subject as part of a pharmaceutical composition. In other embodiments, the pharmaceutical composition comprises a SIRPγ binder or SIRPγ inhibitor (e.g., an antibody or antigen binding fragment thereof) or a pharmaceutically-acceptable salt thereof that binds to SIRPγ. In various aspects, the pharmaceutically-acceptable salt of the SIRPγ binder or SIRPγ inhibitor (e.g., an antibody or antigen binding fragment thereof) that binds to SIRPγ is prepared in situ during the final isolation and purification of the SIRPγ binder or SIRPγ inhibitor (e.g., an antibody or antigen binding fragment thereof) that binds to SIRPγ, or separately prepared by reacting a free base function with a suitable acid. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid. The acid addition salts in various aspects is acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxy-ethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate.

In various aspects, the pharmaceutically-acceptable salt of the SIRPγ binder or SIRPγ inhibitor (e.g., an antibody or antigen binding fragment thereof) that binds to SIRPγ is a basic addition salt. Basic addition salts also can be prepared in situ during the final isolation and purification of the SIRPγ binder or SIRPγ inhibitor (e.g., an antibody or antigen binding fragment thereof) that binds to SIRPγ, or by reacting a carboxylic acid-containing moiety with a suitable base such as the hydroxide, carbonate, or bicarbonate of a pharmaceutically acceptable metal cation or with ammonia or an organic primary, secondary, or tertiary amine. In various instances, the pharmaceutically acceptable salt of the SIRPγ binder or SIRPγ inhibitor (e.g., an antibody or antigen binding fragment thereof) that binds to SIRPγ is a cation based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like. Further, basic nitrogen-containing groups can be quaternized with such SIRPγ inhibitors as lower alkyl halides such as methyl, ethyl, propyl, and butyl chlorides, bromides, and iodides; long chain halides such as decyl, lauryl, myristyl, and stearyl chlorides, bromides, and iodides; arylalkyl halides like benzyl and phenethyl bromides and others. Water or oil-soluble or dispersible products are thereby obtained.

In various aspects, the SIRPγ binder or SIRPγ inhibitor (e.g., an antibody or antigen binding fragment thereof) that binds to SIRPγ of the presently disclosed methods is formulated with a pharmaceutically acceptable carrier, diluent, or excipient prior to administration to the subject. Depending on the route of administration and other factors, the particular SIRPγ binder or SIRPγ inhibitor (e.g., an antibody or antigen binding fragment thereof) that binds to SIRPγ, may be admixed with one or more additional pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

The SIRPγ binder or SIRPγ inhibitor (e.g., an antibody or antigen binding fragment thereof) that binds to SIRPγ of the presently disclosed methods can be administered to the subject via any suitable route of administration. For example, the SIRPγ binder or SIRPγ inhibitor (e.g., an antibody or antigen binding fragment thereof) that binds to SIRPγ can be administered to a subject via parenteral, nasal, oral, pulmonary, topical, vaginal, or rectal administration. The following discussion on routes of administration is merely provided to illustrate exemplary embodiments and should not be construed as limiting the scope in any way.

In exemplary aspects, the SIRPγ binder or SIRPγ inhibitor (e.g., an antibody or antigen binding fragment thereof) that binds to SIRPγ of the presently disclosed methods is formulated for parenteral administration. The term, "parenteral" means not through the alimentary canal but by some other route such as subcutaneous, intramuscular, intraspinal, or intravenous. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The SIRPγ binder or SIRPγ inhibitor (e.g., an antibody or antigen binding fragment thereof) that binds to SIRPγ can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, com, olive, petrolatum, and mineral. Suitable fatty acids for use in parenteral formulations include oleic acid, stearic acid, and isostearic acid. Ethyl oleate and isopropyl myristate are examples of suitable fatty acid esters. In exemplary aspects, the formulation for parenteral administration includes a soap. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof. In exemplary instances, preservatives and buffers are present in the parenteral formulation. In order to minimize or eliminate irritation at the site of injection, such compositions can contain one or more nonionic surfactants having a hydrophile-lipophile balance (HLB) of from about 12 to about 17. The quantity of surfactant in such formulations typically ranges from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, syringes, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

In exemplary aspects, the SIRPγ binder or SIRPγ inhibitor (e.g., an antibody or antigen binding fragment thereof) that binds to SIRPγ is formulated for injection. Injectable formulations are in accordance with the present disclosure. The requirements for effective pharmaceutical carriers for injectable compositions are well-known to those of ordinary skill in the art (see, e.g., *Pharmaceutics and Pharmacy Practice*, J. B. Lippincott Company, Philadelphia, PA, Banker and Chalmers, eds., pages 238-250 (1982), and *ASHP Handbook on Injectable Drugs*, Toissel, 4th ed., pages 622-630 (1986)).

Optionally, the SIRPγ binder or SIRPγ inhibitor (e.g., an antibody or antigen binding fragment thereof) that binds to SIRPγ is administered to the subject via subcutaneous injection.

In various instances the SIRPγ binder or SIRPγ inhibitor (e.g., an antibody or antigen binding fragment thereof) that binds to SIRPγ is administered orally to the subject. Formulations suitable for oral administration can consist of (a) liquid solutions, such as an effective amount of the analog of the present disclosure dissolved in diluents, such as water, saline, or orange juice; (b) capsules, sachets, tablets, lozenges, and troches, each containing a predetermined amount of the active ingredient, as so lids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the analog of the present disclosure in a flavor, usually sucrose and acacia or tragacanth, as well as pastilles comprising the analog of the present disclosure in an inert base, such as gelatin and glycerin, or sucrose and acacia, emulsions, gels, and the like containing, in addition to, such excipients as are known in the art.

The SIRPγ binder or SIRPγ inhibitor (e.g., an antibody or antigen binding fragment thereof) that binds to SIRPγ may be administered according to any regimen including, for example, daily (1 time per day, 2 times per day, 3 times per day, 4 times per day, 5 times per day, 6 times per day), three times a week, twice a week, every two days, every three days, every four days, every five days, every six days, weekly, bi-weekly, every three weeks, monthly, or bi-monthly.

Dosages

The following embodiments disclose dosages of the antigen-binding proteins (e.g., an antibody or antigen binding fragment thereof) of the present invention that bind to SIRPγ. In some embodiments the antigen-binding protein is a SIRPγ binder or a SIRPγ inhibitor (e.g., an antibody or antigen binding fragment thereof).

The SIRPγ binder or SIRPγ inhibitor (e.g., an antibody or antigen binding fragment thereof) that binds to SIRPγ is believed to be useful in methods of increasing effector activity or reducing suppressive activity of T-cells or increasing an immune response against a tumor or cancer in a subject, as described herein, and are thus believed to be useful in methods of treating or preventing one or more diseases, e.g., cancer. The amount or dose of the SIRPγ binder or SIRPγ inhibitor, or antigen-binding protein (e.g., an antibody or antigen binding fragment thereof) that binds to SIRPγ administered should be sufficient to effect, e.g., a therapeutic or prophylactic response, in the subject or animal over a reasonable time frame. For example, the dose of the SIRPγ binder or SIRPγ inhibitor, or antigen-binding protein (e.g., an antibody or antigen binding fragment thereof) that binds to SIRPγ (e.g., a SIRPγ inhibitor) should be sufficient to treat cancer in a period of from about 1 to 4 about days or about 1 to about 4 weeks or longer, e.g., about 5 to about 20 or more weeks, from the time of administration. In certain embodiments, the time period could be even longer. The dose will be determined by the efficacy of the particular active agent and the condition of the animal (e.g., human), as well as the body weight of the animal (e.g., human) to be treated.

Many assays for determining an administered dose are known in the art. For purposes herein, an assay, which comprises comparing secretion of IFNγ by activated T cells, upon administration of a given dose of the SIRPγ binder or SIRPγ inhibitor, or antigen-binding protein (e.g., an antibody or antigen binding fragment thereof) that binds to SIRPγ to a mammal among a set of mammals, each set of which is given a different dose, could be used to determine a starting dose to be administered to a mammal in a clinical trial. Methods of measuring secretion of IFNγ by activated T cells are known in the art and described herein.

The dose of the SIRPγ binder or SIRPγ inhibitor, or antigen-binding protein (e.g., an antibody or antigen binding fragment thereof) that binds to SIRPγ also will be determined by the existence, nature and extent of any adverse side effects that might accompany the administration of a particular active agent. Typically, the attending physician will decide the dosage of the SIRPγ binder, SIRPγ inhibitor, or antigen-binding protein (e.g., an antibody or antigen binding fragment thereof) that binds to SIRPγ with which to treat each individual patient, taking into consideration a variety of factors, such as age, body weight, general health, diet, sex, SIRPγ binder, SIRPγ inhibitor, or antigen-binding protein (e.g., an antibody or antigen binding fragment thereof) that binds to SIRPγ to be administered, route of administration, and the severity of the condition being treated. By way of example and not intending to limit the present disclosure, the dose of the SIRPγ binder, SIRPγ inhibitor, or antigen-binding protein (e.g., an antibody or antigen binding fragment thereof) that binds to SIRPγ of the presently disclosed methods can be about 0.0001 to about 1 g/kg body weight of the subject being treated/day, from about 0.0001 to about 0.001 g/kg body weight/day, or about 0.01 mg to about 1 g/kg body weight/day.

Controlled Release Formulations

The following embodiments disclose controlled release formulations of the antigen-binding proteins (e.g., an antibody or antigen binding fragment thereof) of the present invention that bind to SIRPγ. In some embodiments the antigen-binding protein is a SIRPγ binder or a SIRPγ inhibitor (e.g., an antibody or antigen binding fragment thereof).

In some embodiments, the SIRPγ binder or SIRPγ inhibitor (e.g., an antibody or antigen binding fragment thereof) that binds to SIRPγ described herein can be modified into a depot form, such that the manner in which the active agent is released into the body to which it is administered is controlled with respect to time and location within the body (see, for example, U.S. Pat. No. 4,450,150). Depot forms of the SIRPγ binder or SIRPγ inhibitor (e.g., an antibody or antigen binding fragment thereof) that binds to SIRPγ can be, for example, an implantable composition comprising the SIRPγ binder or SIRPγ inhibitor (e.g., an antibody or antigen binding fragment thereof) and a porous or non-porous material, such as a polymer, wherein the SIRPγ binder or SIRPγ inhibitor (e.g., an antibody or antigen binding fragment thereof) is encapsulated by or diffused throughout the material and/or degradation of the non-porous material. The depot is then implanted into the desired location within the body of the subject and the SIRPγ binder or SIRPγ inhibitor (e.g., an antibody or antigen binding fragment thereof) that binds to SIRPγ is released from the implant at a predetermined rate.

In various aspects, the pharmaceutical composition comprising the SIRPγ binder or SIRPγ inhibitor (e.g., an antibody or antigen binding fragment thereof) that binds to SIRPγ may be modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., *J Pharm* 374:46-52(2009) and International Patent Application Publication Nos. WO 2008/130158, WO2004/033036; WO2000/032218; and WO 1999/040942.

In various instances, the pharmaceutical composition comprising the SIRPγ binder or SIRPγ inhibitor (e.g., an antibody or antigen binding fragment thereof) that binds to SIRPγ can further comprise, for example, micelles or liposomes, or some other encapsulated form, for prolonged storage and/or delivery effect.

Combinations

The following embodiments disclose combinations of the antigen-binding proteins (e.g., an antibody or antigen binding fragment thereof) of the present invention that bind to SIRPγ. In some embodiments the antigen-binding protein is a SIRPγ binder or a SIRPγ inhibitor (e.g., an antibody or antigen binding fragment thereof).

In various instances, the SIRPγ binder or SIRPγ inhibitor that binds to SIRPγ is administered to the subject alone, e.g., without any additional pharmaceutical actives. In various aspects, the SIRPγ binder or SIRPγ inhibitor (e.g., an antibody or antigen binding fragment thereof) that binds to SIRPγ is administered to the subject in combination with a chemotherapeutic agent. Chemotherapeutic agents suitable for use in the presently disclosed methods are known in the art, and include, but not limited to, platinum coordination compounds, topoisomerase inhibitors, antibiotics, antimitotic alkaloids and difluoronucleosides, as described in U.S. Pat. No. 6,630,124.

In some embodiments, the chemotherapeutic agent is a platinum coordination compound. The term "platinum coordination compound" refers to any tumor cell growth inhibiting compound that provides a platinum in the form of an ion. In some embodiments, the platinum coordination compound is cis-diamminediaquoplatinum (II)-ion; chloro(diethylenetriamine)-platinum(II)chloride; dichloro(ethylenediamine)-platinum(II), diammine(1,1-cyclobutanedicarboxylato) platinum(II) (carboplatin); spiroplatin; iproplatin; diammine(2-ethylmalonato)-platinum(II); ethylenediaminemalonatoplatinum(II); aqua(1,2-diaminodyclohexane)-sulfatoplatinum(II); (1,2-diaminocyclohexane)malonatoplatinum(II); (4-caroxyphthalato)(1,2-diaminocyclohexane)platinum(II); (1,2-diaminocyclohexane)-(isocitrato) platinum(II); (1,2-diaminocyclohexane)cis(pyruvato) platinum(II); (1,2-diaminocyclohexane)oxalatoplatinum(II); ormaplatin; and tetraplatin.

In some embodiments, cisplatin is the platinum coordination compound employed in the compositions and methods of the present invention. Cisplatin is commercially available under the name PLATINOL™ from Bristol Myers-Squibb Corporation and is available as a powder for constitution with water, sterile saline or other suitable vehicle. Other platinum coordination compounds suitable for use in the present invention are known and are available commercially and/or can be prepared by known techniques. Cisplatin, or cis-dichlorodiammineplatinum II, has been used successfully for many years as a chemotherapeutic agent in the treatment of various human solid malignant tumors. More recently, other diamino-platinum complexes have also shown efficacy as chemotherapeutic agents in the treatment of various human solid malignant tumors. Such diaminoplatinum complexes include, but are not limited to, spiroplatinum and carboplatinum. Although cisplatin and other diamino-platinum complexes have been widely used as chemotherapeutic agents in humans, they have had to be delivered at high dosage levels that can lead to toxicity problems such as kidney damage.

In some embodiments, the chemotherapeutic agent is a topoisomerase inhibitor. Topoisomerases are enzymes that are capable of altering DNA topology in eukaryotic cells. Topoisomerases are critical for cellular functions and cell proliferation. Generally, there are two classes of topoi- somerases in eukaryotic cells, type I and type II. Topoi- somerase I is a monomeric enzyme of approximately 100, 000 molecular weight. The enzyme binds to DNA and introduces a transient single-strand break, unwinds the double helix (or allows it to unwind), and subsequently reseals the break before dissociating from the DNA strand. Various topoisomerase inhibitors have been shown clinical efficacy in the treatment of humans afflicted with ovarian cancer, breast cancer, esophageal cancer or non-small cell lung carcinoma.

In some aspects, the topoisomerase inhibitor is camptoth- ecin or a camptothecin analog. Camptothecin is a water- insoluble, cytotoxic alkaloid produced by *Camptotheca accuminata* trees indigenous to China and *Nothapodytes foetida* trees indigenous to India. Camptothecin inhibits growth of a number of tumor cells. Compounds of the camptothecin analog class are typically specific inhibitors of DNA topoisomerase I. Compounds of the camptothecin analog class include, but are not limited to; topotecan, irinotecan and 9-amino-camptothecin.

In additional embodiments, the chemotherapeutic agent is any tumor cell growth inhibiting camptothecin analog claimed or described in: U.S. Pat. No. 5,004,758, issued on Apr. 2, 1991 and European Patent Application Number 88311366.4, published on Jun. 21, 1989 as 20' Publication Number EP 0 321 122; U.S. Pat. No. 4,604,463, issued on Aug. 5, 1986 and European Patent Application Publication Number EP 0 137 145, published on Apr. 17, 1985; U.S. Pat. No. 4,473,692, issued on Sep. 25, 1984 and European Patent Application Publication Number EP 0 074 256, published on Mar. 16, 1983; U.S. Pat. No. 4,545,880, issued on Oct. 8, 1985 and European Patent Application Publication Number EP 0 074 256, published on Mar. 16, 1983; European Patent Application Publication Number EP 0 088 642, published on Sep. 14, 1983; Wani et al., J. Med. Chem., 29, 2358-2363 (1986); Nitta et al., Proc. 14th International Congr. Chemo- therapy, Kyoto, 1985, Tokyo Press, Anticancer Section 1, p. 28-30, especially a compound called CPT-11. CPT-11 is a camptothecin analog with a 4-(piperidino)-piperidine side chain joined through a carbamate linkage at C-10 of 10-hy- droxy-7-ethyl camptothecin. CPT-11 is currently undergoing human clinical trials and is also referred to as irinotecan; Wani et al, J. Med. Chem., 23, 554 (1980); Wani et. al., J. Med. Chem., 30, 1774 (1987); U.S. Pat. No. 4,342,776, issued on Aug. 3, 1982; U.S. patent application Ser. No. 581,916, filed on Sep. 13, 1990 and European Patent Appli- cation Publication Number EP 418 099, published on Mar. 20, 1991; U.S. Pat. No. 4,513,138, issued on Apr. 23, 1985 and European Patent Application Publication Number EP 0 074 770, published on Mar. 23, 1983; U.S. Pat. No. 4,399, 276, issued on Aug. 16, 1983 and European Patent Appli- cation Publication Number 0 056 692, published on Jul. 28, 1982; the entire disclosure of each of which is hereby incorporated by reference. All of the above-listed com- pounds of the camptothecin analog class are available com- mercially and/or can be prepared by known techniques including those described in the above-listed references. The topoisomerase inhibitor may be selected from the group consisting of topotecan, irinotecan and 9-aminocamptoth- ecin.

The preparation of numerous compounds of the camp- tothecin analog class (including pharmaceutically acceptable salts, hydrates and solvates thereof) as well as the preparation of oral and parenteral pharmaceutical composi- tions comprising such a compounds of the camptothecin analog class and an inert, pharmaceutically acceptable car- rier or diluent, is extensively described in U.S. Pat. No. 5,004,758, issued on Apr. 2, 1991 and European Patent Application Number 88311366.4, published on Jun. 21, 1989 as Publication Number EP 0 321 122, the teachings of which are incorporated herein by reference.

In still yet other embodiments, the chemotherapeutic agent is an antibiotic compound. Suitable antibiotics include, but are not limited to, doxorubicin, mitomycin, bleomycin, daunorubicin and streptozocin.

In some embodiments, the chemotherapeutic agent is an antimitotic alkaloid. In general, antimitotic alkaloids can be extracted from *Cantharanthus roseus*, and have been shown to be efficacious as anticancer chemotherapy agents. A great number of semi-synthetic derivatives have been studied both chemically and pharmacologically (see, O. Van Tellingen et al, Anticancer Research, 12, 1699-1716 (1992)). The anti- mitotic alkaloids of the present invention include, but are not limited to, vinblastine, vincristine, vindesine, paclitaxel (PTX; Taxol®) and vinorelbine. The latter two antimitotic alkaloids are commercially available from Eli Lilly and Company, and Pierre Fabre Laboratories, respectively (see, U.S. Pat. No. 5,620,985). In an exemplary aspect of the present invention, the antimitotic alkaloid is vinorelbine.

In other embodiments of the invention, the chemothera- peutic agent is a difluoronucleoside. 2'-deoxy-2',2'-difluoro- nucleosides are known in the art as having antiviral activity. Such compounds are disclosed and taught in U.S. Pat. Nos. 4,526,988 and 4,808,614. European Patent Application Pub- lication 184,365 discloses that these same difluoronucleo- sides have oncolytic activity. In certain specific aspects, the 2'-deoxy-2',2'-difluoronucleoside used in the compositions and methods of the present invention is 2'-deoxy-2',2'- difluorocytidine hydrochloride, also known as gemcitabine hydrochloride. Gemcitabine is commercially available or can be synthesized in a multi-step process as disclosed and taught in U.S. Pat. Nos. 4,526,988, 4,808,614 and 5,223,608, the teachings of which are incorporated herein by reference.

In exemplary aspects, the chemotherapeutic agent is a hormone therapy agent. In exemplary instances, the hor- mone therapy agent is, for instance, letrozole, tamoxifen, bazedoxifene, exemestane, leuprolide, goserelin, fulves- trant, anastrozole, or toremifene. In exemplary aspects, the hormone therapy agent is a luteinizing hormone (LH) blocker, e.g., gosarelin, or an LH releasing hormone (RH) agonist. In exemplary aspects, the hormone therapy agent is an ER-targeted agent (e.g., fulvestrant or tamoxifen), rapamycin, a rapamycin analog (e.g., everolimus, temsiro- limus, ridaforolimus, zotarolimus, and 32-deoxo-rapamy- cin), an anti-HER2 drug (e.g., trastuzumab, pertuzumab, lapatinib, T-DM1, or neratinib) or a PI3K inhibitor (e.g., taselisib, alpelisib or buparlisib).

In exemplary aspects, the chemotherapeutic agent is a CDK4/6 inhibitor such as palbociclib, ribociclib, or abe- maciclib (see, e.g., Knudsen and Witkiewicz, Trends Cancer 3(1): 39-55 (2017)).

Subjects

In exemplary embodiments of the present disclosure, the subject is a mammal, including, but not limited to, mammals of the order Rodentia, such as mice and hamsters, and mammals of the order Logomorpha, such as rabbits, mam- mals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human.

In exemplary aspects, the subject has cancer or a tumor. The cancer in some aspects is one selected from the group consisting of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma. In particular embodiments, the tumor is non-small cell lung cancer (NSCLC), head and neck cancer, renal cancer, triple negative breast cancer, or gastric cancer. In exemplary aspects, the subject has a tumor (e.g., a solid tumor, a hematological malignancy, or a lymphoid malignancy) and the pharmaceutical composition is administered to the subject in an amount effective to treat the tumor in the subject. In other exemplary aspects, the tumor is non-small cell lung cancer (NSCLC), small cell lung cancer (SCLC), head and neck cancer, renal cancer, breast cancer, melanoma, ovarian cancer, liver cancer, pancreatic cancer, colon cancer, prostate cancer, gastric cancer, lymphoma or leukemia, and the pharmaceutical composition is administered to the subject in an amount effective to treat the tumor in the subject.

Optionally, the subject has hepatocellular carcinoma (HCC), colorectal cancer (CRC), lung cancer, optionally, non-small-cell lung cancer (NSCLC).

Relief of Immune Suppression and Enhancement of Immune Response

Without being bound to any particular theory, the antigen-binding protein (e.g., an antibody or antigen binding fragment thereof) that binds to SIRPγ described herein is useful for increasing effector activity or reducing suppressive activity of T-cells. In some embodiments, the antigen-binding protein is a SIRPγ binder or SIRPγ inhibitor. Also, it is postulated that the SIRPγ binders or SIRPγ inhibitors (e.g., an antibody or antigen binding fragment thereof) that bind to SIRPγ described herein are useful for increasing an immune response against a tumor or cancer. Accordingly, the present disclosure provides methods of increasing effector activity or reducing suppressive activity of T-cells in a subject with a tumor or cancer. In exemplary embodiments, the method comprises administering to the subject an antigen-binding protein (e.g., an antibody or antigen binding fragment thereof) that binds to SIRPγ in an amount effective to increase the effector activity or reduce the suppressive activity in the subject. In some embodiments, the antigen-binding protein is a SIRPγ binder or SIRPγ inhibitor. Also, the present disclosure accordingly provides methods of increasing an immune response against a tumor or cancer in a subject. In exemplary embodiments, the method comprises administering to the subject a SIRPγ binder or SIRPγ inhibitor (e.g., an antibody or antigen binding fragment thereof) that binds to SIRPγ in an amount effective to increase an immune response against a tumor or cancer.

The increase in effector activity of T-cells provided by the methods of the present disclosure may be at least or about a 1% to about a 10% increase (e.g., at least or about a 1% increase, at least or about a 2% increase, at least or about a 3% increase, at least or about a 4% increase, at least or about a 5% increase, at least or about a 6% increase, at least or about a 7% increase, at least or about a 8% increase, at least or about a 9% increase, at least or about a 9.5% increase, at least or about a 9.8% increase, at least or about a 10% increase) relative to a control. The increase in effector activity of T-cells provided by the methods of the present disclosure may be at least or about a 10% to greater than about a 95% increase (e.g., at least or about a 10% increase, at least or about a 20% increase, at least or about a 30% increase, at least or about a 40% increase, at least or about a 50% increase, at least or about a 60% increase, at least or about a 70% increase, at least or about a 80% increase, at least or about a 90% increase, at least or about a 95% increase, at least or about a 98% increase, at least or about a 99% increase, or about a 100% increase) relative to a control. In exemplary aspects, the control is cancer or tumor or a subject or a population of subjects that was not treated with the presently disclosed SIRPγ binder or SIRPγ inhibitor (e.g., an antibody or antigen binding fragment thereof) that binds to SIRPγ or wherein the subject or population of subjects was treated with a placebo.

The increase in an immune response against a tumor or cancer provided by the methods of the present disclosure may be at least or about a 1% to about a 10% increase (e.g., at least or about a 1% increase, at least or about a 2% increase, at least or about a 3% increase, at least or about a 4% increase, at least or about a 5% increase, at least or about a 6% increase, at least or about a 7% increase, at least or about a 8% increase, at least or about a 9% increase, at least or about a 9.5% increase, at least or about a 9.8% increase, at least or about a 10% increase) relative to a control. The increase in an immune response against a tumor or cancer provided by the methods of the present disclosure may be at least or about a 10% to greater than about a 95% increase (e.g., at least or about a 10% increase, at least or about a 20% increase, at least or about a 30% increase, at least or about a 40% increase, at least or about a 50% increase, at least or about a 60% increase, at least or about a 70% increase, at least or about a 80% increase, at least or about a 90% increase, at least or about a 95% increase, at least or about a 98% increase, at least or about a 99% increase, or about a 100% increase) relative to a control. In exemplary aspects, the control is cancer or tumor or a subject or a population of subjects that was not treated with the presently disclosed SIRPγ binder or SIRPγ inhibitor (e.g., an antibody or antigen binding fragment thereof) that binds to SIRPγ or wherein the subject or population of subjects was treated with a placebo.

The reduction in suppressive activity of T-cells provided by the methods of the present disclosure may be at least or about a 1% to about a 10% reduction (e.g., at least or about a 1% reduction, at least or about a 2% reduction, at least or about a 3% reduction, at least or about a 4% reduction, at least or about a 5% reduction, at least or about a 6% reduction, at least or about a 7% reduction, at least or about a 8% reduction, at least or about a 9% reduction, at least or about a 9.5% reduction, at least or about a 9.8% reduction, at least or about a 10% reduction) relative to a control. The reduction in suppressive activity of T-cells provided by the methods of the present disclosure may be at least or about a 10% to greater than a 95% reduction (e.g., at least or about a 10% reduction, at least or about a 20% reduction, at least or about a 30% reduction, at least or about a 40% reduction, at least or about a 50% reduction, at least or about a 60% reduction, at least or about a 70% reduction, at least or about a 80% reduction, at least or about a 90% reduction, at least or about a 95% reduction, at least or about a 98% reduction, at least or about a 99% reduction, or about a 100% reduction) relative to a control. In exemplary aspects, the control is cancer or tumor or a subject or a population of subjects that was not treated with the presently disclosed SIRPγ binder or SIRPγ inhibitor (e.g., an antibody or antigen binding fragment thereof) that binds to SIRPγ or wherein the subject or population of subjects was treated with a placebo.

With regard to the methods of increasing effector activity or reducing suppressive activity of T-cells, the T-cells in various aspects are located within a tumor or a tumor microenvironment, optionally, the T-cells are tumor-infiltrating T-cells. In some aspects, the T-cells are T regulatory cells (Tregs). In various aspects, the T-cells are exhausted T-cells, optionally, exhausted CD8+ T-cells. In certain instances, the T-cells are memory cells, optionally, the memory cells are CD8+ memory cells or CD4+ central memory cells.

With regard to the methods of increasing an immune response against a tumor or cancer, the immune-response is mediated by T-cells in various aspects. Optionally, the T-cells are located within a tumor or a tumor microenvironment. In various instances, the T-cells are tumor-infiltrating T-cells. In some aspects, the T-cells are T regulatory cells (Tregs). In various aspects, the T-cells are exhausted T-cells, optionally, exhausted CD8+ T-cells. In certain instances, the T-cells are memory cells, optionally, the memory cells are CD8+ memory cells or CD4+ central memory cells.

In exemplary aspects, the subject of the presently disclosed method of increasing effector activity or reducing suppressive activity of T-cells or the presently disclosed method of increasing an immune response against a tumor or cancer the immune-response is a subject as described herein. In various aspects, the subject has a tumor or a cancer. Optionally, the subject has hepatocellular carcinoma (HCC), colorectal cancer (CRC), lung cancer, optionally, non-small-cell lung cancer (NSCLC), or breast cancer.

Without being bound to any particular theory, increased effector activity or reduced suppressive activity of T-cells and/or increased immune responses against a tumor or cancer in a subject lead to treatment of a tumor or cancer in the subject. Accordingly, the present disclosure additionally provides methods of treating a subject with a tumor or cancer. In exemplary embodiments, the method comprises increasing effector activity or reducing suppressive activity of T-cells in the subject and/or increasing an immune response against the tumor or cancer in the subject. The considerations and details of the above-described methods of treatment comprising administering to the subject a SIRPγ binder or SIRPγ inhibitor (e.g., an antibody or antigen binding fragment thereof) that binds to SIRPγ apply to the instantly-described methods of treatment (comprising increasing effector activity or reducing suppressive activity of T-cells in the subject and/or increasing an immune response against the tumor or cancer in the subject).

The following examples are given merely to illustrate the present invention and not in anyway to limit its scope.

EXAMPLES

The studies described below confirm the T cell specific expression pattern of SIRPγ in humans. Although most of T cells express SIRPγ highly, interestingly, memory CD8 T cells and tumor infiltrated CD8 exhaustion cells showed a heightened expression of SIRPγ compared to other T cells. Previous studies on the characterization of CD8 TILs from breast tumor and melanoma tumor tissues suggest that tumor CD8 TILs are predominantly effector memory cells. The high SIRPγ expression pattern on both memory and exhaustion T cells suggest that SIRPγ may negatively impact T cell effector function within tumor environment. Interestingly, the in vitro functional data herein is consistent with this hypothesis and confirms that SIRPγ is a negative regulator of T cell effector function. Furthermore, SIRPγ enhanced Treg suppressive function. These data provide insight into potential therapeutic intervention by targeting SIRPγ on both T cells and Tregs to improve immune response against tumors.

Example 1

The following example describes the materials and methods used in the Examples.

Cell preparation and MACS bead sorting: PBMC were isolated from blood samples from healthy donors using Ficoll Hypaque (GE Healthcare Biosciences, Pittsburgh, PA) density gradient. PanT and CD8 T cells were isolated from PBMCs using Miltenyi microbead negative selection kits (#130-096-535 and 130-096-495, Miltenyi) according to manufacturer instructions. To isolate human regulatory T cells, CD4+ T cells were isolated from PBMCs using the Human CD4+ T Cell Isolation kit (130-096-533, Miltenyi) followed by enrichment of CD25+ T cells with CD25 microbeads (130-092-983, Miltenyi) according to the manufacturer's protocol. Finally, CD4+CD25+CD127-human regulatory T cells were FACS sorted. Sorted panT, CD8 and Treg cells were subjected to downstream function assays.

In vitro induction of CD8 exhaustion: Purified human CD8 T cells were seeded at $1-2 \times 10^6$ cells/ml and subjected to anti-CD3 (UCHT1, 0.2 μg/ml, BD Biosciences) and anti-CD28 (CD28.2, 2 μg/ml, BD Biosciences) stimulation for 3-4 days. CD8 T cells were re-stimulated every 3-4 days with anti-CD3 (UCHT1, 1 μg/ml, BD Biosciences) and anti-CD28 (CD28.2, 2 μg/ml, BD Biosciences). Cells were subjected to the re-stimulation at least two rounds as described above.

Flow cytometric antibody staining: Anti-human antibodies used for multi-color flow cytometric analysis included: CD3 (Biolegend, 344804), CD4 (Biolegend, 300520), CD8 (Biolegend, 301040), SIRPγ (Biolegend, 336606), mouse IgG1 K isotype control (Biolegend, 400112), CD14 (BD Biosciences, 558121), CD56 (Biolegend, 318321), CD45RA (Biolegend, 304112), CCR7 (Biolegend, 353232), CD127 (Biolegend, 351318), Foxp3 (Biolegend, 320214). PBMC samples were washed with MACS buffer and stained with fluorescently labeled anti-human antibodies. For Foxp3 intracellular staining, cells were fixed with intracellular fixation and permeabilization buffer set (eBioscience, 00-5523-00) and stained with Foxp3 antibody. Flow cytometric data were acquired on LSRII using FACSDiva software (Becton Dickinson). Data were analyzed using Flow Jo (TreeStar, Ashland, OR).

SIRPγ overexpression, T cell re-stimulation and cytokine detection: To overexpress human SIRPγ in human T cells, human SIRPγ was cloned into MSCV-IRES-EGFP retroviral vector. Retrovirus was generated by using pAmpho packaging system (Clontech, #631530) before infecting T cells. For T cell infection, pan T cells were isolated from human PBMCs by using human PanT cell isolation kit from Miltenyi and activated with Dynabeads Human T-Activator CD3/CD28 (ThermoFisher Scientific, #11131D) at 1:1 ratio for 72 hours. 72 hours later, Dynabeads were removed and activated T cells were spin-infected with retrovirus at 2000 rpm for 1 hour under 32 degrees.

D5 post retrovirus spin-infection, GFP+ human SIRPγ overexpressing T cells were FACS sorted and rested with human IL2 for 2 days. Equal numbers of control or human SIRPγ overexpressing CD8 or CD4 T cells were seeded into 96 round-bottom wells and re-stimulated with plate-bound anti-CD3 (0.5 μg/ml) and anti-CD28 (1 μg/ml) (eBioscience 16-0037-85 and 16-0289-85). Cell supernatant was collected 24 hours after re-stimulation and human IFNγ was measured by ELISA (eBioscience, 88-7316-88).

CRISPR knockout in naïve T cells: For CRISPR knockout in naïve T cells, crRNA-tracrRNA duplex was prepared by mixing equimolar concentrations of Alt-R crRNA and Alt-R tracrRNA (IDT) oligos. Mixed oligos were annealed by heating at 95° C. for 5 min in PCR thermocycler and the mix was slowly cooled to room temperature. Three crRNA-tracrRNA duplexes (3 μl equal to 150 pmol each, total of 9 μl) and 6 μl (equal to 180 pmol) TrueCut Cas9 Protein v2 (catalog number A36499; Thermo Fisher Scientific, 5 μg/ml) were gently mix by pipetting up and down and incubated at room temperature for 10-20 min. 200 μl complete T cell media per well of a 96-well plate was prewarmed. 1-2 million T cells were resuspended in 20 μl primary cell nucleofection solution (P2 Primary Cell 4D-Nucleofector X kit S [32 RCT, V4XP-2032; Lonza]). T cells were mixed and incubated with 15 μl RNP at room temperature for 2 min in round bottom 96-well plate. The cell/RNP mix was transferred to Nucleofection cuvette strips (4D-Nucleofector X kit S; Lonza). Cells were electroporated using a 4D nucleofector. Pulse for human naive T cell populations is EH100. After nucleofection, prewarmed T cell media was used to transfer transfected cells in 96-well plates. Resting human T cells were cultured at 1×106 per well in 200 μl complete T cell media for 3-5 d (with IL2 and IL7). Knockdown were checked by FACS at D5 post electroporation. The following crRNA targeting sequences were used in the study: SIRPγ-crRNA1: 5'-

```
SIRPγ-crRNA1:
                                    (SEQ ID NO: 7)
5'-GGGACCCGTCCTGTGGTTCAG-3',

SIRPγ-crRNA2:
                                    (SEQ ID NO: 8)
5'-AAAAGGGAGCCCTGAGAACG-3',

SIRPγ-crRNA3:
                                    (SEQ ID NO: 9)
5'-GTATGTGCCGACATCTGCTG-3',

CD47-crRNA1:
                                    (SEQ ID NO: 10)
5'-TACGTAAAGTGGAAATTTAA-3',

CD47-crRNA2:
                                    (SEQ ID NO: 11)
5'-TTTGCACTACTAAAGTCAGT-3',
```

```
                            -continued
CD47-crRNA3:
                                    (SEQ ID NO: 12)
5'-TCCATATTAGTAACAAAGCA-3', PD1-crRNA1:
                                    (SEQ ID NO: 13)
5'-GCAGTTGTGTGACACGGAAG-3', PD1-crRNA2:
                                    (SEQ ID NO: 14)
5'-GGGCCCTGACCACGCTCATG-3', PD1-crRNA3:
                                    (SEQ ID NO: 15)
5'-GATCTGCGCCTTGGGGGCCA-3'.
```

CRISPR knockout in activated T cells and Jurkat T cells: Human panT cells were activated with Dynabeads Human T-Activator CD3/CD28 (ThermoFisher Scientific, #11131D) at 1:1 ratio for 48 hours. 48 hours later, Dynabeads were removed and 100,000-200,000 activated T cells were resuspended in 20 μl primary cell nucleofection solution (P2 Primary Cell 4D-Nucleofector X kit S [32 RCT, V4XP-2032; Lonza]) and mixed with RNP complex. The cell/RNP mix was transferred to Nucleofection cuvette strips (4D-Nucleofector X kit S; Lonza). Cells were electroporated using a 4D nucleofector. Pulse for human activated T cell populations is CM138. After nucleofection, prewarmed T cell media was used to transfer transfected cells in 96-well plates. Human T cells were cultured at 1×105 per well in 200 μl complete T cell media (with IL2). Knockdown were checked by FACS at D2 post electroporation.

For Jurkat T cell knockout, 200,000 Jurkat T cells were resuspended in 20 μl primary cell nucleofection solution (P4 Primary Cell 4D-Nucleofector X kit S [32 RCT, V4XP-4032; Lonza]) and mixed with RNP complex. The cell/RNP mix was transferred to Nucleofection cuvette strips (4D-Nucleofector X kit S; Lonza). Cells were electroporated using a 4D nucleofector with CM138 program. D3 post electroporation, knockout T cells were FACS sorted based on the protein expression on cell surface and further expanded for future experiments.

Re-stimulation of knockout Tcells: D3 post CRISPR knockout, T cells were restimulated and SIRPγ-CD4 or CD8 T cells were FACS sorted D4 post CRISPR knockout. Sorted SIRPγ knockout T cells were rested with human IL2 for 2 days. Equal numbers of control or human SIRPγ knockout CD8 or CD4 T cells were seeded into 96 round-bottom wells and re-stimulated with plate-bound anti-CD3 (0.5 μg/ml) and anti-CD28 (1 μg/ml). Cell supernatant was collected 24 hours after re-stimulation and human IFNγ was measured by ELISA.

Real time PCR: For qRT-PCR, total RNA was isolated from sorted and restimulated control or SIRPγ-T cells 9 days after CRISPR/Cas9 delivery using RNeasy Mini kit (Qiagen) following the manufacturer's instruction. cDNA was reverse transcribed from these RNAs using SuperScript IV First-Strand Synthesis System (#18091050, Invitrogen) and qRT-PCR was done with QuantStudio3 (Applied Biosystems) using TaqMan gene expression assay kit/probe sets (Thermo Scientific). The primers used in this study were as follows: GAPDH: Hs03929097_g1, SIRPγ F:5'-AGGT-GAGGAGGAGCTACAGA-3' (SEQ ID NO: 16), SIRPγ R:5'-GGTCCAACTCCTCTGAACCA-3' (SEQ ID NO: 17), SIRPγ probe:5'-CCCTGCTTCCCGTGGGACCCG-3' (SEQ ID NO: 18). SIRPγ expressions between samples were normalized to GAPDH.

PCR amplification and analysis of target region: Genomic DNAs were isolated from sorted and restimulated control or SIRPγ-T cells 9 days after CRISPR/Cas9 delivery using using Qiagen DNeasy Blood & Tissue kit (Qiagen) following the manufacturer's instruction. Genomic regions, containing the SIRPγ target site, were PCR-amplified using the following primers: SIRPγ F:5'-CCAGATTGG-GAAGGACAAGAGCTGT-3' (SEQ ID NO: 19), SIRPγ R:5'-GGCATGTTGTGAGGGTTAAATGAGA-3'(SEQ ID NO: 20). PCR products were analyzed through gel electrophoresis or purified on 2% (wt/vol) agarose gel containing SYBR Safe (Life Technologies) by using Qiagen Gel Extraction kit and subjected to sanger sequencing.

SIRPγ expression on Treg cells and Treg suppression assay: To overexpress human SIRPγ in human T regulatory cells, FACS sorted CD4+CD25+CD127-Treg cells were activated with Dynabeads Human T-Activator CD3/CD28 (ThermoFisher Scientific, #11131D) at 1:1 ratio for 48 hours in the presence of 200 U/ml human IL2 (202-IL-010/CF, R&D). 48 hours later, Dynabeads were removed and activated Treg cells were spin-infected with retrovirus at 2000 rpm for 1 hour under 32 degree. D5 post retrovirus spin-infection, GFP+ human SIRPγ overexpressing Treg cells were FACS sorted and rested with human IL2 for overnight before setting up the suppression assay.

To set up the suppression assay, responder CD4 T cells were isolated from a different healthy donor PBMCs by using naïve CD4 T cell isolation kit (130-094-131, Miltenyi) and isolated CD4 T cells were labelled by cell trace violet proliferation kit (C34557, Thermo Fisher). Rested Treg cells were mixed with CTV labelled responder CD4 T cells at different ratio. Allogenic DCs were added to the reaction and CD4 T cells proliferation was measured by CTV dilution.

Mixed lymphocyte reaction and T cell proliferation assay: D6 post CRISPR knockdown, T cells were subjected to mixed lymphocyte reactions (MLRs) or TCR stimulated proliferation. MLRs were performed by incubating 100,000 pan T cells from a healthy donor (responder) with 10,000 allogeneic DCs (stimulators). T-cell proliferation was measured by standard 3H thymidine incorporation assay on D7.

For TCR stimulation, isolated T cells or CRISPR knockout T cells were plated on serial dilution of mAb anti-CD3 (OKT3, eBioscience) precoated 96 well roundbottom plate. Anti-CD47 mAb (B6H12), anti-SIRPγ (LSB2.20), or control mouse IgG was added to T-cell cultures as indicated. After 72 hours, T-cell proliferation was measured by standard 3H-thymidine incorporation assay.

SIRP-IgG fusion proteins: Extracellular domain of SIRPγ and SIRPα were amplified by PCR and cloned into pTT5.2-CMV vector in frame with a cDNA fragment encoding the Fc portion of human IgG fusion proteins. SIRPγ and SIRPα chimeric cDNAs were transiently expressed in 293 cells and secreted SIRP-IgG fusion proteins were purified from culture supernatant on protein A.

Binding assay: SIRPγ and SIRPα-IgG FC proteins (5 μg/mL) were incubated with various cells for 1 hour at 4° C. in the absence of presence of antibodies against SIRPγ and CD47. Then cells were washed with FACS staining buffer twice and stained with anti-IgG-FC (PE) antibody (1:50) for 15 minutes at 4 degree. After two washes, binding of fusion proteins to cells was detected by flow cytometry using a PE conjugated anti-human IgG-Fc (#409304, Biolegend) followed by FACS analyses.

In vitro antibody interfering assay: SIRPγ antibodies (10 μg/mL) were incubated with Jurkat cells for 30 minutes at room temperature. Cells were washed with FACS staining buffer and incubated with SIRPγ-Fc fusion proteins (10 μg/mL) for 30 minutes at 4° C. Then cells were washed with FACS staining buffer twice and stained with anti-IgG-Fc (PE) antibody (#409304, Biolegend, 1:50) for 15 minutes at 4 degree. After two washes, binding of fusion proteins to cells was detected by flow cytometry followed by FACS analyses.

Antibody crosslinking and T cell proliferation assay: 96 well plates were coated with 1 Ogg/mL SIRPγ antibodies (50 μl/well) overnight at 4°. The next day, pan T cells from healthy donors were plated in the wells and T cells were stimulated with IMMUNOCULT™ Human CD3/CD28 T Cell Activator (#10971, Stemcell Technologies). T-cell proliferation was measured by standard 3H thymidine incorporation assay on D3. Cell culture supernatant was collected and subjected to Cytometric Bead Array (CBA) (#558269, BD Biosciences) analyses.

Statistical analysis: Statistical significance was determined by performing t test with Graphpad Prism. Significance is denoted as *p≤0.0002, p≤0.0021, *p≤0.0332, and ns p>0.05.

Example 2

This example demonstrates that SIRPγ is highly expressed on T cells.

Figure 1B:
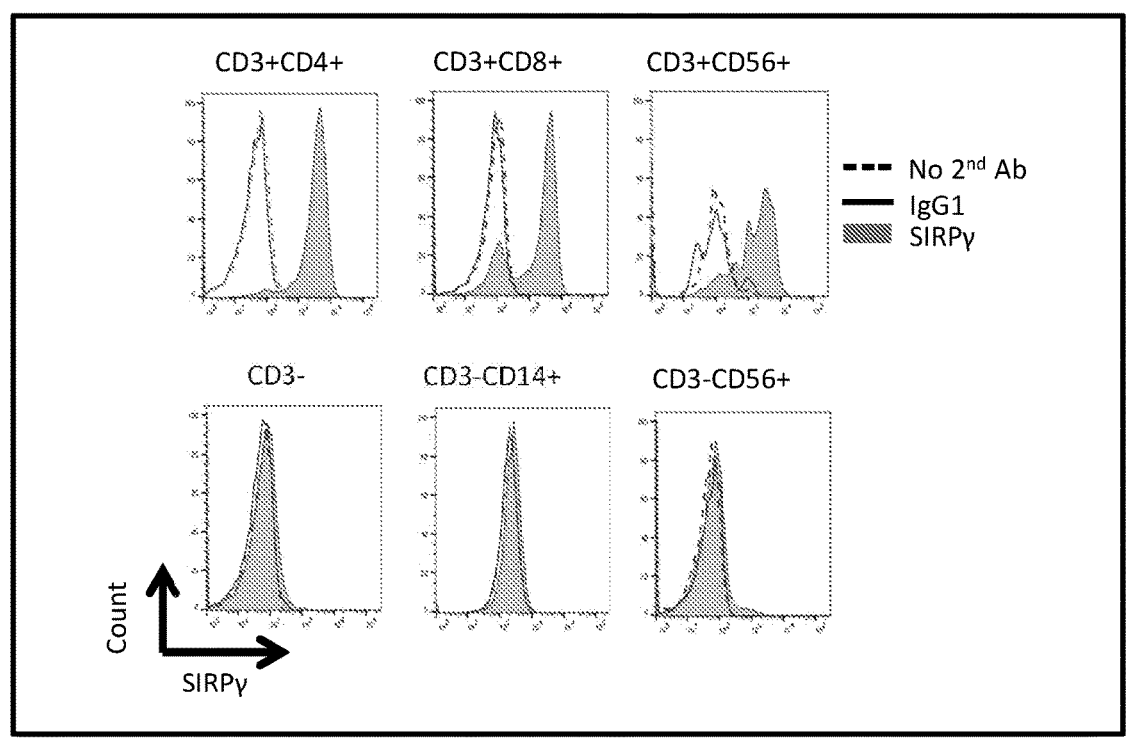

To study the function of SIRPγ in T cells, the expression profile of SIRPγ was first examined in immune cell populations. The specificity of SIRPγ antibody was confirmed by specific recognition of overexpressed SIRPγ protein on cell surface of 293T cells (FIG. 1A). Cell surface staining of SIRPγ on human PBMC cells showed that SIRPγ is mainly expressed on CD4⁺ and CD8⁺ T cells, but not on CD14⁺ monocytes (FIG. 1B). SIRPγ showed high level of expression in both human CD4 and CD8 T cells at the resting stage. Natural Killer T (NKT) cells also showed positive SIRPγ expression on cell surface. This data is consistent with previous studies (Piccio et al., Blood, 105:2421-2427 (2005)), indicating that the expression of SIRPγ is T cell specific.

Figure 1C:
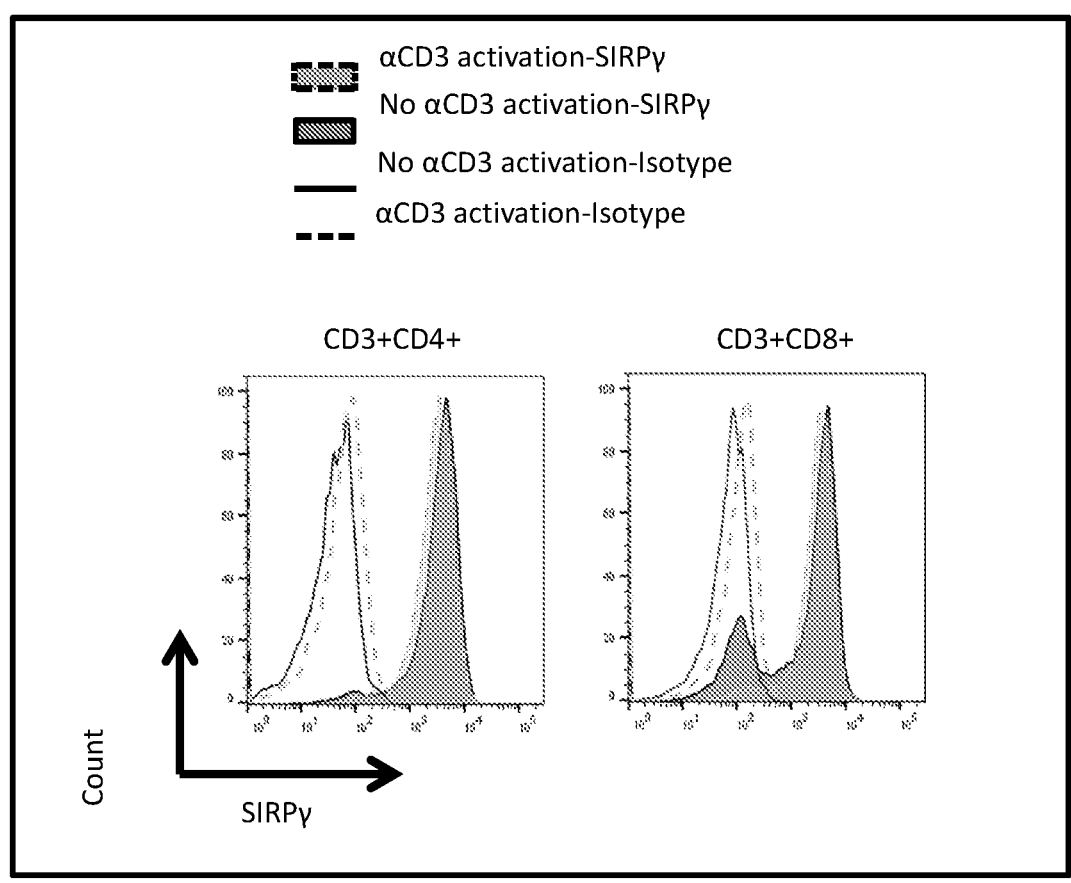

Previous studies (Piccio et al., Blood, 105:2421-2427 (2005)) have shown that SIRPγ receptor ligation by anti-SIRPγ antibody functions as a co-stimulatory factor for T cell proliferation, suggesting a potential interplay between SIRPγ and the T cell receptor (TCR). To test if SIRPγ expression is regulated by TCR signaling, T cells were stimulated with anti-CD3 and anti-CD28 antibodies and the expression level of SIRPγ by the stimulated T cells was examined. SIRPγ maintained a high expression level on T cells and its expression level was not changed during TCR stimulation (FIG. 1C).

Example 3

This example demonstrates that SIRPγ has heightened expression on memory T cells and tumor infiltrated exhausted T cells.

Figure 2A:
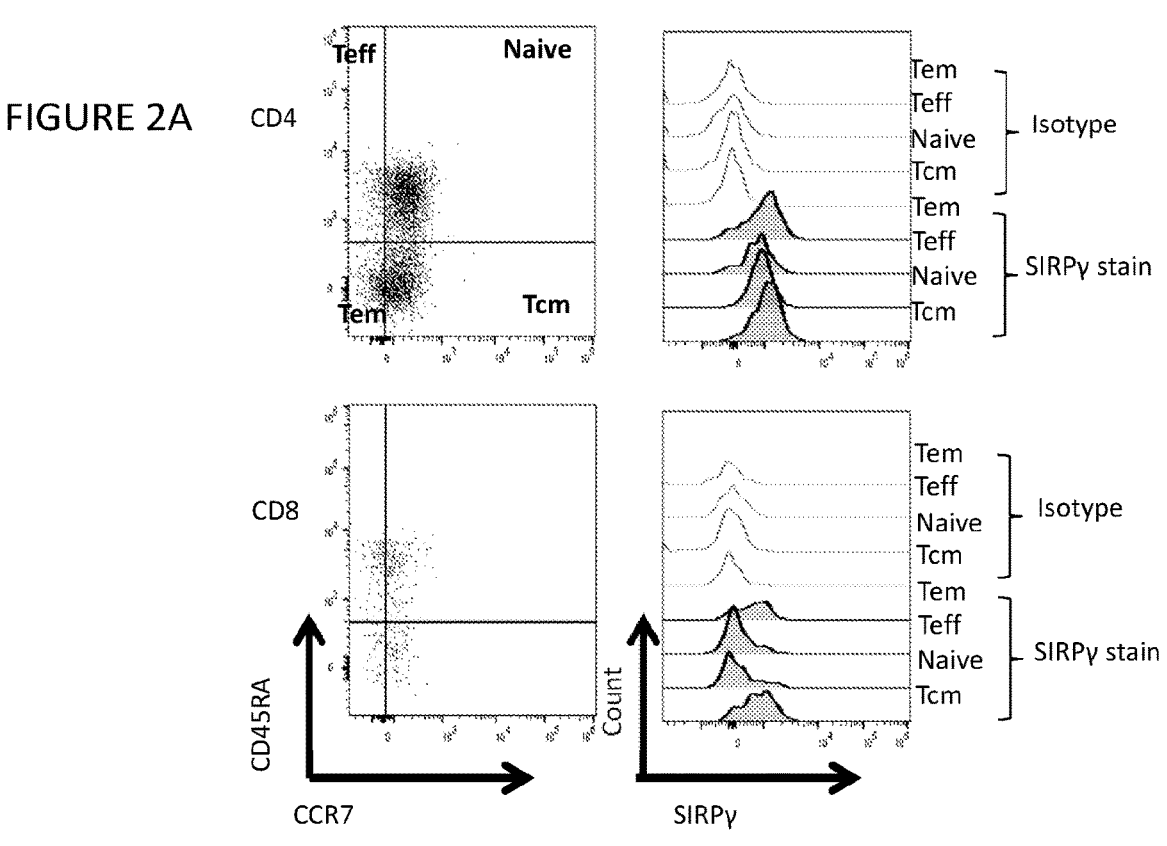
FIGS. 2A and 2B demonstrate that SIRPγ is highly expressed on memory T cells.
Figure 2B:
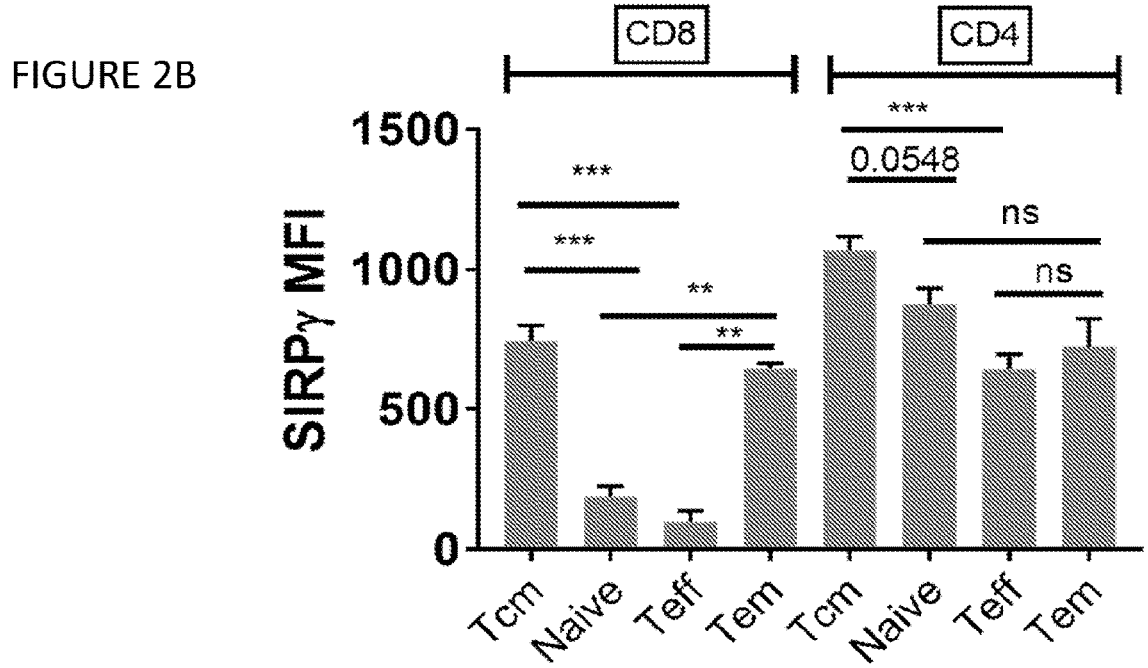

To further understand the expression profiling of SIRPγ in subsets of memory and effector T cells, T cells from multiple healthy donor PBMCs were stained using antibodies. Naïve T cells, central memory, effector memory and effector T cells were identified by CD45RA and CCR7 staining. CD8+ memory T cells demonstrated a significantly heightened expression of SIRPγ compared to effector T cells and naïve T cells (FIGS. 2A and 2B). Within CD4 T cell population, central memory CD4 T cells demonstrated a higher expression of SIRPγ, than effector T cells (FIGS. 2A and 2B). These data suggest that SIRPγ may contribute to the memory function of T cells during immune regulation.

Figure 3A:
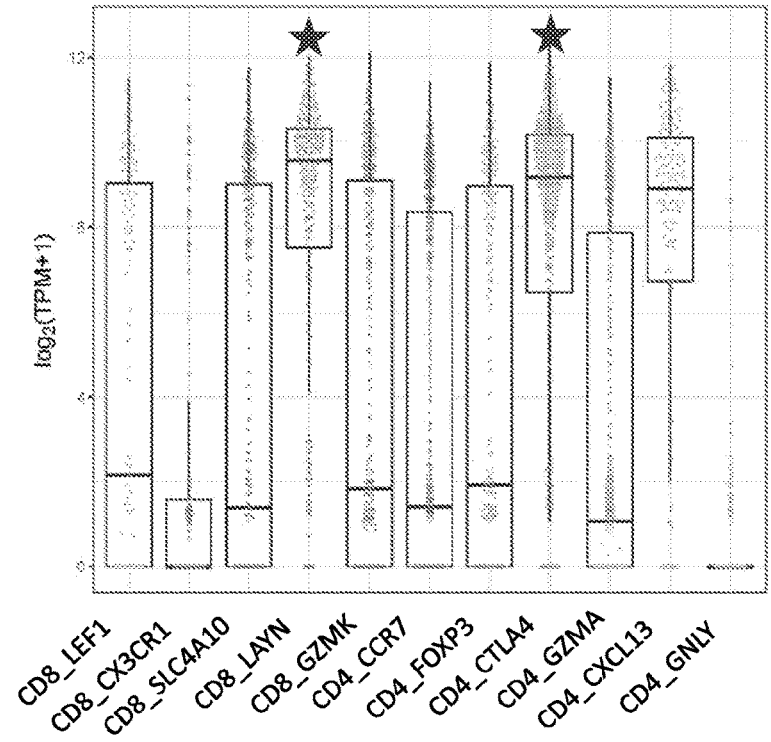
FIGS. 3A-3C demonstrate that SIRPγ has heightened expression on tumor infiltrated exhaustion T cells.
Figure 3B:
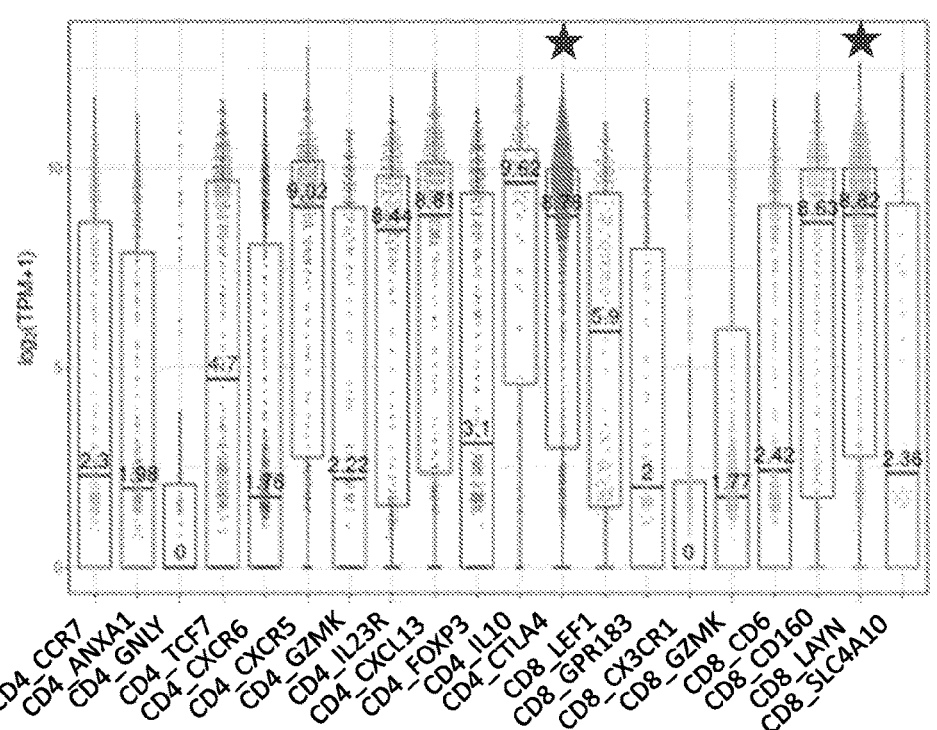
Figure 3C:
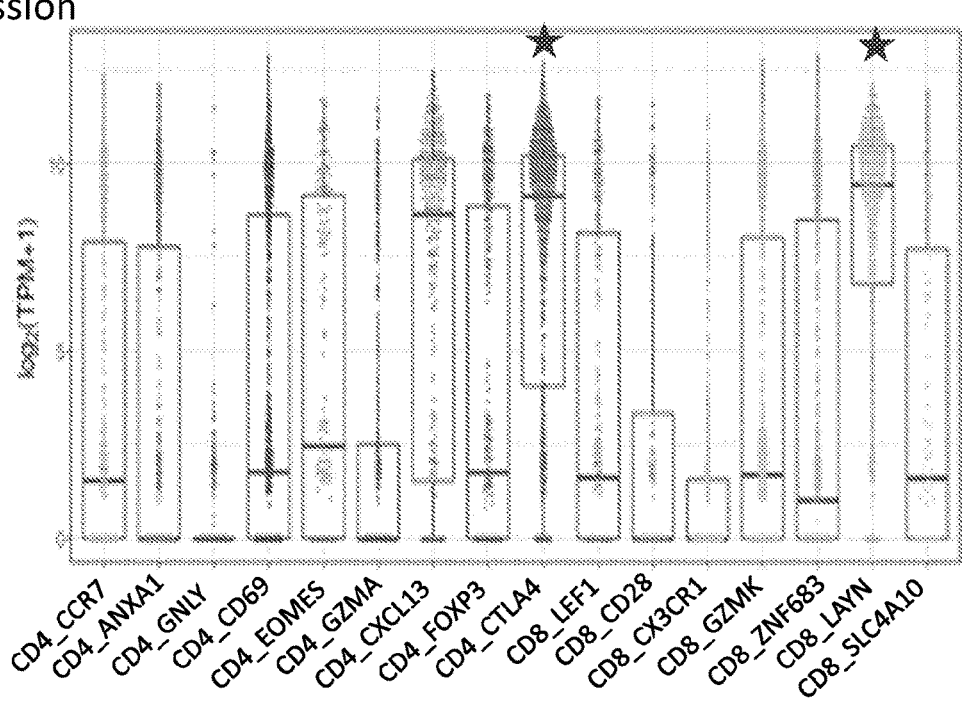
Figure 4:
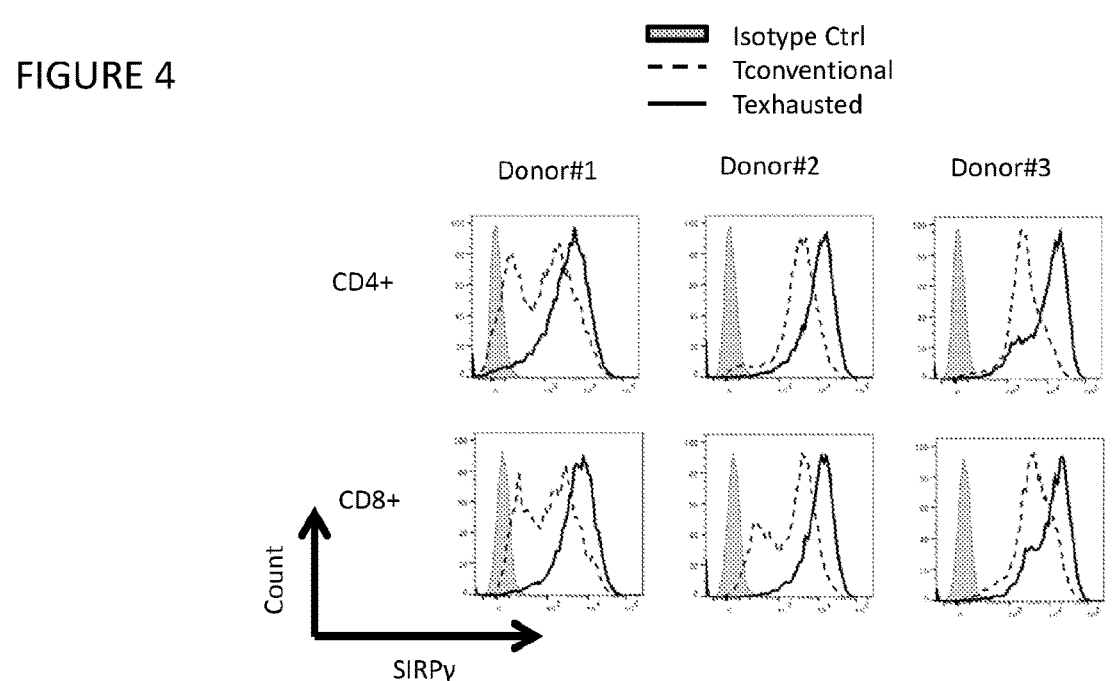
FIG. 4 demonstrates that SIRPγ has heightened expression on exhausted T cells derived from repeated TCR re-stimulation.

Interestingly, single-cell RNA sequencing profiling of tumor infiltrated T cells showed that SIRPγ is highly expressed in exhausted CD8 T cells and tumor Tregs isolated from different type of human cancers including HCC, CRC and lung cancer (FIGS. 3A-3C). Because the association of SIRPγ with tumor-infiltrating exhausted CD8+ T cells in tumors was not previously reported, its expression and regulation on in vitro derived exhausted CD8+ T cells was further characterized. The SIRPγ protein expression was increased on CD8+ T cells that were repeatedly in vitro stimulated with low dose of αCD3 TCR activation, a condition which mimics T cell exhaustion (FIG. 4). The heightened expression pattern of SIRPγ in exhausted T cells is correlated with decreased effector cytokine production and increased expression of other T cell exhaustion markers such as Tim3 and PD1, suggesting that SIRPγ might serve as a marker for T cell exhaustion within tumor microenvironment.

Example 4

This example demonstrates that SIRPγ inhibits T cell effector cytokine release.

Figure 5A:
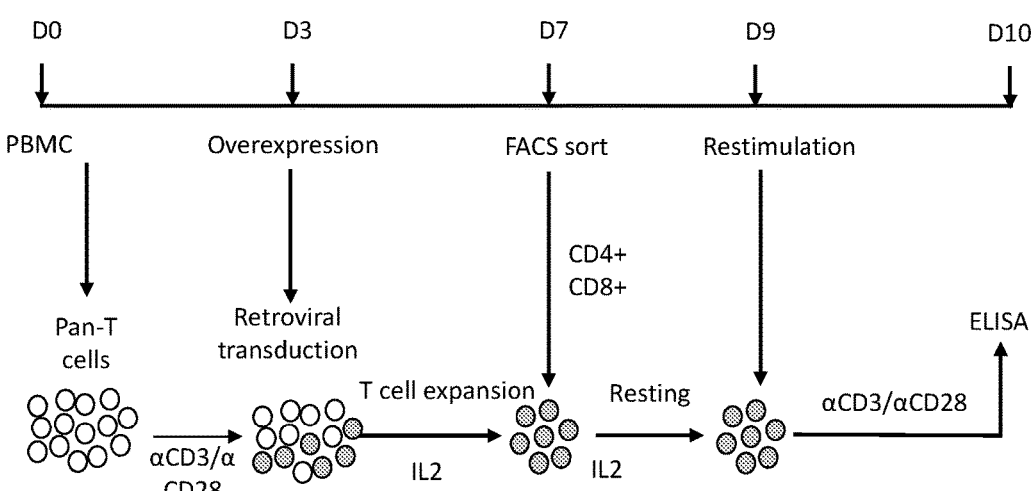
FIGS. 5A-5D demonstrate that SIRPγ overexpression on T cells inhibited IFNγ secretion.
Figure 5B:
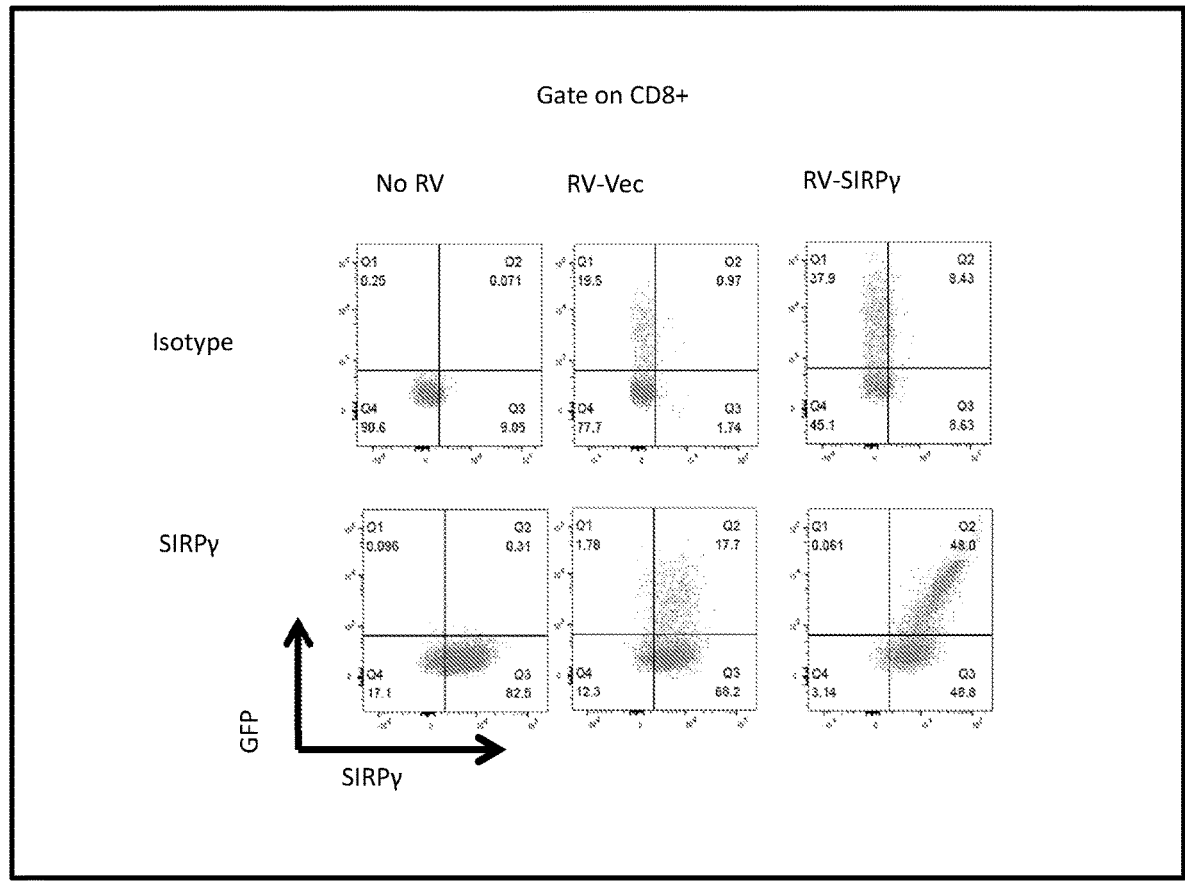
Figure 5C:
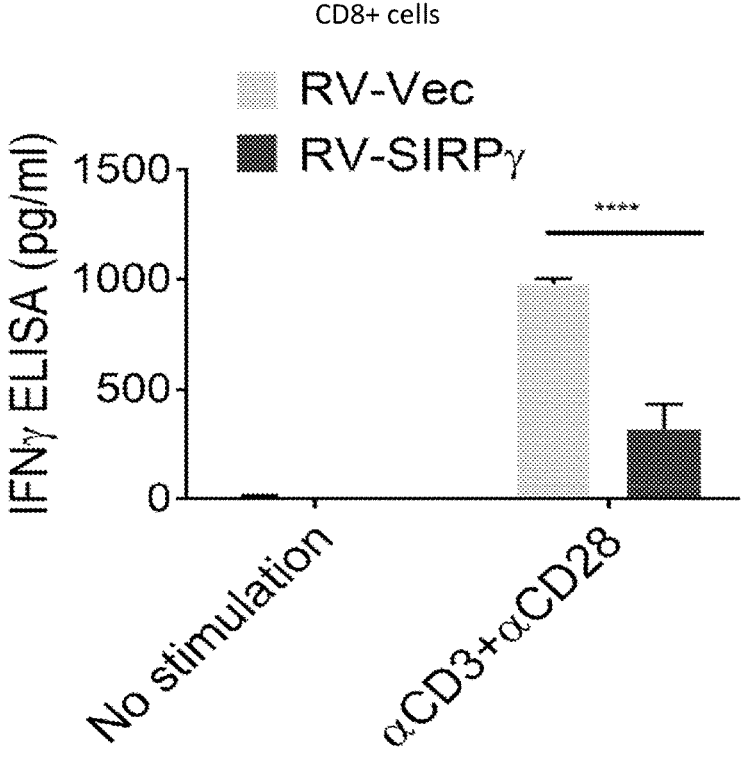
Figure 5D:
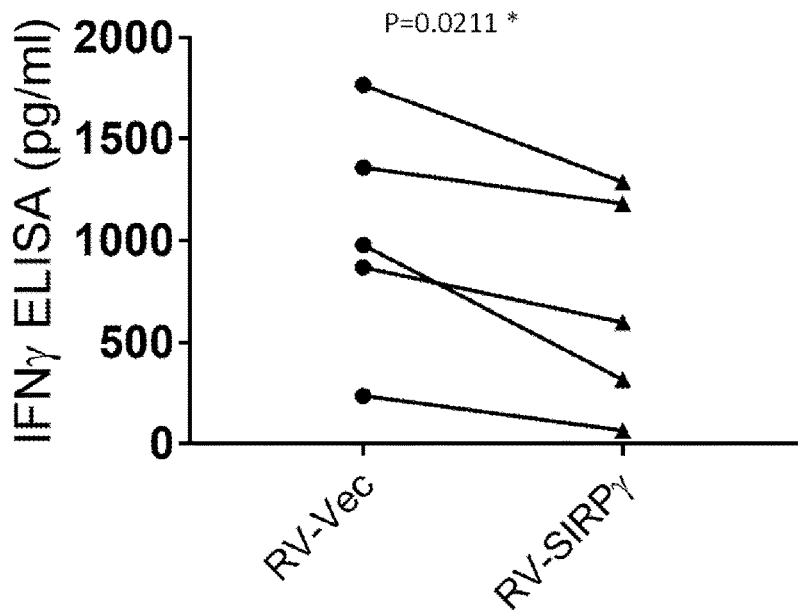
Figure 6A:
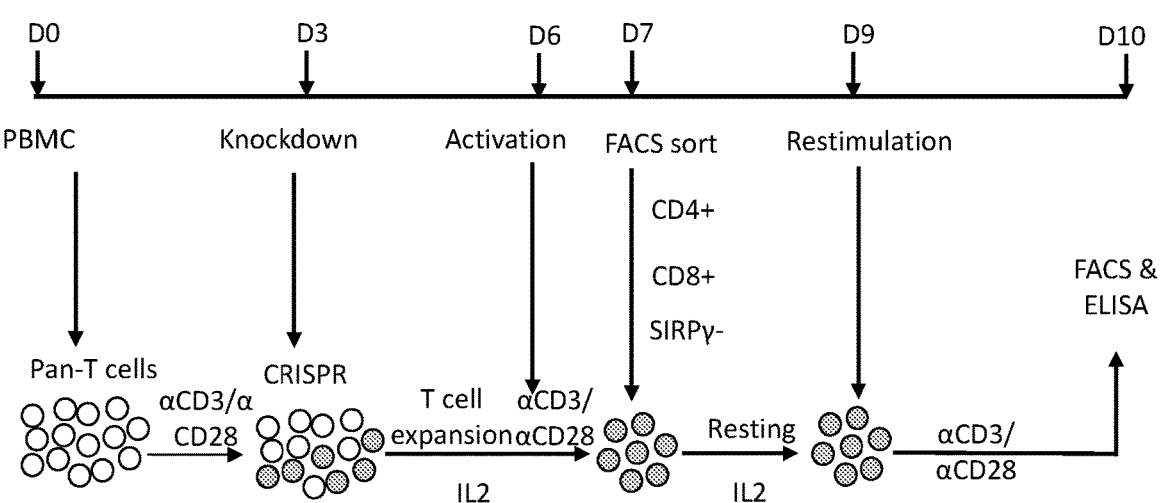
Figure 6B:
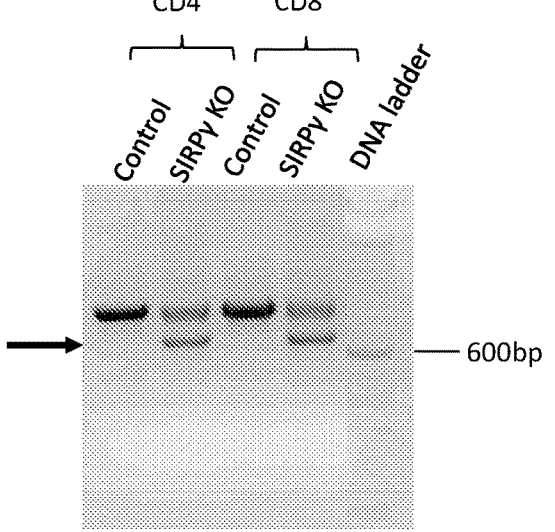
Figure 6C:
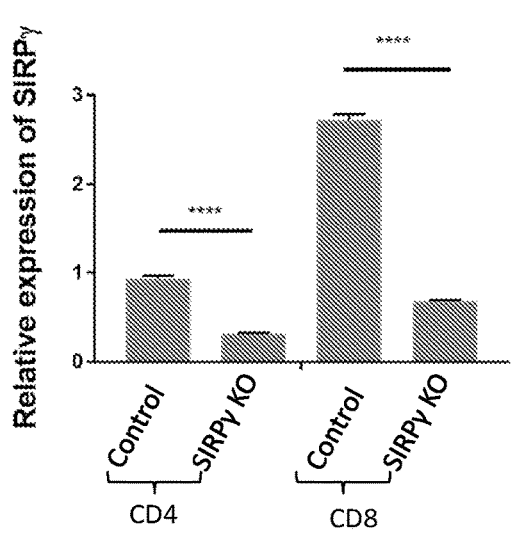

To study the function of SIRPγ in T cells, retrovirus-mediated overexpression of SIRPγ in T cells was carried out to mimic the high expression of SIRPγ on tumor-infiltrating CD8 T cells. Increased SIRPγ expression on CD8 T cells was observed on day 3 after retroviral infection (FIG. 5B). Interestingly, the SIRPγ-overexpressed CD8 T cells produced significantly less IFNγ than that by control virus-infected cells (FIG. 5C-5D), supporting an inhibitory role of SIRPγ in CD8 T cells.

To further evaluate whether SIRPγ is a negative regulator of T cell effector function, the level of SIRPγ on human T cells was knocked down using CRISPR. The success of CRISPR knockdown of SIRPγ was evaluated at genomic, mRNA, and protein levels. CRISPR delivery of SIRPγ guide RNAs (gRNAs) led to the deletion of targeted SIRPγ genomic coding region, significantly reduced SIRPγ mRNA expression, and SIRPγ protein expression on the T cell surface (FIG. 6B-6E). Notably, reduced expression of SIRPγ significantly enhanced secretion of IFNγ in CD8 T cells when stimulated with TCR signal in vitro (FIG. 6F), indicating that SIRPγ functions as a negative regulator of T cells. As noted herein, these results were surprising given previous studies suggesting SIRPγ as a T cell co-stimulatory molecule (Piccio et al., Blood 105(6): 2421-2427 (2005); Leitner et al., Immunol Letters 128(2): 89-97 (2010)).

Example 5

This example demonstrates that SIRPγ enhances regulatory T cell suppressive function and that monoclonal antibodies to SIRPγ have an inhibitory effect on T cell proliferation.

Figure 7A:
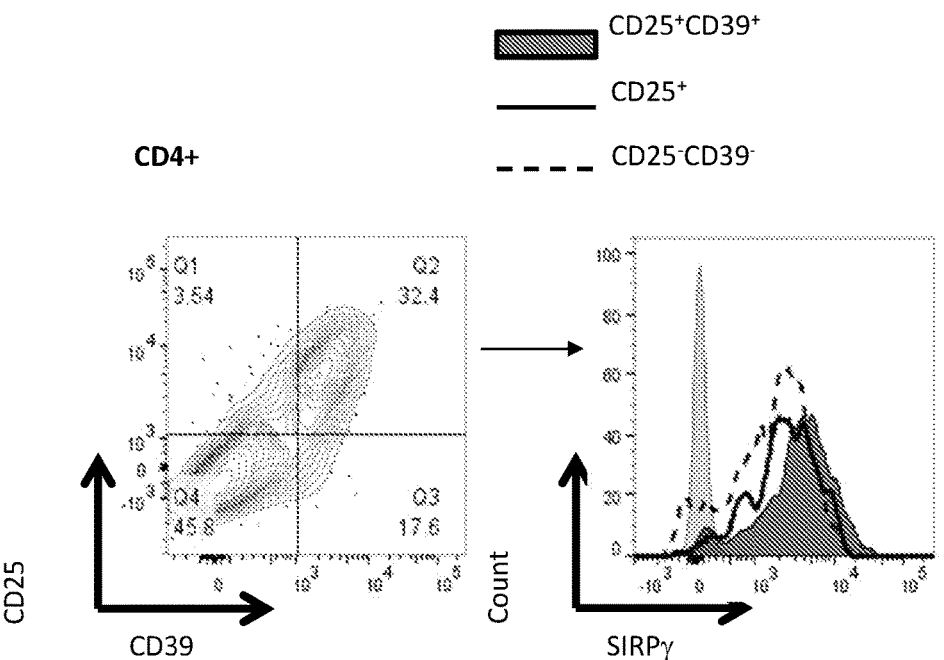
FIGS. 7A-7F demonstrate that SIRPγ overexpression on Treg cells enhanced suppressive function of Tregs.
Figure 7B:
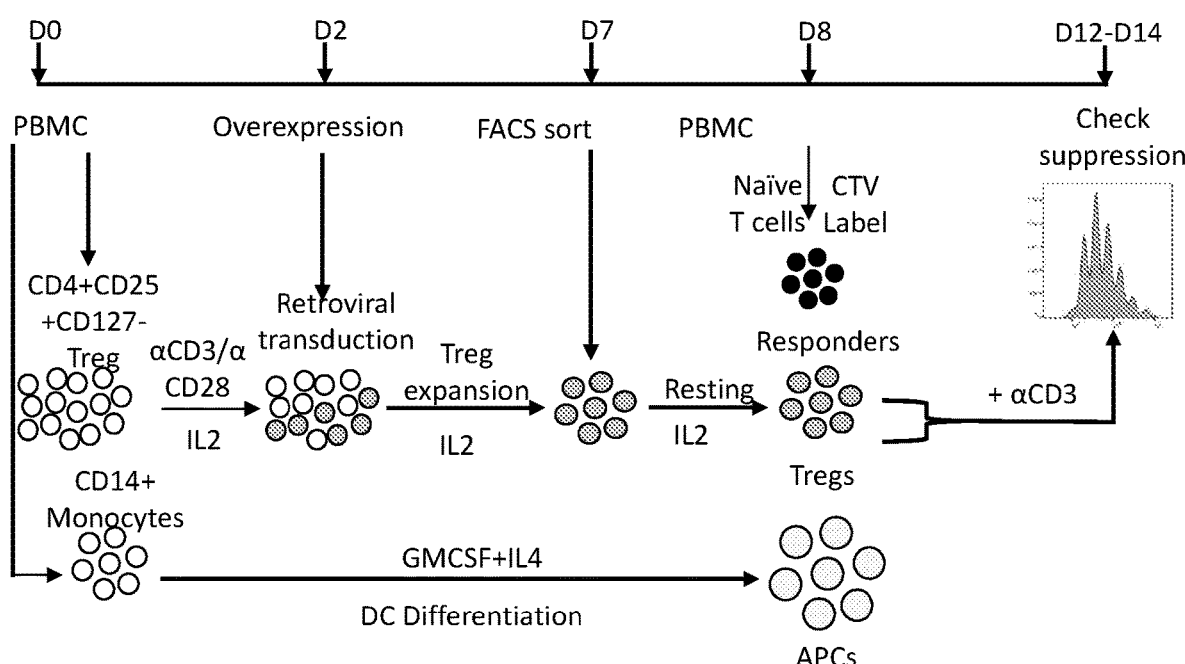
Figures 7C, 7D, 7E, 7F:
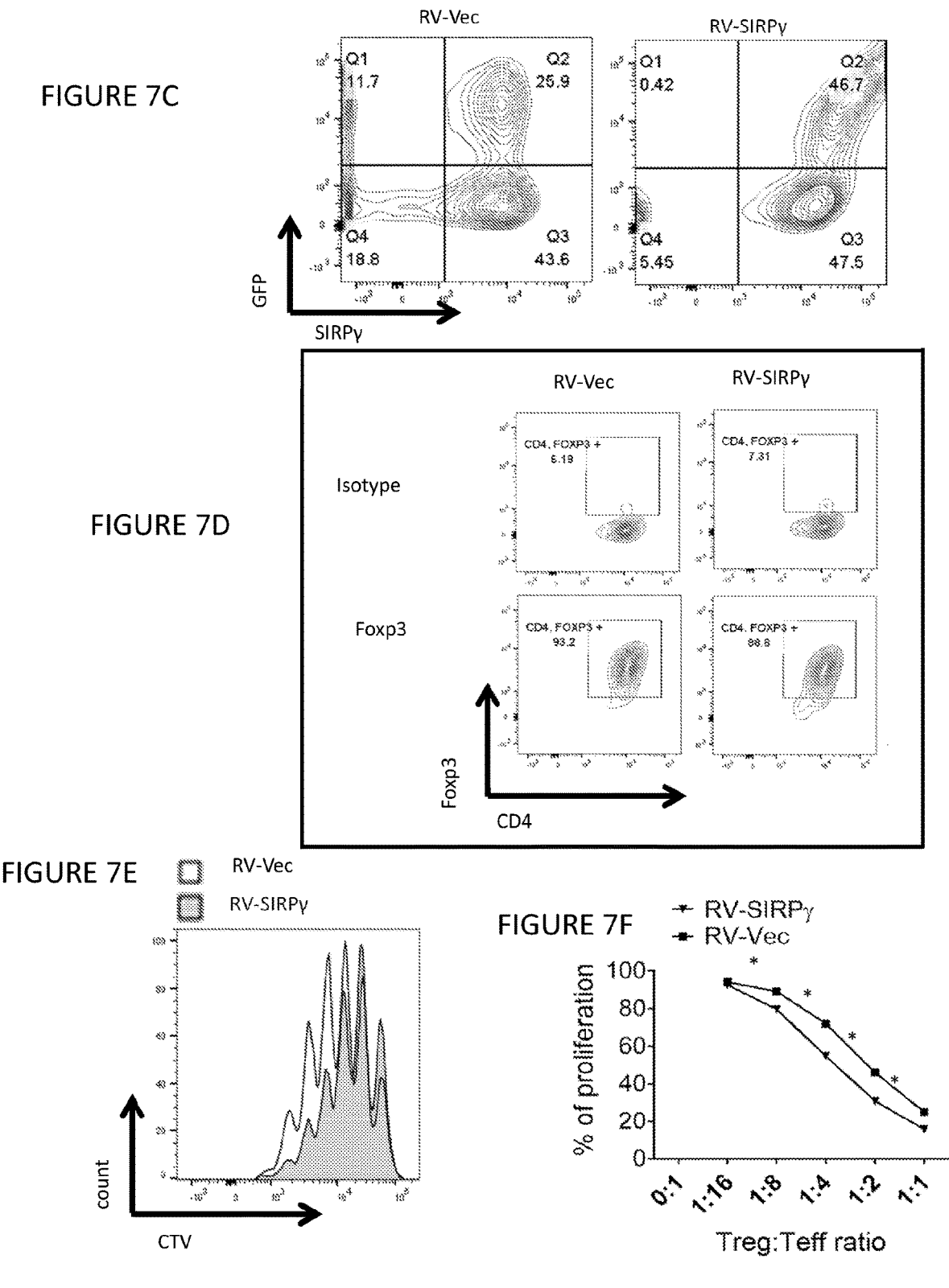

Previous RNA sequencing profiling on tumor infiltrating T cells also suggest that SIRPγ is upregulated in Tregs within HCC, CRC and lung cancer (FIGS. 3A-3C). Increased expression of SIRPγ in breast cancer additionally has been demonstrated (Ascension:GSE89225 dataset; Pitas et al. Immunity. 2016 Nov. 15; 45(5):1122-1134). A higher expression of SIRPγ in tumor infiltrated Tregs, compared to expression in non-Tregs, was confirmed in NSCLC tumor samples (FIG. 7A). Overexpression of SIRPγ in human Treg cells by retroviral transduction did not change FOXP3 expression levels on Tregs (FIG. 7C-7D). However, SIRPγ enhanced Treg suppression activity on T cell proliferation in the in vitro suppression assay (FIG. 7E-7F). These data suggest that heightened expression of SIRPγ in Tregs within tumor environment contributes to the suppression of effector T cell function. These data also suggest that inhibition of SIRPγ may lead to enhanced levels of T cell proliferation within the tumor environment.

Figure 8A:
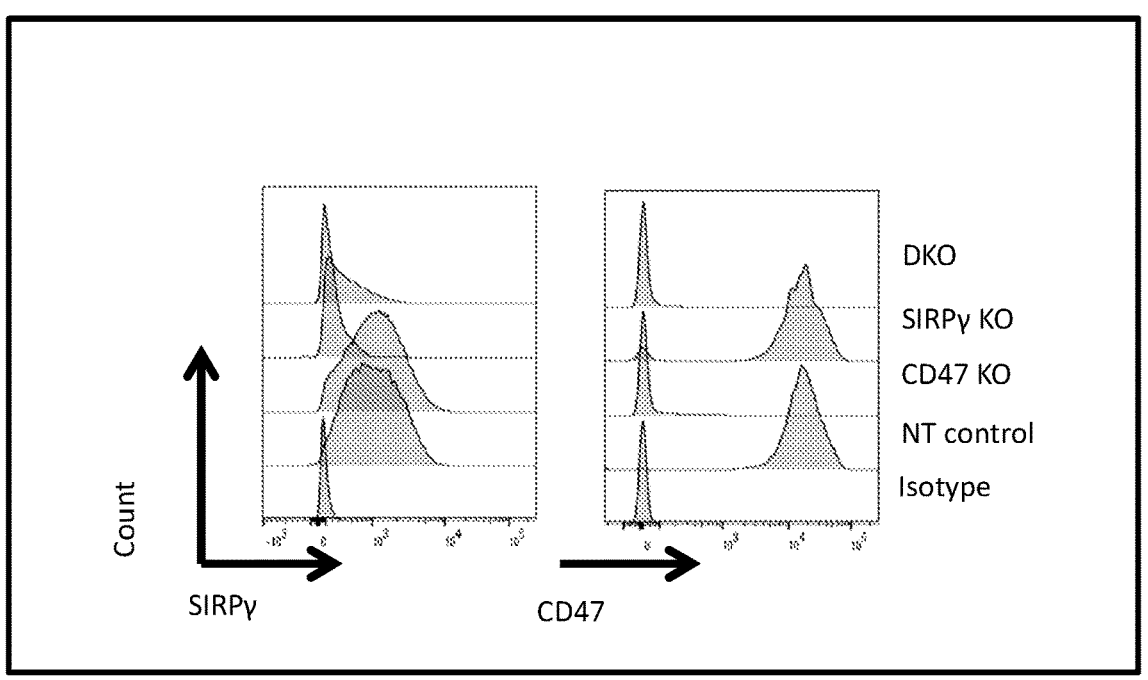
FIGS. 8A-8F demonstrate that SIRPγ antibodies have non-specific inhibitory effects on T cell proliferation.
Figure 8B:
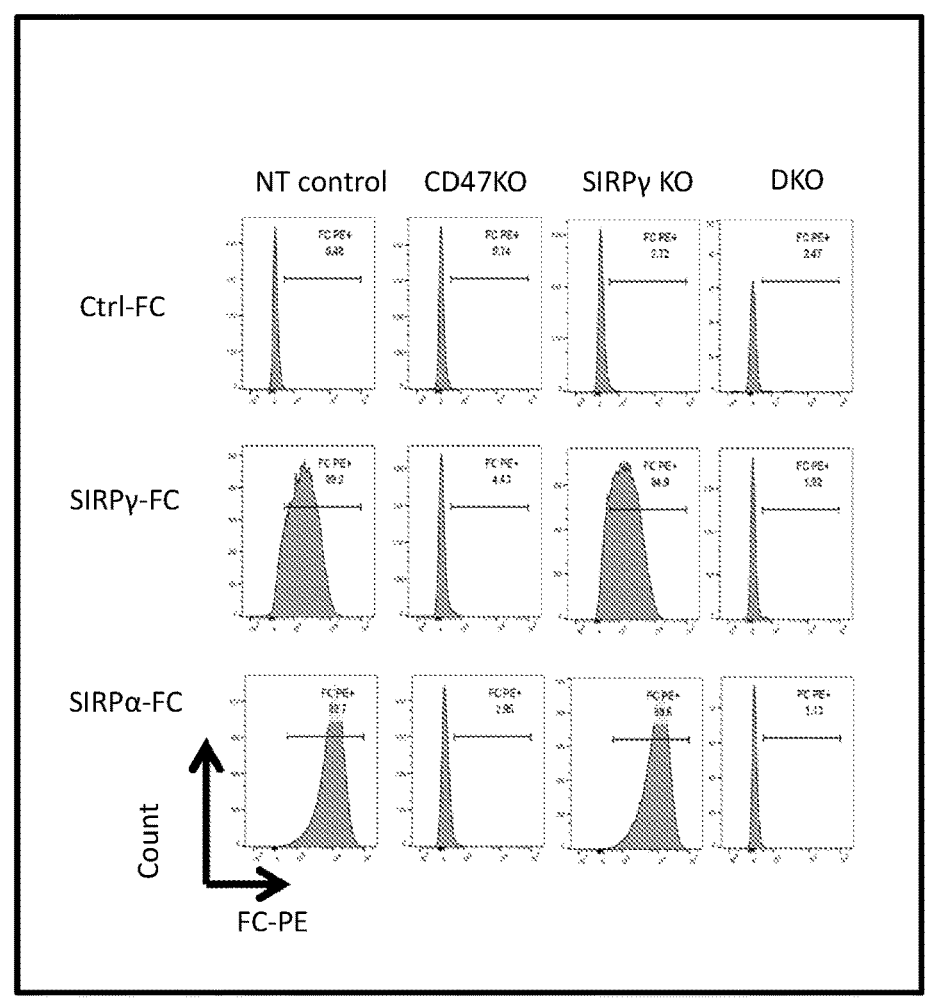
Figure 8C:
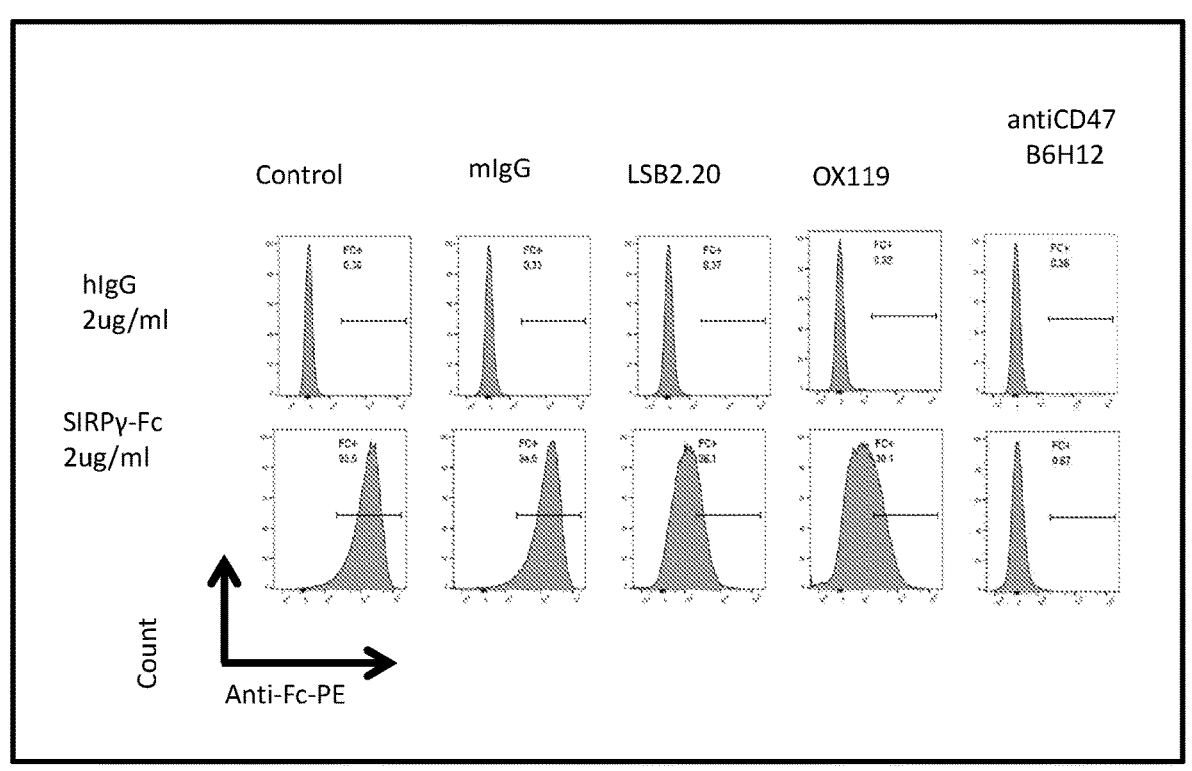

Previous studies (Piccio et al., Blood, 105:2421-2427 (2005)) indicated that CD47 is a ligand for SIRPγ. Piccio et al. also showed that anti-SIRPγ mAbs and anti-CD47 mAbs inhibited T-cell proliferation and ligation of SIRPγ co-stimulated T cell proliferation, which results supported SIRPγ as a positive regulator of T cell function. However, by using SIRPγ overexpression and SIRPγ knock-out system, the studies described herein suggest that SIRPγ is a negative regulator of T cell function. To further examine the discrepancy between previous results and the results described herein, the function of mAbs against SIRPγ during in vitro T cell proliferations was tested. To screen the functional blocking mAbs that can block the interaction between SIRPγ and CD47, SIRPγ and CD47 in Jurkat T cells was depleted through CRISPR (FIG. 8A). By using CD47 knockout cell lines, it was confirmed that SIRPγ binds to the T cell surface in a CD47-dependent manner (FIG. 8B). Furthermore, the mAbs clone LSB2.20 and OX119, which functionally block the interaction of SIRPγ-CD47 on Jurkat T cells, were identified through the in vitro binding assay (FIG. 8C).

Figure 8D:
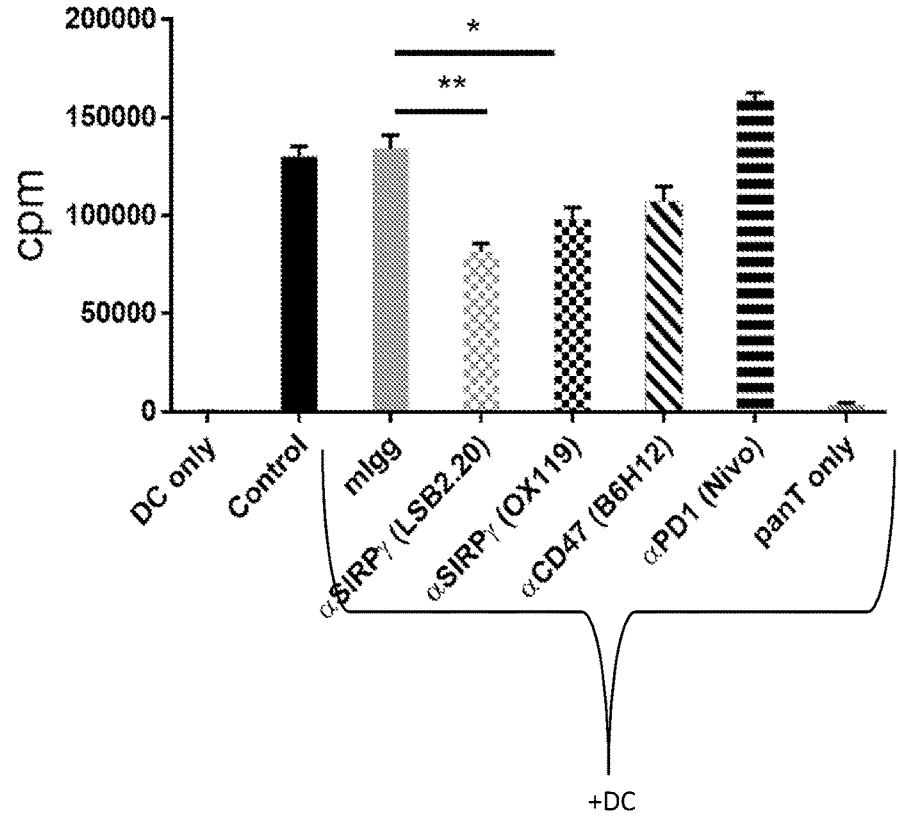
Figure 8E:
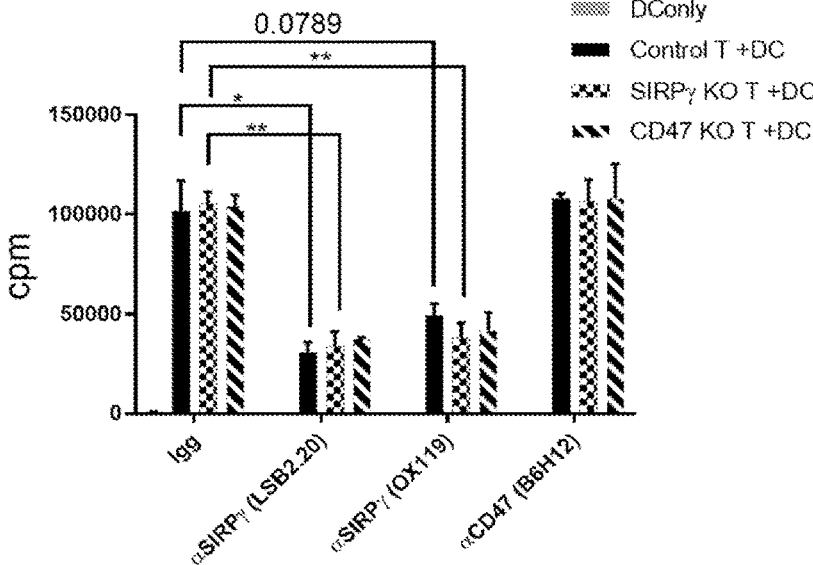
Figure 8F:
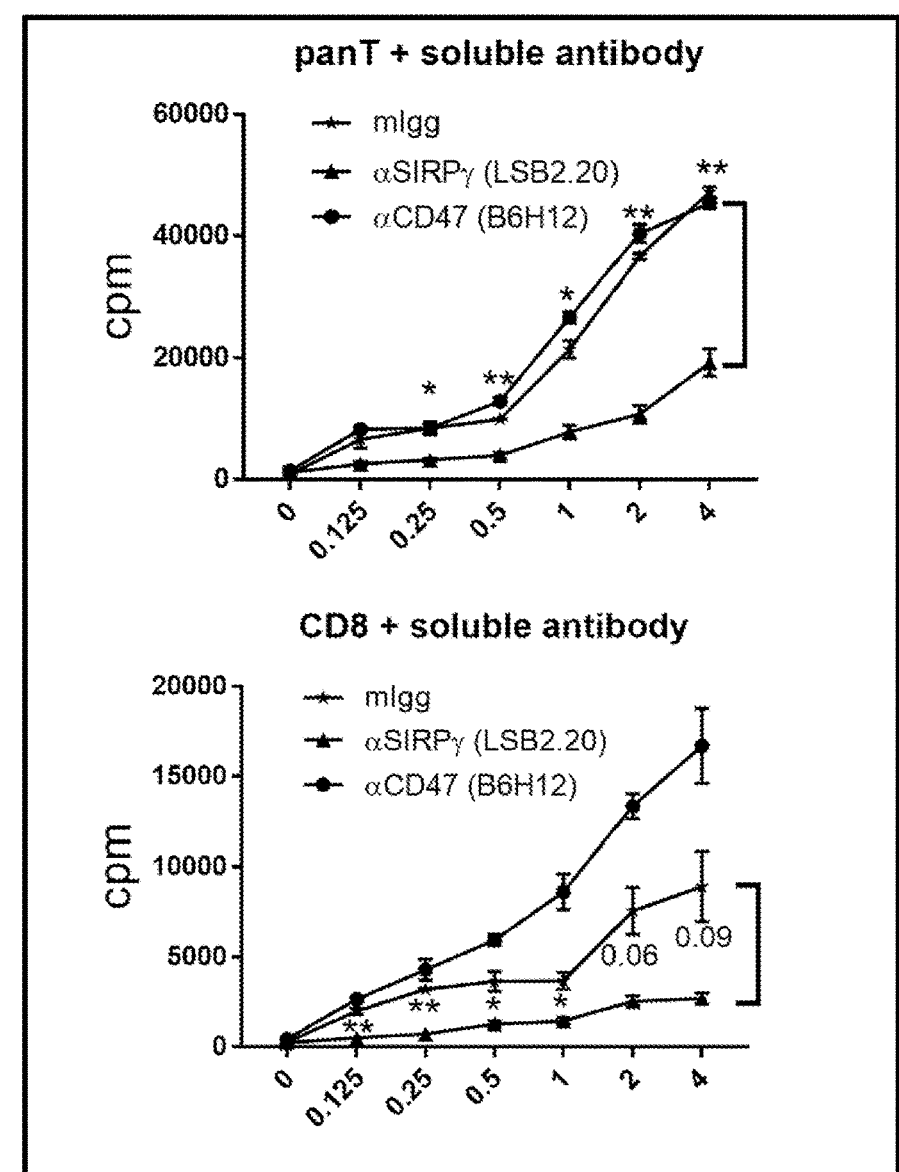

During mixed lymphocyte reactions (MLRs), some anti-SIRPγ mAbs inhibited T cell proliferation (FIG. 8D). In addition, treatment with anti-SIRPγ antibody inhibited the activation of T cells in the presence of serial dilution of a TCR ligand (8E). Interestingly, the inhibitory effect of the anti-SIRPγ antibody was independent of the presence of SIRPγ (FIG. 8F), since the inhibitory effect was still observed when SIRPG gene was knocked down by CRISPR mediated method as mentioned above. It is possible that the activities of these particular antibodies may be due to off-target effects or that the residues on SIRPγ that interact with CD47 are also required for interaction with other proteins to mediate its activity.

Example 6

This example demonstrates that anti-SIRPγ monoclonal antibodies which bind to a particular epitope of SIRPγ can enhance T cell proliferation and function.

Figure 9A:
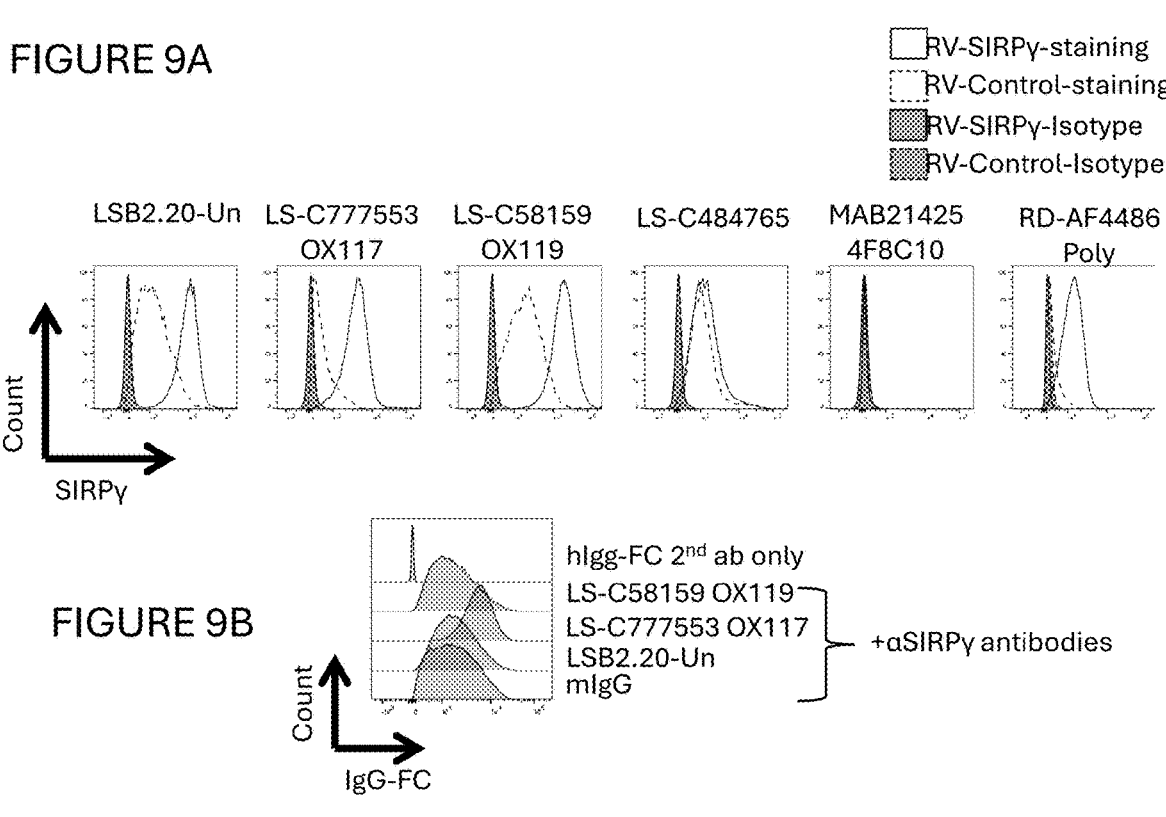

To explore the inhibitory effect of SIRPγ on T cell function, a panel of commercially-available SIRPγ antibodies were screened for their ability to bind to SIRPγ and perform as blockers of the CD47-SIRPγ interaction. T cells were treated with anti-SIRPγ monoclonal antibody clone LSB2.20, clone OX117, clone OX119, LS-C484765, clone 4F8C10 (MAB21425), or with polyclonal anti-SIRPγ antibodies (AF4486), and the binding of the antibodies to the T cells were assayed by FACS As shown in FIG. 9A, several anti-SIRPγ antibodies were capable of binding to SIRPγ endogenously expressed or exogenously overexpressed on Jurkat cells (FIG. 9A).

Figure 9B:
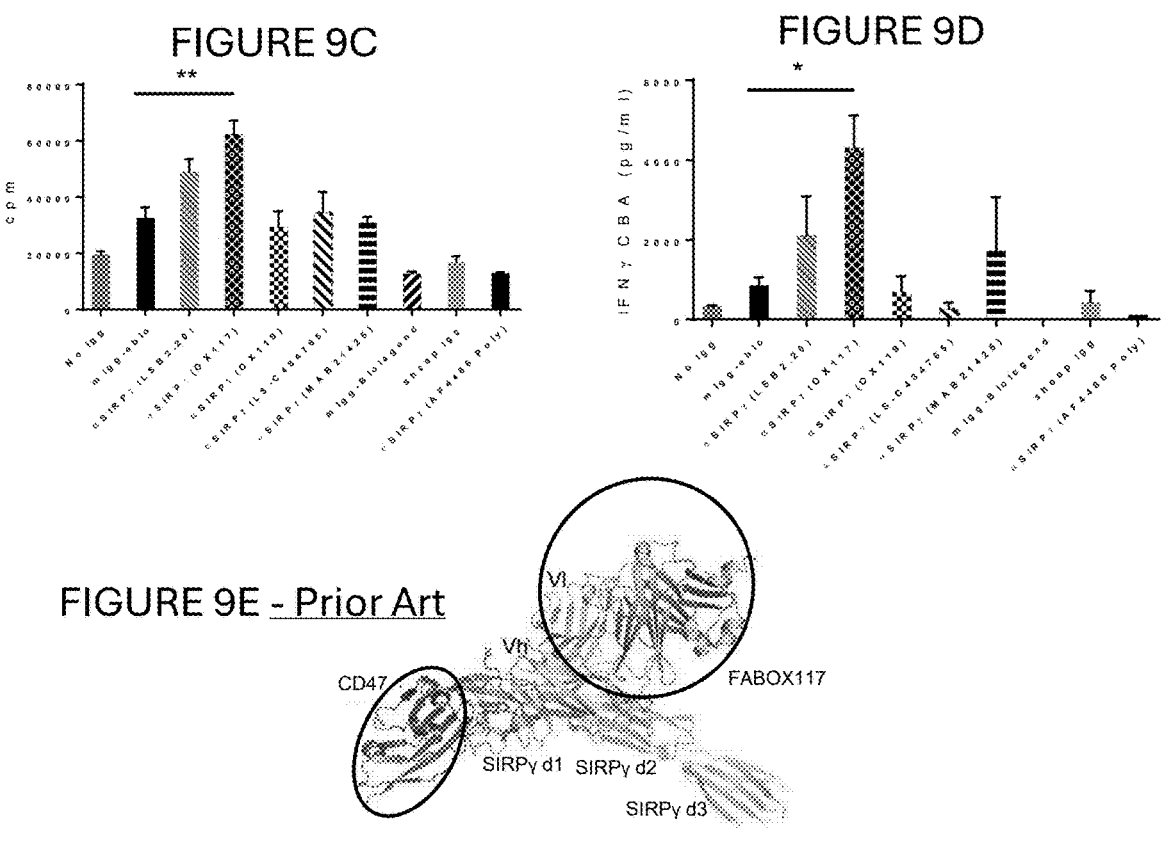

The ability of the anti-SIRPγ antibodies to alter the binding interactions between SIRPγ and its binding partners on T cells was evaluated by carrying out an in vitro antibody blocking assay. In this assay, SIRPγ-Fc binds to T cells, possibly through its interaction with SIRPγ binding patterns, such as CD47 or other unidentified receptors, expressed by T cells. At this moment, CD47 is the only known high affinity receptor for SIRPγ (FIG. 8C). However, in the absence of any SIRPγ antibodies, since SIRPγ is also expressed on T cells, it can potentially interact with CD47 and/or other putative binding partners in-cis on T cell surface. As a result, these potential in-cis interactions may inhibit the binding of SIRPγ-Fc with its binding partners on T cells in this assay. However, if preincubation of an anti-SIRPγ antibody, which disrupts the interaction between cell surface in-cis interaction between SIRPγ and its binding patterns, it could release these binding patterns on cell surface to subsequently interact with SIRPγ-Fc protein in this assay. Binding of SIRPγ-Fc to T cells was measured in the presence of the various anti-SIRPγ antibodies and compared to the binding in the absence of the anti-SIRPγ antibodies. As shown in FIG. 9B, cells pretreated with anti SIRPγ antibody clone LSB2.20 or clone OX119 didn't have enhanced binding of SIRPγ-Fc, suggesting that disruption of SIRPγ-CD47 interaction with these antibody clones does not result in the release of more CD47 or other binding partners for further interaction with SIRPγ-Fc fusion proteins, although these antibodies have been previously shown to block the interaction between SIRPγ and CD47. These data suggested that either the affinity of these antibodies might not be strong enough to release the cis-interaction between on the T cell surface, or CD47 and SIRPγ do not interact in-cis on the cell surface. In addition, these antibodies also do not block the potential interactions between SIRPγ and other putative binding partners. Interestingly, unlike clone LSB2.20 and OX119, clone OX117 treatment showed enhanced binding of SIRPγ-Fc fusion proteins. Since OX119 is known to bind epitopes on SIRPγ different from the epitopes interact with CD47 (FIG. 9E), these results suggesting that OX117 may be able to block interactions between SIRPγ and other putative binding proteins on Jurkat cell surface. After treatment with clone OX117, Jurkat cells released the putative binding partners for their binding by SIRPγ-Fc fusion protein (FIG. 9B).

The effect anti-SIRPγ antibodies have on T cell proliferation and IFNγ secretion was also tested. In this assay, T cells were treated with anti-SIRPγ monoclonal antibody clone LSB2.20, clone OX117, clone OX119, LS-C484765, clone 4F8C10 (MAB21425), polyclonal anti-SIRPγ antibodies (AF4486), one of three non-specific IgG controls, or with no antibody control. The level of T cell proliferation and IFNγ production were measured (FIGS. 9C and 9D). Interestingly, treatment of T cells with SIRPγ antibody clone OX117 demonstrated statistically significant and the highest level of T cell proliferation and IFNγ secretion in vitro (FIG. 9C-9D). The level of IFNγ secreted by T cells treated with OX117 was twice the level of IFNγ secreted by cells treated with LSB2.20, and more than 6 times the level of IFNγ secreted by cells OX119-treated. Reportedly, the fab fragment of anti-SIRPγ monoclonal antibody clone OX117 binds SIRPγ at the interface of the first and second immunoglobulin domains (D1 and D2) of SIRPγ (Nettleship et al., BMC Struct Biol 13: 13 (2013)) which region is distinct from D1 (which interacts with CD47). In addition, the epitope to which OX117 binds is distinct from the epitope to which SIRPγ monoclonal antibody clones OX119 and LSB2.20 bind. This suggests that the T cell proliferation and IFNγ secretion observed with OX117 is likely not caused by a direct blocking of CD47 binding to SIRPγ.

A summary of results from the above assays carried out with the panel of commercially-available anti-SIRPγ antibodies is provided in FIG. 10. Taken together, these data do not support a specific co-stimulatory function of SIRPγ, especially through its interaction with CD47. Instead, we identified a novel inhibitory function of SIRPγ in T cell proliferation, activation and cytokine production. Certain antibodies may interfere with this inhibitory function of SIRPγ and enhance T cell activities, which might be achieved through the blocking the interaction between CD47 and SIRPγ. These data also suggest that the T-cell inhibitory function of SIRPγ may be mediated through unique epitopes of SIRPγ and that molecules that bind to the interface of D1 and D2 of SIRPγ, similar to what is achieved by OX117, but is not limited by, may be useful in enhancing T cell function.

Example 7

This example demonstrates that SIRPγ inhibitors increase an immune response against a tumor or cancer in a subject.

T cells can kill cancer cells when they recognize tumor specific antigens. To amplify the T cell specific killing effect, T cells are engineered to express tumor antigen-specific T cell receptors (TCR) or chimeric antigen receptors (CAR) and thereby kill cancer cells. CRISPR knockout of SIRPγ is performed on antigen specific TCR-T or CAR-T cells. Human cancer cells that express tumor specific antigen are co-cultured with control or SIRPγ knockout antigen specific T cells in vitro to measure the anti-tumor immune response. The killing activity of SIRPγ knockout antigen specific T cells is measured through the quantification of surviving cancer cells. Secreted IFNγ is detected with standard ELISA assay. SIRPγ knockout antigen specific T cells exhibit increased IFNγ secretion and enhanced cancer cell killing. The tumor specific antigens include, but are not limited to, NY-ESO-1 and MART1/Melan-A.

Example 8

This example demonstrates that SIRPγ inhibitors lead to reduced tumor size and/or reduced tumor growth in a subject.

SIRPγ is not expressed on mouse cells. To establish a mouse tumor model for testing SIRPγ's effect on tumor growth, NOD scid gamma (NSG) immunodeficient mice are implanted with human cancer cells or finely minced patient-derived tumors that express specific tumor antigens. Control or SIRPγ knockout antigen specific T cells are engineered and expanded in vitro. After a tumor reaches a certain size (e.g., 50-120 mm³ in volume), control or SIRPγ knockout antigen specific T cells are adoptively transferred into NSG mice and tumor size is measured. The tumor specific antigens include, but are not limited to, NY-ESO-1 and MART1/Melan-A. Mice with SIRPγ knockout antigen specific T cells transfer exhibit reduced tumor size and tumor growth.

To establish an in vivo tumor model to test the effect of SIRPγ inhibitors on tumor immune response, humanized NSG (HuNSG) mice are generated through human pluripotent stem cell (HPSC) transplantation. 12 weeks post-human CD34+ HPSC transplantation, human cancer cells are injected into mice to develop tumor. Alternatively, for patient derived xenograft (PDX) tumor model, finely minced patient derived tumors are injected subcutaneously into HuNSG mice. Treatment is started when the tumors reached a certain size (e.g., 50-120 mm³ in volume). SIRPγ inhibitors are injected into HuNSG mice intravenously and tumor size and tumor volume is measured. Mice with SIRPγ inhibitors treatment exhibit reduced tumor size and tumor growth.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

---

What is claimed:

1. A method of treating a subject with a tumor or cancer, the method comprising administering to the subject an anti-signal regulatory protein gamma (SIRPγ) antibody comprising a means for binding SIRPγ at the interface between Immunoglobulin (Ig) Domain 1 (D1) and Ig Domain 2 (D2) of SIRPγ, in an amount effective to treat the tumor or cancer in the subject.

2. The method of claim 1, wherein the anti-SIRPγ antibody is a SIRPγ inhibitor.

3. The method of claim 2, wherein the anti-SIRPγ antibody reduces a binding interaction between SIRPγ and a SIRPγ binding partner.

4. The method of claim 3, wherein the SIRPγ binding partner is CD47.

5. The method of claim 1, wherein the anti-SIRPγ antibody is OX117 or an antigen-binding fragment thereof.

6. The method of claim 1, wherein the anti-SIRPγ antibody forms hydrogen bonds with one or more of amino acid residues Q8, E10, G109, K11, L12, and D149 of SIRPγ (SEQ ID NO: 3).

7. The method of claim 1, wherein the anti-SIRPγ antibody simultaneously binds to two SIRPγ molecules or promotes SIRPγ dimerization.

8. The method of claim 1, wherein the anti-SIRPγ antibody binds to an epitope which does not overlap with the CD47 binding site of SIRPγ.

9. The method of claim 1, wherein the anti-SIRPγ antibody forms hydrogen bonds with one or more of amino acid residues Q8, E10, G109, K11, L12, and D149 at the interface between Immunoglobulin (Ig) Domain 1 (D1) and Ig Domain 2 (D2) of SIRPγ (SEQ ID NO: 3).

* * * * *

```
                        SEQUENCE LISTING

<160> NUMBER OF SEQ ID NOS: 24

<210> SEQ ID NO 1
<211> LENGTH: 276
<212> TYPE: PRT
<213> ORGANISM: Homo Sapiens

<400> SEQUENCE: 1

Met Pro Val Pro Ala Ser Trp Pro His Pro Pro Gly Pro Phe Leu Leu
1               5                   10                  15

Leu Thr Leu Leu Leu Gly Leu Thr Glu Val Ala Gly Glu Glu Glu Leu
            20                  25                  30

Gln Met Ile Gln Pro Glu Lys Leu Leu Leu Val Thr Val Gly Lys Thr
        35                  40                  45

Ala Thr Leu His Cys Thr Val Thr Ser Leu Leu Pro Val Gly Pro Val
    50                  55                  60

Leu Trp Phe Arg Gly Val Gly Pro Gly Arg Glu Leu Ile Tyr Asn Gln
65                  70                  75                  80

Lys Glu Gly His Phe Pro Arg Val Thr Thr Val Ser Asp Leu Thr Lys
                85                  90                  95

Arg Asn Asn Met Asp Phe Ser Ile Arg Ile Ser Ser Ile Thr Pro Ala
            100                 105                 110

Asp Val Gly Thr Tyr Tyr Cys Val Lys Phe Arg Lys Gly Ser Pro Glu
        115                 120                 125

Asn Val Glu Phe Lys Ser Gly Pro Gly Thr Glu Met Ala Leu Gly Ala
    130                 135                 140

Lys Pro Ser Ala Pro Val Val Leu Gly Pro Ala Ala Arg Thr Thr Pro
145                 150                 155                 160

Glu His Thr Val Ser Phe Thr Cys Glu Ser His Gly Phe Ser Pro Arg
                165                 170                 175

Asp Ile Thr Leu Lys Trp Phe Lys Asn Gly Asn Glu Leu Ser Asp Phe
            180                 185                 190

Gln Thr Asn Val Asp Pro Thr Gly Gln Ser Val Ala Tyr Ser Ile Arg
        195                 200                 205

Ser Thr Ala Arg Val Val Leu Asp Pro Trp Asp Val Arg Ser Gln Val
    210                 215                 220

Ile Cys Glu Val Ala His Val Thr Leu Gln Gly Asp Pro Leu Arg Gly
225                 230                 235                 240
```

-continued

Thr Ala Asn Leu Ser Glu Ala Ile Arg Gly Pro Ala Ser Ser Leu Thr
                245                 250                 255

Ala Leu Leu Leu Ile Ala Val Leu Leu Gly Pro Ile Tyr Val Pro Trp
            260                 265                 270

Lys Gln Lys Thr
        275

<210> SEQ ID NO 2
<211> LENGTH: 1387
<212> TYPE: DNA
<213> ORGANISM: Homo Sapiens

<400> SEQUENCE: 2
agagcagggc ctgacatctc cccagaacag acgtttgaac agagcaggct tctgaggtct      60
ccaaaatgcc tgtcccagcc tcctggcccc atcctcctgg tcctttcctg cttctgactc     120
tactgctggg acttacagaa gtggcaggtg aggaggagct acagatgatt cagcctgaga     180
agctcctgtt ggtcacagtt ggaaagacag ccactctgca ctgcactgtg acctccctgc     240
ttcccgtggg accgtcctg tggttcagag gagttggacc aggccgggaa ttaatctaca     300 atcaaaaga aggccacttc cccagggtaa caacagtttc agacctcaca aagagaaaca      360
acatggactt ttccatccgc atcagtagca tcacccccagc agatgtcggc acatactact     420
gtgtgaagtt tcgaaaaggg agccctgaga acgtggagtt taagtctgga ccaggcactg     480
agatggcttt gggtgccaaa ccctctgccc ccgtggtatt gggccctgcg gcgaggacca     540
cacctgagca tacagtgagt ttcacctgtg agtcccatgg cttctctccc agagacatca     600
ccctgaaatg gttcaaaaat gggaatgagc tctcagactt ccagaccaac gtggacccca     660
caggacagag tgtggcctac agcatccgca gcacagccag ggtggtactg gacccctggg     720
acgttcgctc tcaggtcatc tgcgaggtgg cccatgtcac cttgcagggg gaccctcttc     780
gtgggactgc caacttgtct gaggccatcc gaggcccggc atcatccctt actcgcgctgc     840 tcctcatagc tgtcctcctg ggcccatct acgtccctg gaagcagaag acctgactct      900
ccttccttcc tcccctgcca cgtgggaccc tcatctctgc tgcctccttc ctttcctgag     960
aggctcagct tgagagaatg agccagtgag aagcttctct agacttggct ccaaacatct    1020
cccctcccaa gacatctgcc tgcccacagg ctcctgttgc tccttcacac agacctggat    1080
gccccagagc aaggtcttca ttcatggtcc tgagcaggtg ccatgggatt gggctctggg    1140
cactgactta acggcacctc cctagaaggc gagaaacatg ccaaatctaa acacaccagg    1200
actcccatcc atcgccttga gactgaccgt aaaccacaga cgctctccag gttctcaaga    1260
gttatcctgc cttccagatt cctgcctatc ccaactcccc agccttgttg aggttctcta    1320
ttgcctcttg aatacaaatg cactcccaaa gtggttttaa gaaaataaaa agattatcct    1380
tccaaaa                                                              1387

<210> SEQ ID NO 3
<211> LENGTH: 387
<212> TYPE: PRT
<213> ORGANISM: Homo Sapiens

<400> SEQUENCE: 3

Met Pro Val Pro Ala Ser Trp Pro His Pro Pro Gly Pro Phe Leu Leu
1               5                   10                  15

Leu Thr Leu Leu Leu Gly Leu Thr Glu Val Ala Gly Glu Glu Glu Leu
            20                  25                  30

```
Gln Met Ile Gln Pro Glu Lys Leu Leu Leu Val Thr Val Gly Lys Thr
    35                  40                  45
Ala Thr Leu His Cys Thr Val Thr Ser Leu Leu Pro Val Gly Pro Val
    50                  55                  60
Leu Trp Phe Arg Gly Val Gly Pro Gly Arg Glu Leu Ile Tyr Asn Gln
65                  70                  75                  80
Lys Glu Gly His Phe Pro Arg Val Thr Thr Val Ser Asp Leu Thr Lys
                85                  90                  95
Arg Asn Asn Met Asp Phe Ser Ile Arg Ile Ser Ser Ile Thr Pro Ala
                100                 105                 110
Asp Val Gly Thr Tyr Tyr Cys Val Lys Phe Arg Lys Gly Ser Pro Glu
                115                 120                 125
Asn Val Glu Phe Lys Ser Gly Pro Gly Thr Glu Met Ala Leu Gly Ala
    130                 135                 140
Lys Pro Ser Ala Pro Val Val Leu Gly Pro Ala Ala Arg Thr Thr Pro
145                 150                 155                 160
Glu His Thr Val Ser Phe Thr Cys Glu Ser His Gly Phe Ser Pro Arg
                165                 170                 175
Asp Ile Thr Leu Lys Trp Phe Lys Asn Gly Asn Glu Leu Ser Asp Phe
                180                 185                 190
Gln Thr Asn Val Asp Pro Thr Gly Gln Ser Val Ala Tyr Ser Ile Arg
                195                 200                 205
Ser Thr Ala Arg Val Val Leu Asp Pro Trp Asp Val Arg Ser Gln Val
    210                 215                 220
Ile Cys Glu Val Ala His Val Thr Leu Gln Gly Asp Pro Leu Arg Gly
225                 230                 235                 240
Thr Ala Asn Leu Ser Glu Ala Ile Arg Val Pro Pro Thr Leu Glu Val
                245                 250                 255
Thr Gln Gln Pro Met Arg Val Gly Asn Gln Val Asn Val Thr Cys Gln
                260                 265                 270
Val Arg Lys Phe Tyr Pro Gln Ser Leu Gln Leu Thr Trp Ser Glu Asn
                275                 280                 285
Gly Asn Val Cys Gln Arg Glu Thr Ala Ser Thr Leu Thr Glu Asn Lys
    290                 295                 300
Asp Gly Thr Tyr Asn Trp Thr Ser Trp Phe Leu Val Asn Ile Ser Asp
305                 310                 315                 320
Gln Arg Asp Asp Val Val Leu Thr Cys Gln Val Lys His Asp Gly Gln
                325                 330                 335
Leu Ala Val Ser Lys Arg Leu Ala Leu Glu Val Thr Val His Gln Lys
                340                 345                 350
Asp Gln Ser Ser Asp Ala Thr Pro Gly Pro Ala Ser Ser Leu Thr Ala
    355                 360                 365
Leu Leu Leu Ile Ala Val Leu Leu Gly Pro Ile Tyr Val Pro Trp Lys
    370                 375                 380
Gln Lys Thr
385
```

<210> SEQ ID NO 4
<211> LENGTH: 1716
<212> TYPE: DNA
<213> ORGANISM: Homo Sapiens

<400> SEQUENCE: 4
agagcagggc ctgacatctc cccagaacag acgtttgaac agagcaggct tctgaggtct      60

-continued

```
ccaaaatgcc tgtcccagcc tcctggcccc atcctcctgg tcctttcctg cttctgactc     120
tactgctggg acttacagaa gtggcaggtg aggaggagct acagatgatt cagcctgaga     180
agctcctgtt ggtcacagtt ggaaagacag ccactctgca ctgcactgtg acctccctgc     240
ttcccgtggg accgtcctg tggttcagag gagttggacc aggccgggaa ttaatctaca      300 atcaaaaga aggccacttc cccagggtaa caacagtttc agacctcaca aagagaaaca       360
acatggactt ttcatccgc atcagtagca tcaccccagc agatgtcggc acatactact       420
gtgtgaagtt tcgaaaaggg agccctgaga cgtggagtt taagtctgga ccaggcactg       480
agatggcttt gggtgccaaa ccctctgccc cgtggtatt gggccctgcg gcgaggacca       540
cacctgagca tacagtgagt ttcacctgtg agtcccatgg cttctctccc agagacatca     600
ccctgaaatg gttcaaaaat gggaatgagc tctcagactt ccagaccaac gtggacccca     660
caggacagag tgtggcctac agcatccgca gcacagccag ggtggtactg gacccctggg     720
acgttcgctc tcaggtcatc tgcgaggtgg cccatgtcac cttgcagggg gaccctcttc      780
gtgggactgc caacttgtct gaggccatcc gagttccacc caccttggag gttactcaac     840
agcccatgag ggtggggaac caggtaaacg tcacctgcca ggtgaggaag ttctacccc      900 agagcctaca gctgacctgg tcggagaatg gaaacgtgtg ccagagagaa acagcctcga    960
cccttacaga gaacaaggat ggtacctaca actggacaag ctggttcctg gtgaacatat    1020
ctgaccaaag ggatgatgtg gtcctcacct gccaggtgaa gcatgatggg cagctggcgg    1080
tcagcaaacg ccttgcccta gaggtcacag tccaccagaa ggaccagagc tcagatgcta    1140
cccctggccc ggcatcatcc cttactgcgc tgctcctcat agctgtcctc ctgggcccca    1200
tctacgtccc ctggaagcag aagacctgac tctccttcct tcctccctg ccacgtggga     1260 ccctcatctc tgctgcctcc ttcctttcct gagaggctca gcttgagaga atgagccagt    1320
gagaagcttc tctagacttg gctccaaaca tctcccctcc caagacatct gcctgcccac    1380
aggctcctgt tgctccttca cacagacctg gatgccccag agcaaggtct tcattcatgg    1440
tcctgagcag gtgccatggg attgggctct gggcactgac ttaacggcac ctccctagaa    1500
ggcgagaaac atgccaaatc taaacacacc aggactccca tccatcgcct tgagactgac    1560
cgtaaaccac agacgctctc caggttctca agagttatcc tgccttccag attcctgcct    1620
atcccaactc cccagccttg ttgaggttct ctattgcctc ttgaatacaa atgcactccc    1680
aaagtggttt taagaaaata aaaagattat ccttcc                              1716
```

<210> SEQ ID NO 5
<211> LENGTH: 170
<212> TYPE: PRT
<213> ORGANISM: Homo Sapiens

<400> SEQUENCE: 5

```
Met Pro Val Pro Ala Ser Trp Pro His Pro Pro Gly Pro Phe Leu Leu
1               5                   10                  15

Leu Thr Leu Leu Leu Gly Leu Thr Glu Val Ala Gly Glu Glu Glu Leu
            20                  25                  30

Gln Met Ile Gln Pro Glu Lys Leu Leu Leu Val Thr Val Gly Lys Thr
        35                  40                  45

Ala Thr Leu His Cys Thr Val Thr Ser Leu Leu Pro Val Gly Pro Val
    50                  55                  60

Leu Trp Phe Arg Gly Val Gly Pro Gly Arg Glu Leu Ile Tyr Asn Gln
65                  70                  75                  80
```

```
Lys Glu Gly His Phe Pro Arg Val Thr Thr Val Ser Asp Leu Thr Lys
                85              90                  95

Arg Asn Asn Met Asp Phe Ser Ile Arg Ile Ser Ser Ile Thr Pro Ala
            100             105             110

Asp Val Gly Thr Tyr Tyr Cys Val Lys Phe Arg Lys Gly Ser Pro Glu
        115             120             125

Asn Val Glu Phe Lys Ser Gly Pro Gly Thr Glu Met Ala Leu Gly Gly
    130             135             140

Pro Ala Ser Ser Leu Thr Ala Leu Leu Leu Ile Ala Val Leu Leu Gly
145             150             155             160

Pro Ile Tyr Val Pro Trp Lys Gln Lys Thr
            165             170
```

<210> SEQ ID NO 6

<400> SEQUENCE: 6

000

<210> SEQ ID NO 7
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 7
gggacccgtc ctgtggttca g                                              21

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
aaaagggagc cctgagaacg                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
gtatgtgccg acatctgctg                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
tacgtaaagt ggaaatttaa                                               20

<210> SEQ ID NO 11
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 11
tttgcactac taaagtcagt                                                       20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
tccatattag taacaaagca                                                       20

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
gcagttgtgt gacacggaag                                                       20

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
gggccctgac cacgctcatg                                                       20

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
gatctgcgcc ttgggggcca                                                       20

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
aggtgaggag gagctacaga                                                       20

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
ggtccaactc ctctgaacca                                                       20

```
<210> SEQ ID NO 18
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 18
ccctgcttcc cgtgggaccc g                                            21

<210> SEQ ID NO 19
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 19
ccagattggg aaggacaaga gctgt                                        25

<210> SEQ ID NO 20
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 20
ggcatgttgt gagggttaaa tgaga                                        25

<210> SEQ ID NO 21
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 21

Ser Leu Leu Pro Val Gly Pro
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 22

Leu Thr Lys Arg Asn Asn Met Asp Phe
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 23

Lys Phe Arg Lys Gly Ser
1               5

<210> SEQ ID NO 24
<211> LENGTH: 57365
<212> TYPE: DNA
<213> ORGANISM: Homo sapiens
```

-continued

<400> SEQUENCE: 24

```
ggaaggataa tctttttatt ttcttaaaac cactttggga gtgcatttgt attcaagagg       60
caatagagaa cctcaacaag gctggggagt tgggataggc aggaatctgg aaggcaggat      120
aactcttgag aacctggaga gcgtctgtgg tttacggtca gtctcaaggc gatggatggg      180
agtcctggtg tgtttagatt tggcatgttt ctcgccttct agggaggtgc cgttaagtca      240
gtgcccagag cccaatccca tggcacctgc tcaggaccat gaatgaagac cttgctctgg      300
ggcatccagg tctgtgtgaa ggagcaacag gagcctgtgg gcaggcagat gtcttgggag      360
gggagatgtt tggagccaag tctagagaag cttctcactg gctcattctc tcaagctgag      420
cctctcagga aaggaaggag gcagcagaga tgagggtccc acgtggcagg ggaggaagga      480
aggagctgta ggaaaacaca tccacactta gtcatctgct catctttcaa gacatgtttc      540
ctgagagtct gttatgttct cggggctggt ctcctgggat acctgtcact ggtggacagg      600
cagtcctgat agaactctgc ctgctcagcc atcctgccaa gtcctgatgc cctttccaat      660
attccttcca ctcagacaca cagagggtca gagcacaaac agccttcagg gcttcccatt      720
tgggtttctc aacattagtt tacaatgtgg atttctctga ccccatggag tcccagcatt      780
caaataatct acagatagcc tgcaagggac cacccactca tcactgcctc catgaaactc      840
ctagggcact gtggacatct ttgaacacat ttcaagcatc ccacattgta caccacccac      900
ataatttctg tgggttggga gccttttaaa gggttcccca agacttccga gggtgcggag      960
ggagcttaac tccacggacc ctggtgctgc atggcatgtg ggctgggcct tcctgttggc     1020
cttgcccttc tgagacagcc cttggtctgt cctcccttcc ttgtacttac agtcaggtct     1080
tctgcttcca ggggacgtag atggggccca ggaggacagc tatgaggagc agcgcagtaa     1140
gggatgatgc cgggcctgga aatcagggaa gacgaggggc tatgagagag accacttggg     1200
aggccattgt aggggcctcc acttacccca tctgaggctg cctgggccca tctatgcccc     1260
acctttgaac ctgcatcctg cccaggctat cttcactcca gcacaaggca gaagccacag     1320
aaagaggctc cccattctca ctcatcctgt cccaggttgc cagcttattc tcctggaggg     1380
aagaggtgga gggggtgtgt actcaggtat tcatacatgt ggcaacgggg ttcctcactt     1440
gaccctcaca agccatgggg agcagggatt gtcattccat tctgctaggg aaactgaggc     1500
ccatggattt tagggagggt cacaaggtta cttgcattca aacctaaaga agctcatcac     1560
tagtgttcct taggttgatc cctgagacca tgtcctttgg aacaaaacaa gtccaaattc     1620
ctagggacat tttaatgact ataaaagggt aggcaggtgg cttgaggatg gcttcacaat     1680
gagagttgca ggttccctgc ttagccccag aagtaagggg aggactccgt gttctcagaa     1740 cttgaggag ccatggaaca ctggacataa tgaaaccttc cggctagaaa acatcctggt     1800
gagtcacgga aatgggtctc atgcttggga gggcctcaga tgtcacctag gccacctcca     1860
ccccagtgca ggtgtcatct gaaatctttc tgttagttgg gcacactcag ttacgggaa     1920 gcacatgttt ggacgctgca ttttttaacat gagcagttca ggctttttaaa atcaacattt     1980 ttaacgcgag cagtttgggc cattaaagat attacagtat attttaaata aataaaatgg     2040
tgctggtggg tccttaagga agaaatggag aactcagcat ctgtggctgc tggggtgttg     2100
gaggccggca gttctcagct gggtggctct ctgggacttc ttctcccttg aggaaagctg     2160
cactgcccaa ttccaagttc actcctcctt ctaggggaca gcccacaaga aagattggct     2220
gaattgaaaa taggaaggcc acgcttctct cctcaattaa aaaacactac atgacgctct     2280
```

-continued

```
cagcccttgg gatcctccgc aggagcagct gggtctttgt tctacctgca ctgtagctca    2340
gcacctcgct cctcctacag tcctgcctcc ccatttcctg aggcatgctg accctacagc    2400
tcttcaggat gcttcctgca ttcctgtatc catctctagt ctgccttaca gagaaactga    2460
ccttggtaag ttgtctgtaa agcttactct aaaatataaa tttgaagcct gaatactcat    2520
cagctcgcaa tgaggacctc agggctggca gtgagtgggg ctgggcacca tggctgggat    2580
gcaattgata aaactttcac tggcagtaag ctgggatggc gtaaccacag gcaggaaatt    2640
ccttggcatc aggcttttga aacaaattgg gaaatggtag ttataaggac taacttgttc    2700
catggctatc actgggcata ttttttttgg ggaaatatgc tgagaagcta cgagtgattg    2760
attatgagtt aaggttcagc gtgaaagcaa gaggacttct tggcagcact gcactttctt    2820
atctcttgtg gctagagggc agaaagaata gagggttggg ccctggacat cattaaaaga    2880
gtagcagaat cacagaggag gatgaatctc agcttcaacg gttgctatgc tggggtaggg    2940
ccctgatggg gaagttgtgg gaccctgaga tgtgggagtg gacatttggg tcaaagcact    3000
caaagatctt cggttgactt aagagttgct gggtacaatt gcagcagcat agctacttat    3060
ctgtataaaa tatcctcccc aaatcaaata aaaaatgaaa acaaagtaag ttctgcacaa    3120
ccctggctct cagtattact tgaagagaga agccaaact gcaaatgac cgtgagtcaa    3180 aacagaacac tcacctaacc ctagtgcaca gtctcttacc cggctcccac gccactggtg    3240
cagcacttat gtaaccacaa ggcatcttgc attttacctg ccagcctaga caacttaaaa    3300
tgcatttcca gccttagtac ctgagcaaag atgctacatc tggcaaaccg aaagcaccca    3360
aaaatgccag ccctggtcct ggtccaagcc agtgggtgga tgaataactg aaaagcaaat    3420
gcaatccagt cttgatggtg cagttttacc tccctgagaa gtaaaactat gaaccctaga    3480
aacatcacaa ggatcaggaa taggagaaat tccaaggtgg gagaggaaga agggagactg    3540
actaggggcc tcaggactga gggacagccc tgcagccagg cacctgggac ccatccccca    3600
acaccagccc cagccataaa cggaggcaaa ggaatgacat agaaaagagc aaaagcctca    3660
agtcaattaa atcaccactt caagaaacta gaaaaagtag agcaaaataa actcaaagca    3720
agcaggagac aggaattaat aaaaagaaga gtgcaaaaaa tgaataaact ggaaacacaa    3780
aaacaattta aaaactcacg gaaacaaagt ggtcctttga aaagaccaat aaaatggaaa    3840
aaaactatag caaggctgat gaagaagaaa acagaaatgg catattttag atatgaggtt    3900
gaaacagggg atatcgccat aacccttcag acaccaaaaa gataataagg agatattatg    3960
aacaactcta cacacaaaaa tatgacaact tagataaaat ggacacaaaa ttcttcaaaa    4020
ggcacgagtt accggaactc acccaatatg aaatgaataa tatgagtaac cctaaactac    4080
tgaggaaatt gaatttatac ttttaaaaca cccccaaaaa ttcttgaggc ccaagtgttt    4140
caaagaaaaa tactgcaaag catttaaata tgaattaaaa ccaaatttag tgcacagaaa    4200
gatagtcata aaagaaattt gaggaaaatt tgaatgtata ctccatttta gatgatataa    4260
gggaattgtt ttaataattt tatgaaattt agtgattaaa aatttgaaat tgtattaact    4320
gtaataatga tactggtttt gttatgctgt ctttagtcat aagatcaccc aactatggat    4380
tccatttgga actgcgtgta catgcatgac tgagttagct gtggacatga tcacacgcct    4440
tccatacatc tctgattata gaagatattt tttgccctcc atttcctata tttactcttc    4500
cagcagacag ggacatggaa aaatccgtga cctagcactg acccagcaga taagactaac    4560
caccataagg tatgtgggag gaacctgggc ctttgaaaag tctcctggag ttgagactcc    4620
tcctggtatt acacaagagg gaagtaagac atattttggt catacggagt ggaacacagg    4680
```

-continued

```
ccaacttcag gtccatggga caatgcccag cagaagagga ctgtttctct aactagcaca      4740
aatttgcatt ttaggctgat actgaccttg tcctcaggga cccagattta ctttaattag      4800
tttgaaccaa taacccgatc taaaggcaag aggtcttcaa caacatcccc catgacttcc      4860
caagtcctag tttcccctct tttaaaactc cagacttact gggtggttga agcaaaaaca      4920
gagatcatgg atgaatggaa atttgcactt agtaaatttg cagaggggtt tgtgattatt      4980
gttgctcaaa tatcacaatc aggacacaga agaggtccgt tctgtgacca ttcatggtca      5040
cctgcaggcc tggtacagtt ttttttttt tttttgacag agtctcgctc tgtcgcccag       5100
gctggagtgc agtggcatga tctcggctca ctgcaagctc cgcctcctgg gttcacacca      5160
ttctcctgcc tcagcctccc gagtagctgg gactacaggc gcccgccacc acgcccggct      5220
catttttttg tattttttagt agagatgggg tttcaccgtg ttaaccagga tggtctcgat      5280
ctcctgacct cgtgatccgc ccgcctcggc ctcccaaagt gctgggatta caggcgtgag      5340
ccgccaggcc tggtacagtt ttaaactaca tttgtctttc tgaaacatac acagcagatg      5400
tcagggtgta ctgggatgag gtcataaatg aggatggaaa agtttggatg aaacagaaac      5460
aaagcagagg ttagaaaaag tagggagcac aagggtgggc tgatgagaaa cgggcacaac      5520
aactctcaag gaataaggga aggcaaagga ctctatgaga agatggttcc ccctgcctgc      5580
ctctttgctc cttaaatata tatttatgta cgccaggcgc ggtggctcac gcctgtaatc      5640
ccagcacttt gggaggctga ggcgggcgga tcacgaggtc aggagatcga gaccatcctg      5700
gctaacacgg tgaaacccca tctctactaa aaatacaaaa aattagtcgg gcgtggtggc      5760
gggcgcctgt agtcccagct actcgggagg ctgagacagg agaatggcgt gaacccggga      5820
ggcggagctt gcggtgagca gagatcgcgc cactgcactc cagtctgggc gacagagcca      5880
gactccgtct caaaaaaaaa aaaaattaaa catatattta tgtcaaaagt tctattaact      5940
tgtgcatcaa attcttacta gtcatgactc ttcgcatgtg ggatttgggg ggatggagct      6000
gacattaaaa tttactttg tatttataga cttctagctt atttttacagc aagtgtggat      6060 attactttta aaatgagaga aaaagacaaa atttaaaaat tttgagtaac ctcaccaggg      6120
gtagcatctg agctctggtc cttctggtgg actgtgacct ctagggcaag gcgtttgctg      6180
accgccagct gcccatcatg cttcacctgg caggtgagga ccacatcatc cctttggtca      6240
gatatgttca ccaggaacca gcttgtccag ttgtaggtac catccttgtt ctctgtaagg      6300
gtcgaggctg tttctctctg gcacacgttt ccattctccg accaggtcag ctgtaggctc      6360 tggggggtaga acttcctcac ctggcaggtg acgtttacct ggttccccac cctcatgggc     6420
tgttgagtaa cctccaaggt gggtggaact gaaacagcac agggtagaag ctctgatctt      6480
ctggcacaga cagatcacag ggagggctcc ataacttaac tcccactacc acggtgaggg      6540
catcaccagg acagtgctag gcaggcagca gatgctaaga cattgagggc gctctttgca      6600
tatgaatgaa attaccaagc acagtgcctg gtgcacagta ggtgctcaag gactggtagc      6660
tcctactagg ctaagaatga gtgaaatcta caagcacaac ccctggcatg cagttggaat      6720
gtaagaactg tagcaaaatc agtgaaatcg ccgagcacat agggacttgg ctcatagtag      6780
gtactcacta atagtagttg ttcttggtga gataaatgaa actctctagc gcagagcttg      6840
gcacgtgatt gctggtcccc tgaccgctgc caataaaatg atagtaagtg accagcacac      6900
ctaggtgcat ggcgggcggg cagtatagtc agggattaga ttacaggcca ttcaacctct      6960
ggagcaacag cctgggagga ggggagtggg cttgacagcc aggtgtgggc ttgggctggg      7020
```

-continued

```
tgtgagggtc ctctacctcg gatggcctca gacaagttgg cagtcccacg aagagggtcc    7080
ccctgcaagg tgacatgggc cacctcgcag atgacctgag agcgaacgtc ccaggggtcc    7140
agtaccaccc tggctgtgct gcggatgctg taggccacac tctgtcctgt ggggtccacg    7200
ttggtctgga agtctgagag ctcattccca tttttgaacc atttcagggt gatgtctctg    7260
ggagagaagc catgggactc acaggtgaaa ctcactgtat gctcaggtgt ggtcctcgcc    7320
gcagggccca ataccacggg ggcagagggt ttggctacaa aaggggcatc gataaacagg    7380
agacatgact gagatgacaa tcactaacga tgagtgtgtg acactgttaa gaaccttcag    7440
atacattaat tttaatcctt ctaataatgt ggagaggatg gtgttcttat tctcattta    7500 cagagcagga tgcaaaggtt ggaagaggtg acgaccagcc ccaggtcaga cagtgtaggg    7560
aaaggtccca gagggaagtc caggtctgag ttcaaagtcc tcctctccac atagggtgac    7620
ttccaccaat ctgggcacag aacaaagtt actgattgtt ctccctctgt gtattaactg    7680
gtgctagcct gtttccccag gagagctcac caacctcaga gagggtgttt acagaagcca    7740
aagtagggaa caatggcaaa gtggcgccac catgagacct gcaaccaggc tgctcagccc    7800
atgagagggg tggcctggaa catgcagccc ctcatctgca aagtgggaca gcagcatttt    7860
cccttcccag gggtgcaaca aggattaaat ggggccatgg aagaagtttt gctttggatc    7920
aaagtcagaa gatgcttcat aaaaataaac acagatctgt ctttaatcca gacttgacat    7980
atacctagag ctctctctct ttgtgtattt atgaatttat tccatatttt tcattctttt    8040
cacaaatatt ccagtacagt tttgaaaga aaatgaagta gttaaggcta aagctttaac    8100
atggagtcaa gcgtttgtaa gagcattgca ctcacacctg ctaaaggtca agccacagga    8160
tgttgctgta gacctggata acaatggact gaagtcaagg tacatgggat tttgatttct    8220
ctcatcctgg agtgtcctaa ttaagtaacc aattcatacg agtttgcagt ttagcatttc    8280
tgccaggcaa tgaactgttt tcaaaaacaa cattttgtga aagtccccag tacaaaactt    8340
ttcctgcatt gccctatggg acactgttca ggactaccat gactcagggt tcccaaattg    8400
caactcttta tttcccagat aaatgctatt tcctttggcc ttcctatcaa tcattatttt    8460
ttttagttag caggtctaat ctgtgccaag tcccaaattt gaaaagaggg aaggtttctt    8520
ggaatctagg tcttcagttg ggccaggttg ggtccaaaaa caatgatcac tgagtactaa    8580
gaaagccaaa ggtgggtgat ttcttcatcg ttaattcatt acaagagaca aagatctagg    8640
ccaccccaac aggcagaaat ctatcctggg tcctgaaagc acacaaactg gagaatcaga    8700
aaaatgaggg tagtttctcc ctgtagatga gtcctaaacg tgtctccaaa ttgctaatta    8760
ttaccctgca cctcctatag cagtcatcag gaaacacata ttaggcatac ttgcatttgt    8820
aaatattaac ttgctcccta ccacatgcaa acattttatg ggcacagtaa gaagggtgtc    8880
acttgaagaa gtcaagtcat caagacacca gcagcattgg gcatccctag agggctgaga    8940
ggctgtaacc agttgccatt tattgagggc ttcttgggag cctgatgctg gctgctccct    9000
ctgtacctct cagctcttta atcctccctt tattgccttg aggggtcct cgtgtgagtc    9060 ccttatagga ccagggtctg aggggacccc agctagcaaa gggccaaaag tggataaaaa    9120
acccaccctg gtaaggtgag ggaggatgaa ggcaagcacg gagcctggta tgcagcaggt    9180
gcttaataaa tgagccctat ggctgttatc aagaggtttg gtcattacta cttctgaatc    9240
tacacactta ttctttaggc agcagaacat agaggagtag aaacaccaag aaaaggctca    9300
aatcctgctc cctgcagctc atgaaaaact caaatgataa taaaagcaaa accaccaagt    9360
ctggacaact ggctttcaaa aaaaaataag atcataggta aagctggaag cattttggaa    9420
```

-continued

```
ggaggaggga acagagtcct ctgtgacatc tttttattat tattatttta ctttaagttc   9480
tgggatacaa gtgcagaata tgcaggtttg ttttataggt tatgtttgcc atggtggttt   9540
gctgcactta tcaacccatc atctagattt taagccctgc atgcattagc tatttgtcct   9600
aatgctctcc ttcccctcac ccccccaccc cttgactggc cctggtgtgt gttgttcccc   9660
tccctgcgtc catgtgttca cattgtgcaa ctcccactta tgagtgagaa catgtggtgt   9720
ttgcttttct gtccctgtgt tagtttgctg aggataatgg cttccagctt catccatggc   9780
cccgcaaagg acatgaactc attctttttt atggctgcat agtattccat ggtgtatatg   9840
taccaccttt tctttgtcca gtctatcact gatgggcatt tgggttggtt tcatgtcttt   9900
gctattgtaa atagtgctgc aataaacata catgtgcatg tgtcctcata gtagaatgat   9960
ttatattcct ttggttacat acccagtaat gggattgctg ggtcaaatgg tatctctggt  10020
tcttgatcct taaggagtca ccacactgtc ttccacaatc gttgaactaa tttacattcc  10080
caccaagaat gtaaaaacgc tcctattttt ccacagcatc accagcatct attgtttcct  10140
aactttttaa taatcaccat tctgactggc atgagatggt atctcattgt ggttttgatt  10200
ttcatttctc taatgatcag tgatgttgag ctttttttttca tatgtttgtt ggccacataa  10260
atgtcttctt ttgagaagtg tgtgttcata tactttgcat acttttttgat ggggttgttt  10320 gtttttttct tgtgaatttg tttaagttcc ttgtagattc tggatattag accttttgtca  10380 gatgggtaaa ttgcaaaaat tttctcccat tctgtaggtt gcctgttcac tctcatgata  10440
gtttctattc ctgtgcagaa tctctttagt ttaattagat accatttgtc aactttcact  10500
tttgttgcaa ttgcttttgg cattttcgtc atgaagtctt tgcccatgcc tatgcctgaa  10560
tggtattgcc taggttttct tctagggttt ttatggtttt gggttttaca tttaagtctt  10620
taacccatct tcagttaatt tttgtataag gtgtaaggaa ggggtctggt ttcagttttc  10680
tgcatatggc taaccagttt tcccagtccc atttattaaa tagggaatcc tttccccatt  10740
gcttgttttt ctcaggtttg ttgaagatca gatggttgta aatgtacagc attatttctg  10800
aggtctccgt tctgttccat tggtctatat gtctgtcttg gtacaagtac catgctgttt  10860
tggttactgt agccttgtaa tatagtttga agtcaggtag cgtgatgcct ccaattttgt  10920 tcttttttgct taggattgtc ttggctatac gggctttttt ttggttcaat ataaaattta  10980
atgtagtttt ttttctaatt ctgtgaagaa tgtcaatggt aatttgatgg gaatagcact  11040
gaatctataa attacttttt catgacattc atccttccta tccatgagca tggaatgttt  11100 ttccatttttt ttgtgtcctc tcttatttct ttgaagcagt ggtttgtagt tctccttgaa  11160
gaggtccttc aaatcccttg taagttgtat tcctaggcat tttattctct ttgtaccaat  11220
tgtgaatggg agttcattca tgatttggct ctctgcttgt ctattgttgg tgtataggaa  11280
tgcttgtgat ttttgcacat tgatttttcta tcctgagact ttgctgaagt ttcttatcag  11340
cttaaggagt ttttgagctg agatgatggg gctttctaaa tatagaatca tgtcatctgc  11400
aaacaaagac aatttgactt cctctcttct tatttgaata ccccttattt ccttctcttg  11460
cctgattgct ctggacagaa cttctaatac tatgttgaat agaaatggct agagagggcg  11520
tccttgtctt gtgctggttt tcaaggggaa tgtttccagc ttttgcacat tcattatgat  11580
actggctgtg gggttgtcat aaatagttct ttttattttg agatatgttc cgttaatacc  11640
taatttattg agaatttta gcatgaagcg gtgttgaatt gtattgaagg ccttttctgc  11700
atctattgag ataatcatgt ggctttttgtc attggttctg tttatgtgat ggattacatt  11760
```

```
tcttgatttg cgtatgttga acaagccttg catgccaggg atgaagccaa tttgattgtg   11820
gtggataaac tttttgatgt gctgcgggat tcagtttgcc agtattttat tgaggatttt   11880
cactttgatg tttatcaggg atactggcct gatgtttttct ttttttgttc tgtctctgcc   11940
aggctttggc atcaggatga tgctggcttc ataaaatgag tcaggaggt gtcccacttt   12000 ttctagtatt tggaatagtt tcagaaggaa tggttccagc tcctcgttgt acctctggta   12060
gaatttggct gtgaatccat ctggtcctgg gctttttttg gttggtaggc tattaattac   12120
tgcctcaatt tcagaacttg ttattggtct attcaggggc tcgatttctt tttggtttag   12180
tcttgggagg gtgtatgtgt acaggaattt atccatttct tctagatttt ctagtttatt   12240
tgcgtagaag tgttcatagt attttctgat gttagtttgt gtttccatgg ggtcagtggt   12300
gatatcccct ttatcttttt tttattgatt tgattcttct ctcctttctt ctttattagt   12360
ctagctagtg gtctattttg ttaatttctt caaaaaacca gcttctggat tcattgattt   12420
tttgaagggt tttttgtgtc tttatctcct tcagttcgtt tctgatctta gtcatttctt   12480
gtcttctgct agctttttgct cttgcttctc tagatctttt aattgtgatg ttacggtgtt   12540
gatttcagat ctttctagct ttctgatgtg ggcattccgt gctataaatt tccctctaaa   12600
cactgcttta gctgtgtccc agagattctg gtatgttgtc tctttgttct tattggtttc   12660
aaataacttc ttaatttctg tcttaatttc attatttacc caggagtcat tcaggagcag   12720
gctgttcaat ttccatgtag ttgtgtggtt ttgagtgagt ttcttaattc tgagttctaa   12780
tttgattgaa ctgtggtctg ataaactgtt ggctatgatt tccgttcttt tgcatttgct   12840
gaggagtgtt ttacttccaa ttatgtggtt gattttagaa taagtgcctt gtggcactga   12900
gaacaatgtg ttttctgttg atttgggggtg gagagttctg tagatgtcta ttaggtccac   12960
ttgatccaga gctgagttca agccctgaat atccttatta attttctgtc tcattgatct   13020
gtctaatatt gacaatgggg tattaaagtc tcccactatt attgtgtggg agtctaagtc   13080
tttttgtagg tctctaagaa cttggtttat gaatctgggt gctcctatat ttaggatagt   13140
tagttgaatt gatcccttta ccattaggta atgcccttct ttgtcttttt tgatctttgt   13200
tggtttaaag tttgtttttgt cagggaccag gatcgcaacc cccaccttct tttgctttcc   13260
atttgcttgg taaattttcc tccatccgtt tgttttgagc ctatgtgtgt ctttgcatgt   13320
gagatgggtc tcctaaatac agcccaccga tggggcttga ctctttatcc aatttgcctg   13380
tctatgtctt ttaatcgggg gatttaacct aattacattt aagcttaata ttgttatgtg   13440
tgaatttgat cctgtcttca tgatgctatc tgattatttt gcacaccagt tgatgcggtt   13500
tcttcatagt gatcactgat ctttatattt tggtatgttt ttgcagtggc tggtaccggt   13560
tttttccttt cacatttagt acttctttca ggagctcttg caaagcaggc ctggtggtga   13620
caaatccctc agcatttgct tgtttggaaa ggattgtatt tctccttcac atatgaagct   13680
tagtttggct agatatgaaa ttctgggttg aaaattcttt tgtttaagaa tgttgaatat   13740
tggcccccac tctctcctgg cttgtagggt ttctgctaat agttgttctg ttagtctgat   13800
ggacttccct ttgtaggtga ccttgccttt ctctttggct gcccttaaca tttttttcctt   13860 cattttgacc ttggagagtc tgattattat gtgtcttggg gttgatcttc ttgtggagta   13920
tcttagtggt gttttctata tttcctgaat ttcaatgtta tcctgtcttg ctaggttggg   13980
gaagttctcc tggataatat cctgaagtgt gttttccaat ttggttccat cctccccatc   14040
tctttcaggt actccaatca atcatagctg tgatcttttt acatagtccc atatttctct   14100
gaggttttgt tcattccttt tcattctttt tttaaaatct tgtccgcatg tcttatttca   14160
```

-continued

```
gcaaaatggt cttcaaactc tgatatcctt tcttctgttt ggttgattcc actactgata   14220
cttgtgtatg cttcacaaag ttcttgtgct acgtttttta gctccatcag gtcatttatg   14280
ttcctctata aactggtttt tctggttacc agctcctgta accttttatt aagattctta   14340
gcttctttgc gttgggttag aacttgctcc cgtagctcag cggactttgt tattactcac   14400
cttctgaagc ctacttccgt caattcgtcc atttcctcct ttgtccagtt ttgcacccct   14460
gctggagact cattgcgatc atttggagga gaagaggcaa ctctggcctt ttgggttgtc   14520
agtgttttct gttgattttt tctcatcttc atgaatatgt ctagttttga tctttcaggc   14580
tgctgaccct tggatggggt ttttgtgggg actttttttg ttgatgctgt tgttgccttc   14640
tgtttgtttt tctttcaatg gtcaggtccc ttccctgcaa ggctgctgca gtttgttggg   14700
ggttcacttc gggcctttc atctggttgg ctcccacacc tggacatgtc acttgaagag   14760
gctggagaac ggcaaagatg ggtgcctgct ccttccttta ggatctctaa cctcgagggg   14820
cactgatcta atgccagtag gagcactcct gtgtagggtg tccgacaacc cctattagag   14880
ggtctctctc agttgggtgg cacggggagc aggacccatt taacgaagca ctttgactgt   14940
cccttggtgg agtgagtgtg cttcagtggg gaaaaaccca cttatctggg ctgcccagat   15000
ttctcagaac tagcagcagg aaaaactaag tctgccagac taagacagtg gccacccctc   15060
cccctagggg ctcaggccca gggagatcag agttctgtcc ctgagcccca ggctggagtt   15120
gttggagttc ctggagggat gccctgccca gtgaggaggg atgggtcagt cctgaagagg   15180
cactctggcc gcagtttgcc acagctggtg tgttgggctg tggggggatac ctcttgggaa   15240 caagccatct agcctccctg gctccagcag gggaaaagca tggcctgcag ttatagagat   15300
ggctgccacc tttcctttgc cctgggaact tagtgtgtta ggcagcgatc agtcccaatg   15360
ctggctgccg cctatctccc aaggagctca gatggcttaa acagcaggca gccacagctg   15420
tgatcctggc cacccttcc cctgggagct cagcagcctt aaggagattc tagctgaatg   15480
gctgttgaga atctgtgcag ctctgcggtt gattgagacc ctaggcccca gtggcatggg   15540
ctcatgagtg ggatctcccg atctgagggt tgcacagttc tgtggaaaag cactgtttca   15600
caggctaggt agcagctcac tcaccgcctc ccttggctgg ggggtggggg cttccctgcc   15660
ccacagctct caggggggcct ctgcaccaca ctgctcttcc tctccatggg tctcgccagc   15720
tgcctagtca attctgatgt cagaacctgg atacttcagt tggtgttgca ggatttgctc   15780 gctttttttgg ttctttttcca tgggagcctc ctatcactgc tgcttctagt cagccatctt   15840
ggccctgtcc tgcgtgacat cttggtgttt tgaggcaggg agacttttgg ggctgaggag   15900
tactgggatt tcaatgcttt tttagataca cacgttttca cgatggaagg tcctccagca   15960
ctgaggctga atctgagcag ggctttatcc ggaaactcta tcttgggtcc tgaggcccgt   16020
actgtgggag gggtcctggc cagggcactg aggcctcctg agctgtttcc accacatttt   16080
ttctgaagca cccaccccca gaaaagctgt tctcaaagcc ccaaccctat ggggcatgac   16140
ctttgccagg ggactgggta tgagaatctt ctggagtcat gaagagttca gatgcccagg   16200
cccatgtcag atcaattaaa ttggcatttt taggcggatc ctgggtccag gtttgtaaac   16260 attttttgtca aagtttccca ggtgattcta atgggtggcc aagattgaaa gccacgagac   16320
tccaccccaa accctatgta tccttgaggc ctggaggagc actggcccac ctgagatgtc   16380
atggcttcgg catcacatag ttcacattta tggaacattt actgcattcc aggtgctgct   16440
ctgagcatgt tacacgattt aactccttca gctctcccta cagtctgtga tgtcggtgtt   16500
```

-continued

```
atcatcaaca gatgaggaca ccaaggccca cagtggtggt tgccttgtcc caggtcacag    16560
agctagaaaa tggcagagct gggaagtggc ccaggcagtt gagttcttgc ccatgctctc    16620
ctaaccactg ttctgccgaa gctcagtgat aaaccaaaca cctccaccat tagaggctct    16680
gtgcacatcc tctccgatcc tcacagaacc tagagtaggg gccatgatta tcagcatcac    16740
acagatggag aaactgagga ctcaagggaa ggcaagactg gcttaagatt acacaacctt    16800
gaaatagcac ctcaatttgg ggatgcttag aatgtgctag gtgatttaca gagagaacct    16860
caaatcattt tctttctctt aaaggagttc atgatgatca ccattctaca gaagaggaaa    16920
ctgaggctgg gagaaatgaa ggcactgtct ccttgtcctc catgtgtccc agtgggcacc    16980
ttctgtgtcc caccaagcat tcatgtccat taacagagca agtgccctga attcttgagc    17040
cccaacactg actgcacacc caattgtccc ttcgagattc ttgacttcat gcaattcaag    17100
ggagaagcct ccctcctggg tgcccaggcc cagatacact gtggccagaa acaaaacact    17160
gtaggctcct gtcagcctga ggggagcatg gaaacttgct cctatgggcc ccacgcaccc    17220
cgtaggaaat acctcatctc ctcatcctta gtcctcagca ccaagaagag gtgggcatgt    17280
gctccgctga gctgcaggag gcccagctct gctccataga tgctgctgag tgaaggagaa    17340
acagcacaac atggggggag agtcctaaac gcttcatgtg tgctgagacc tgtcttttag    17400
aaacaggctt gacatatagt gaaccatctg cagaaccttt ctaatgagag ggtaaagcca    17460
gcccctccta cccctacagg acttttttc atttgttttg ttttgttttg ttttgatgg     17520 agttttgctc ttgttgccca ggctggagtg caatggtgca atctcggctc accgcaacct    17580
ccgccttcca gtttcaaacg attctcctgc ctcagcctcc cgagtagctg ggattacagg    17640
catgcgccac catgcctggc tactttttta tttttagtaa aggcggggtt tctccatgtt    17700
ggttaggctg gtcttgaact cctgacctca ggtgatccac ccacctcggc ctcccaaagt    17760
gctgggatta caggcatgag ccactgcacc cagcctcagt ttcgtcttta atgctttctcg   17820 ctatagaact gaacaatgcc agagtccgga aagagaaggt tggagcattt ctctacactt    17880
gaaaaaccac atctgagtga gtgttgcaga gacaggggct gtaagtcagg ctggtgggga    17940
ggaaatcttg gctccctgac ctgctcacca ctcagatctc ctctctgagc ctcagtgtcc    18000
tcatctttaa agaggcaaca aatggctccg ccctcatagc actggttata agcagacttt    18060
ggcacaactg ccactccctg gcccccttcc ctgcctccct cctttctcat ccaggtcatc    18120
atttaggctg agagcatggc aaagagggggt gagcaccata ctaggagtta gcatatctga    18180
gtcacacctg agctactttc tggctgtgac tgcctgggct ggggaggcac catctggaaa    18240
cttcggtgtc tttgcctata ttatctgatc agggtaaatc cacttccaca tctatgttca    18300
agggtggtgg ggagccctgt tgctatgtca tctaggaggg aaattagata atattctcat    18360
atatgaaaat acacacaccc tctgacttag caatgtcact tccagtgggt gtctcccacc    18420
tgaggagggt gatacatgta caaggccatc cactgcagga ttgttagtag ctcaagtttg    18480
ggaacaactt acatacccat caacagaatg ctgtgaaata aattttgata tttccataaa    18540
ttggagtgtt ctgcagctgc taaagagtgg agcagttcta tgtcctgacg tggaatctcg    18600
atacggaatg ttagggctta tgtttggaag aagtttttcca atcaccaatg ggctttagtg   18660
tctgaatgtg aggtgcattc tgaacctttg ggaaatggat gaaaaaagaa atcctggctc    18720
cctgatccat ggttctgttt gaggagcttt tatttagtac ctgtgatgca ccaggttctt    18780
ctatgaagac agtgtctaac aaacactggg gaaggaagga gcctgcctct attcggacct    18840
tgactctggc tttgattcca tcaataactg gccatgtgac tgtggacaag gcccctatca    18900
```

-continued

```
tctcttggct taagtccccc atctgtaaag gggagttggg ctgaaagtct gaaggtcttt   18960
cccgtgctga aattccagga ttcaggaggt aggatgagga ttctgggcct ctggctggaa   19020
accccaaata agtttttattg ctgctttaaa ttgggcaccc ctgagccacc catacgtatg   19080 acctctttc tgaggtgaag gatattctga gatgacccag ctctgctcag agcccacagt   19140
gactgtatga ctcagtcctt aaatcaccca aggcttcaaa tagacccaca gcaaatgcga   19200
gacttattgg catctcctcc caccgggcca ttagactaaa cagtgaatct gtgcctccca   19260
ggaatcttcc ctgtgtgatg tttctgaaga ttaaataaag aaaaacacga tttacacttt   19320
ccatcccctg gatgaatttc tcctcattag aatggaagag aatgtaagct tggtgtgggg   19380
aagagctatt ggctgtttca ttcactgctg tttgcacagc atccagggcg gagtctggca   19440
cacagtgggt tctcagtgag tgcctgttgc aaacttaaag tataataaaa taaaataaat   19500
aaaaaaaaat aaaaaaaaga atatacttgg ccagcctgag agagaagcgc tctttggagg   19560
cagaaggtga gttctggccc cgtacctggg caagtcactc aatctgtcag tttcctcatt   19620
tgtggaacca aagggctggg ccagattggg aaggacaaga gctgtagagc cagacagatt   19680
gaagatgtag tctctcccat catttactag caatcattta ccttgagcaa tagcatgatg   19740
tccctgggct tcaactcacc tgatctgtag aaggggggtga caacaggtct tgaaaatgag   19800
cactgaaaat cacacctgat tgttgctcaa agaatggaag gtgttactat tgagttattg   19860
tcacacatca ggggatgagg gaggtccatg ttgtactcac cacccaaagc catctcagtg   19920
cctggtccag acttaaaactc cacgttctca gggctccctt ttcgaaactt cacacagtag   19980
tatgtgccga catctgctgg ggtgatgcta ctgatgcgga tggaaaagtc catgttgttt   20040
ctctttgtga ggtctgaaac tgttgttacc ctggggaagt ggccttcttt ttgattgtag   20100
attaattccc ggcctggtcc aactcctctg aaccacagga cgggtcccac gggaagcagg   20160
gaggtcacag tgcagtgcag agtggctgtc tttccaactg tgaccaacag gagcttctca   20220
ggctgaatca tctgtagctc ctcctcacct gccacttctg aaaaggagca caaagcaatc   20280 atttttttcat ccttacataa tcctgtattt cctcatgttt atcaaagata ttcagtgact   20340
gggtgcacat caggaatcag gagcaggact tgatctcagc acactgcatg tattatctca   20400
tttaaccctc acaacatgcc tataacataa gactgtatta caattgaggg cactgaggcc   20460
tgaggcacag agaggttctt ttttttttttt tttttttttt tttgagagag ggtcctgttc   20520
tgttgcccag gctggagtgc tgaggcataa tcatggctca cggcaacttc aacctctcag   20580
gttcaagtga tcctcctacc tcagcctcca gagtagctag aaccacatgt gtataccacc   20640
atgccaggtt aagctttgta tttttgcaga aacaggtcac accattctgc tcaggttgcc   20700
cttacttgag tgcaagtgat ccacttgcct cggctttcca tagtgctggg atgacaggtg   20760
agaaccatca agcccagcca agggattcaa tttcaaggta gagttttggg ttgaggacct   20820
gaatagaact cctgaactct actttgaagt gtgtatatat atatatatat atatatgtca   20880
tataagtgtc atatatattt ttatatattt tatatatata tatgtattta aaaactgtca   20940
gtaaagctat gcgtcttttg caggctagtt tttgcctttc caaattctag aggctgccca   21000
cattcctttc tcactgttac atcttcctat cactctaatg tcttgcttgc atccttacat   21060
gtccttctca aagaattaat ctcctttctc cttcttataa ggacccttct gatatgttgg   21120
gtgcactctg acactagacc cagtattaaa accactgtct taaaaatgct caaggaagta   21180
aaggaaaaaa tggacaaagt actaaaacag cagggatata aacacattca caaaacaaga   21240
```

```
acatccagaa tgagaaatta taaaaagaaa tccaacagaa acttagaagt tgaaaataca   21300
acaattgaaa gttcagtaga ggggttcccc aacaggtgtg aacaggtgga agaaaaatca   21360
taaagctgca agatggaata attaaaatta ttaagactga gatacggatg gaaaatggag   21420
tatagtatag agaacagaat ctaagggaat tctgggacac tatcaagtgg attgaaatac   21480
acattattag agttccgggg aaaaaaaaga ggaagagaaa aaagagcaga agattattgg   21540
aagaaatcat ggtcaaaacc ttcacaaact taataaaata catgaatgca caaatttaaa   21600
gacactgaag aaatgcaagt ttaactcaag gatagaatct gagacccaca ctaaggtaca   21660
ttataattca actgtcaaaa actaaattca aagaatcctg aaagcagtgg gagagaaacg   21720
attcctcaca tacaagagac cctcagtaag attatcagct gagctcttta tataaagtat   21780
tggaggtcag aagacagagg gatgatatgt tcaaaatgct gaaagaggaa aaacctgtca   21840
accatgaatt ctatacctgg cgaaagtgtc cttcaaacac aagggagaaa ttaagacatt   21900
ctcagataaa caaaagctaa gatagttcat gaccacaaag gcttgcttac aggaaatgct   21960
aaagggagtg cttcaggtgg aaatgaaatg atgccatatg gcaactcaaa gttatatgaa   22020
gaaataaaga tgtccagtta tatgtaaatt tttttttaaaa aatcatattt acctgatacc   22080
tccacatccc acaaacaagt tgtgagcacc ctgccaaacc aggtacacca ctgtgataaa   22140
gctggtccct gccataattc ctcttcttgt cctcctcttc tgtgacttag tgacactgaa   22200
acgttctagt aaaacccatc atgcttttc ttggtgtcct ccaccctgac tcccattaaa   22260
ggcaatggct tctcatctct catctctctt gcttccccat ctgcttggtt gagcctactc   22320
cctgggagct cctcccatat ggcttcctgt gtggcatgcc ctacccagct atgcctctcc   22380
agatgaaatt ctcatgacca ggttagagtg atcctttaag acacaacctg caggacttac   22440
tctaccattt tcaacactaa tggcaatgag gaggggatta ttctaaaccg gggtagcaaa   22500
ttcctaggag atgcactttg actgttcatg gcttacggat ttgctactga ttggctccac   22560
aatttgagaa ggttttttttt ttgccctgat gcctttcttg tgttgtgcta tgcacagcta   22620
tgtgttgcct tttggagtgc tgccaagact ctctatccta aaatgtgtat cctattccaa   22680
tatcaataat gacagctgcc tttcttcaag agcacaggat gttatagcaa cctcttcaaa   22740
gaagactcat gtgatactta taataatatc acataatcca gcatctctga gttgtttga   22800 ggtgccagtg gcaatgtatt ctacatttac aaattttact tgcaaattaa aatcaacagg   22860
cactcctttt agtgctttca aacaaacaaa aataacctctt ctctctagag actttggcaa   22920
tgattttcat tcctcttgga atttctagac cactcctgat ggtcataaac ttccccaggg   22980
cttctaacgc aaaacaaaaa ataaaacaaa acaaaaaagc ccctctctgc cttgttcttt   23040
acttcattct aacaaaaaat gactggttat ctactagaat ctactggctt gtggtccaga   23100
tctaggggga atatttcctg ttgcaagcat taaccactgg ttgtctcaca ggccagtccc   23160
tgctcatctg aaatgggtcc cactggaact taaacttcta ctgaaacaca aaattaaaat   23220
ttgtcaggtg cagctgcaca cctttctgtt gacagtggcc ttattactac tggatttgtt   23280
gatgcaacaa tcctcaacca aatactagct aactgaattg aacagcatgt aagaaggatt   23340
ataaaccatg aacaagtggt atttattcct ggaatatgag tatgtttcaa tatacaaatg   23400
acagacaaac aatatggtat tctacaaata tttatttata gaataaatag aaaaaacaca   23460
tgatcatcta tttttgatgca gaaaagcatc tggtaaattt gtacatctat ttacgatgaa   23520
aacaataaaa aggatatatg aatactttca caagatgata acattcacct actcatactt   23580 tattttttatt gcacttatca ttgtcaaaaa ttaatttttt cattcaccta tttatcatgt   23640
```

-continued

```
gtattgatta ctgtctttct ctgcagtgga tgtaagcaac aaaagggcaa ttactttttc   23700
tcttttattc taccaaagta ccccatgttt ttatgtcaga tcctggcaca tagtaggtat   23760
ccaatagata tgtgtgtaat gtttgaattg ctcagtggga catttccctc gaagactgaa   23820
atcttctatt ttaggtggtt tgctcctgtg gaatttgaca gaaaatgagt ttcccatgta   23880
gaggacttag tgaaaaaaaa tcagtttgca aacatacaga aagtagaaga gcccagagaa   23940
gaaaaccaca atctcccttc acaccacatt gcccactcca cacccaagag cagcagctgc   24000
agaaatctca tggaatagaa tcaagaccgg aagtgtttga gtaatggtga aacctgtgac   24060
ctctagagtc agagtgcctg agttcaaatc gtagctctac cagttaccaa tgagtgagcc   24120
tggagcactt tgtgcttctg ttttcttatc tgttaggaaa ggtgacaaga atatctacct   24180
tgtatataat gatcacatga agtaaaagag gtaaggcatt ttcaacagtg tctgccacat   24240
ggtgaacgtt caaaaattgt aaagttattg ctcagtagat ttctgaggct tggaggcttc   24300
agtggacatt agatgacaag gataaggata agggtatgga tatggatata aatataacta   24360
tagttatagg taatataggc agacctgtgt cacctgtatc cccacatttt tttcctcatt   24420
tctaccttca tggaagaggg aatttcagga taaaaatgca cagaaattct gctttgaggg   24480
aaaatgcatt ttaccaagag agaagtttgc ttatctgttg cttctattaa cagattggag   24540
gactttcagt ggtaagatta gagaagtagg aaggagggag agtggctggg caatagggaa   24600
aaccacacat ctcttcaatg tgcatttcat atagactgaa aaaatgagtt gaagtttaca   24660
gtaaagaaag tctttaaaat tctgtgtgtg tttcagcatg gtcacatgag atttatctca   24720
ggaatgcaag gatggtataa cattcataaa tctccaaatg tgatatgcta catcaaggca   24780
atcttgagca aaaagaacaa agatggggcc gggcatggtg gctcatgcct gtaatcccag   24840
cactttggga ggccgaagcg agcagatcac gaggttaggc aatcgagacc gtcttggcca   24900
acatggtaaa accttgtctc tactgaaaat acaaaaaatt agccaggcat ggtggtgcac   24960
acctgtagtc ccagctactt gggaggctga ggcaggggaa tcacttgaac ccgggaggtg   25020
gagattgcag tgagctgaga tcacaccact gcactccaga ctggcgacag agcaagactg   25080
catctaaaaa aaaaaaaaaa aagaacaaag atggaagcac cacactgcct aatttcaaca   25140
ttgactacag tgtcaaagta atcaaaatgg catggcactg gcataaaaag agatatatag   25200
accaatggat cagagcagag agcccagcaa taaactcaca cattcacact caattgacta   25260
ttgacaaaag tgtgaagaaa acacaatggt gaaaggtctg tctcttcaaa aagtggtgct   25320
gggaaagttg gatatccatg tgtaggggaa tgaaattagg ccttcttctc atgcctcata   25380
caaaaatcaa ctcaaaatgg attaaagatt taaatgtaag atctgaaact gtacaagaac   25440
tagaagaaaa gtttcatgac attggtcttg gcaatacatt tttggatttg agccccaaag   25500
cacaggcaac aaaagcaaaa atagacaaaa ggcattaaca acaaactaaa aaagcttcta   25560
cccagccaag gaaacaatca acagagtgaa gagacaacct atagaatgga agaaaacatt   25620
tgcaaaccat acatctgata aggagtcagt atacaaaata tataaggaag tcaaacaact   25680
caaccataag aaaacaaccc tattaaaata tgggccaaag atccgaatag acatttctca   25740
gaagaagaca ttaagatggc aagtcagcgt ataaaaaaaa atccaacctt actattcatg   25800
agataaatgc aaattaaaac cgcagtgggc tatcatctca cacctttaag aatggctatt   25860
atcaaaaaga ggaaatttag tattggagaa gatgtggaga aaagggaacc cttgcagaca   25920
gttggtggga atataaatta gtagagccat tagtgaaaac agtatgcagg ttcctcaaga   25980
```

-continued

```
aattaaaaat ataactctta tctgatctgg taatctcact actggcatat atccaaagga   26040
aatgacatca gcatgtcaca catatatctg cactcccatg tccattgcag cattatttac   26100
aaaagccaag atatggaatc aacctaggtg tctatcagca gataaatgga gaaagaaaat   26160
gtagcatata tgcacaatga aattctaatc agccttacaa aaagggaaac cctgtcattt   26220
gcaacaacat ggatgaacct ggaggacatt ctgctaagtg aaataagcca ggcacggaaa   26280
gacaaacact gtatgatttc acgtatgaag aatctaaaaa gttgagctca tagaagtaga   26340
aagtagaatg gtgtttatcg ggggctagag aggggtgta gttggggaga tattagtcaa   26400
aggatacaaa atttcaattt aaataagaga aataagttca agatatctat tgtacaatgt   26460
ggtgtttata cttaataata tgaattgtat tcttgaaaac tgctgagaga gcagagttta   26520
cgagttctca caataaaaaa tgataaatat gtaaggtaat gcatatgttt attagttcaa   26580
attagtcatt ccacaatgta tgcatatttc ttaatatgtt gtacataagt atacatactt   26640
ttgtcaaata aaaataaaat aaaatattta ttttgttaaa aatttcactg aaaatagaaa   26700
gagaaccaat gattaaaaat gaaatctcat ctgtgcatgt acatgtacat gcataggcac   26760
atgtgcatat atatgtgtat ataatgtgta tatatacaca ttcacaaata tatataaaag   26820
tttggcttat catgttagta tataaggttg ttttgtgcat taattacaat tatgacaaat   26880
ttaaaaatct cagtaaaata tttggcacat agaaaccatc caacacattt ttaacatttt   26940
gggaaaacat acatacacta gtgttttacc tctgattgtt tctgactggt gtgatgggtg   27000
attattaatc taatgtttgc ttgcctgcat tttctaatat ttctacacat agcataacat   27060
ggttaaaagg gtgataaact ctggaactgg tcaacctgga cttgatccca actgctccat   27120
ggactgaagt aggggacaat gaacaggttc ctgcctctgc ctcactcccc atttgcaaat   27180
agagcacaag agttatagct tccacacagg gatgctgtga ggattagttg acttaataca   27240
cacaaaatgc taagaagtgc atctgcctta caggaagaga gcaattgctg aactattact   27300
gctgtcattt gggtacagtg tatgtgtaaa aaaaataatt tgaaaagtga gaccttgccc   27360
tctaagacct gtgagatgac atcacagcag ggcccagtgg gcaactgaga ggctattgtg   27420
cccagccctg tgaccggggg tcagctgcat ggtctgaaaa aggggtgaag acaggcagcc   27480
tgtctgggag ctgtgaacag ggctctctca ggtggcacca ggaaagacct cccaatcctg   27540
tctgcctggg ggaagggaaa ataaattctc cagaggaaag tcaagatgac caagggagat   27600
ggtggtgcct gttatgggct gaatgtgccc ccaaaacgaa tgggttgaag ccccaatccc   27660
cagcgcctta gaatttgacc atatttggag acaaggtctt taacccattt atgcccgagg   27720
ttgcaatttt ttttaatttt gaaaaatcag accttggcga tgcccttgag cagtaggata   27780
taaataactc ccgcaagctt agtgatccaa taacggagca ctaggcataa atgggtgaag   27840
caatttagtt aaatgaggtc actggcgggg agccttaatc caatatggct gatgttctca   27900
taagagaaaa tgagaataca gacacacaca gaggaagacc atgtgtcaag acacatggag   27960
gagatggcct tctacaagcc aaggagaaag acctcagtag aaactaaccc tgctggcatc   28020
ttgattttgc aattcagcct ccagaactga agaaagaaa gtaaatgtct attgtttag   28080 ttactgagtc tgtggtgctt tgttgtggaa gccctaagaa aggaatatag gacgctgtaa   28140
gcatgaaatg tggaacttct taaagaggag gagggcacac aaaaatgggt aggaggactc   28200
aagacaggta aggatttaat aatgattctt ctgtgtttgt caaataaaat attataaaaa   28260
tgtaactaat tgtgatggtg gcagaagcct cacaaggttt gatgcctctg gtagccagct   28320
gcagatccac agagaaagtg ctcagctccc tgatcttctg ctcttggaca atgtccagtc   28380
```

```
cttgaccttc cttggcagtg cttgtgctta tctgaaattg ctgcaagtcc aggggcaagg    28440
ctaggtccag gaagcaggga gaaagggttc tagcccaatg caatgctcac ctgtaagtcc    28500
cagcagtaga gtcagaagca ggaaaggacc aggaggatgg ggccaggagg ctgggacagg    28560
cattttggag acctcagaag cctgctctgt tcaaacgtct gttctgggga gatgtcaggc    28620
cctgctctga agacagaaga caagccctgc ctccctcaat tcaagaggaa gtggctatga    28680
tggaatgcaa cagtaacctg cttctagatt gtgacttaca aatcaggcac agtaggcagc    28740
tacaaagcaa ggagttaatc gtgctccatt ttcaggataa tcagacaggg ttagcagaaa    28800
taatgcttcc tgcctgcctg ggacctgtgc tccctcctcg tgtccccaaa cccatttttca   28860 ggtcttcttg gtgatttgcc atttgaggct tttaagtcaa gaaagatctg ttgttaggta    28920 ttgtttttcta aagtctttat ttcaagaccc taggatgtgg ttggcttgtg gtcttgttct    28980
gcaccagcct caaccaaatg ccactccgct ggacgtagga gaagagttca caggacctgc    29040
tcaacactgg agaggaacca gatcttctcc tgaaatgatt ttctattcca aattgctata    29100
attggcaaca cttagcccaa attcagtctc ttgtggacct tagcactttc atgtgcctgc    29160
acccagcaga aggaattatt tcttgactcc ttccaggaga gaaactgggt ttgaggtaat    29220
aagcaactgc tttgtggagt gaggtgggga ttgtgggtta tggaaagggg atagggttat    29280
catgagggaa gattatggtg ggcaggttcc tggggccgtc gcatcaattt caataccctt    29340
tcttctacac acagagcacc tatttcattc atcactgagt tcggatggga aatgaggaaa    29400
gaggaaaaat ccatgctcct gccaagagtg tgtgccaagg agttggggaa gtcgctgggc    29460
cctcctatgc tcagtttcaa tctcctaaac tgggaatagt aagtcttttt gtgcagtgtt    29520
ttagtgacga ttaaagaggt aatgagcata tcatgcctga aacccagtag gtcattattg    29580
atactcacgg tgccaggtga agtgcgggaa ctcaaatgtt gcttttgaat ggatccctcc    29640
tgcatgctga gttgcccacc agtggctttc tcccagcaac ccaggcctcc tgagacccag    29700
cttatatagt gtatttggac tctcgctgcc accctgaaat cagtttctcc ctctggattc    29760
tctaaatccc gctccttgtt caaccataga ttaattcctc ctcttacaat ttccagctgt    29820
gtgattttca aaaagacact acttctctga gccttggttt gattgtatgt aaataaatgt    29880
tagaatatgc accttgtaga gctatggtag gaataatata agccatactg aatgcttgac    29940
tcataattaa ttataagcaa aaaaacatgg ctataattat tttctgtgta caggaagagt    30000
ccactggttc tctgccaccg ttgtgcctta gaaaagccac cttgttaaaa gaaatgattt    30060
ctcttccagc atctatgact aagaaagacc tgtccagaat ccttcatctc acatgtgggt    30120
tttaggttct taatctgtca tgaataattg tcaaatcaaa ttgtaaatgt tatcatgttt    30180
taattgaaag tcctgtttta atgtggcaga tgtacacagg gtgaaatctt cccctccttc    30240
tccacaccca cagtagtgaa aacacaaaat gaaaagaata tatgaatcaa tgtctaatta    30300
cacttgaata caagcaattg gcttctatat gacatgaagg aattataaca gctatcattt    30360
attgagagtt tcctgtgctc cagatatggt gccaagcatt tttctattgg taatgtcatt    30420
aaatcattgc tctgaccccca tgaggtaagc tcaaccatta acctcctttc acaggtgaga    30480
aaacccgagg cacatggaga gtaatgaatt tgctcaagat cacccggctt ttagaactgg    30540
aacataggct gccacactcc acagccttca cttttaatgg ttgtactatg atacctcttg    30600
caggaaggga gagacatccc tcaggaagaa agcagagaag aagctatagc ctcaattagg    30660
agcagccctc atagtgaggc tggggcaggt gccatgctcc acgaggccct gacaacccat    30720
```

```
gatcacatgg ggaattattc ctgggaagac ggaagtgcaa gcaagaatca ccaaagattt    30780
gaggaacagc actgcagcta acaaattcaa gaaaaacaat aactcaaaaa caaatagcaa    30840
tcaaaagaac ttcacacctg agcaaatatg aaaaaacaaa atgtgtaaag ttctttaaag    30900
ttagtatact taatgatctt ataaggaaaa caaaagagaa gtaaattcat aaaccaacat    30960
caggcatgta ataatatgaa acagaaatag gcgggcatga ggtaacaaca accatcttga    31020
aaaaatacca aaacacagac tttggaaatg aaaacataat cagtgctgaa attttttaaa    31080
aaaacttaat aggttgacta gctgactata cataaataag tataatagta agttagtaag    31140
ctgggtgatt atgtagggga aatttcctgt ggtacagcac agagacacac ccaaacaaag    31200
taatgtggat aggtaaaaat ataccacaat attgtggtat atcttttcct attgctctat    31260
ttttacctat ccacattact acattacttt gagaggtgtg agtcataaag tattatgtct    31320
ccaaaaataa gaattgggcg tatatgactc aaaaatgcat agtatagtgt caggaagatg    31380
gcagaatctg tgcttagagc agcaagtgcc ttcctgtgaa cttcaatcct tcagtaaaga    31440
tcaactaagt acacagatgc ttacaatttt tgtggaaatc acgtggagaa ttgaaattta    31500
aatttaggtg acttggggaa gcatagataa aatctgaatg tttgagagga ccaggaacct    31560
gggagtccat gagccaaaat tctcctttat ctgccatatt tcaccctgac tcatcacagc    31620
aggtgcagat aaccagggac gactttggga cacatgagaa actgggagcc agtggatgct    31680
ccagaagact aaagatgtaa gactgtgggc ttaagaatca aaacttcctg gtctgaaatc    31740
cagctctaat gggtcccagc tgtgtgatcc tggggtcact attaacttcc ctgtttcctg    31800
agtttcccca agtgtacaac ggagagaata atcataccat cttcataagt ttgtgatgag    31860
aattaaatga actaatatat gcaaattact taatactatc tgaccatgtc ctccaaaagt    31920
tatatattca gtattaccat tatcattata gatagtagtt agatattatc gttattaggt    31980
agtgttttgg taatagcaac aattttaaaa aacagatcct ctgccctcaa gaatttatga    32040
tgctgtgtga caaccttggc cagtggctgg tggaggtgga gtacgacgat gatgagctga    32100
ggtcatgtgc ccagccctag aatcatggag tcattaccag caccaggggc atgctatagg    32160
catgacgtct gggggaatca atatgacccc agtaagggtc tactcaaatg ctcatggaaa    32220
agctgttcca aatcttgtct catgctggga tgggagagaa gaaaatgctc ccaaatgtaa    32280
atcaatagga gcaggtaaca tgggctgaga gggtgaggag acaccatgta gaaatacact    32340
catgtagagc aggctgcact cactcacctg tgagtcctgg tagcagagga agtggcaggg    32400
gctgtccaga tgggctggga gacagggatg gacattgcct gccctgtcag actgtctcat    32460
ggagagaatc cagactctac tctgcaggaa aggagggcat ctgcttatct gctatgttgt    32520
ctgaggagtg aggtagctgt agggagaaag ggccatgaga ctgggacaat cctccattgt    32580
gaaagaggaa gtggacacag ttgccatctc tgggaagttg tggatgtctg tgcttggggt    32640
tcccaggcct gggtagattt agccagtact ggagagaggt ccactgcccc agaacctgct    32700
ctctgtttca gaggcactca tctcatgcca ggggtcccat gacccttcct cattgacagc    32760
ccagaccaag agggctctgt agctaaggac tgagcttgca atttcagaga ccataattcc    32820
agatgtggca catttgaggg cttgtggctg tagcagcttt ctgggatgaa acccagtccc    32880
ctgcacaacc cctgcaaaaa gtcccttaag tcaacaccaa ggaaccagct gagcaaatca    32940
aaagtgacat ttcttcttag atctgtcaga aaaacgaggt cacagggcaa accactgtcc    33000
ccagaattga ggagttgggc agggtaatat agagaatcac aacttcctga agccaaaacc    33060
tctgtgggaa ccagtgccgg ggaaggaaag cctgcactgt aattgaagaa tttcttgagg    33120
```

```
ctcagtgtgg gccagtctta gacacaaact cgaggaggac ccaataacgg aggtctccca   33180
cacttttgtg agttttatct ctgggagctt ggttagctcg tcagagtgaa tataggagaa   33240
atattcactt gtgctcccag gacacggaaa ggaaaagcaa tcacttaaaa atataccaga   33300
gtgtcctatt gttctttcgc ttgttccata tagtaaatat gcaagacaaa ggcaagcact   33360
gttccaacta ctgttgatac atttttagaa agaaataaaa caatttaact ctcaatgttt   33420
ctaatgcttt gaattacagt atactaaata tttgaacttc ctgctacatt tctaactgac   33480
aatatgacag tttctaatac tttgacaaca attatgagga tcacagaaca accattattt   33540
ttcccattga atgtagagtt gtttaccagg gcttcatggt ttccagttat ttttacaatc   33600
ctgcactgcc atgcaaagtg aggacatgca aaataagtac acgtggtaat ataatacagt   33660
gctgaggaga aaaactgatc aggataagag gaattgaaat tctagggtag gagaggaaaa   33720
tgactatttt tcctcaccat ggtttacaaa atgtgtcttt aataaagtga aatttcagca   33780
gaaacttact tgaaggaaag aagagagtga gccatgcagc tgtttttgggg aagactcaga   33840 ggaatgacag gatttgactt ttcaaaaaaa aaaaaatcat ggcccggcgc ggtagctcac   33900
gcctgtaatc ccagcacgtt gggaggccaa agcgggcgga tcacgaggtc aggagatcga   33960
gaccatcctg gctaccacag tgaaaccccg tctctactaa aaatacaaaa aattagccgg   34020
gcgtggtggt gggcgcctgt agtcccagct actcgggagg ctgaggcagg agaatggcgt   34080
gaacctggga ggcagagctt gcagtcagcc gagatcgtgc cactgcactc cagtctgcag   34140
cctgggcaac agagcgagac tccatctcaa aaaataaaaa aaaatcatcg tgactgaaaa   34200
ctgcaatcca gtagagacaa tagcaacagt ttggaagaga tgatactgat tgggaccagg   34260
aaggagcgat ggaggtgaga agcacgcagg ttataaatat aactcagtgg tgtactggag   34320
caggcttggg ctggttcaag acagccaact gtcaaacttt aaggaatttt gcaatctggt   34380
tgttaaactg ttggaagctt gaaactggct acattgggag tatttacact atcaaaattg   34440
acaagcgcta taaatcggcc ttctttttcc ttttgaagag tcaactgtta tacgtttatc   34500
atctcatcag tggacataag cactttgaag gcataattga atgttgcgtg taaatgaaaa   34560
agaaatcaaa gaggactcca aagctttttga actgtcgcgg cattcctgcc atgagcaaca   34620
gggttaggaa agttgcagat tgtcagaaac aactagtgtt tccatcccag agagaggagg   34680
gagaactgct ttctttttag gtgtgaggag taggacactg tcttagtcca cgtgtgttgc   34740
tataaagaaa tacctgaggc tgggtaattt ataaataaga ggtttatttg gcttgtggtt   34800
ctgcagactg tacaagagca tggtgtcagc atctgcttct gatgaggccc tcggactgct   34860
tctactcatg gtgagagaca aagaggagct ggcatcacat ggtgagagag gaaggaagag   34920
agagagagaa gagggaggtg ctaggctctt tgtaacaatc aaaccttgtg aatactaatt   34980
gagcaagaac tcagttatta ctgcagacgg caccaagtca ttcatgatgt atctgccccc   35040
atgactcaaa cacctcccat caggccctac ctctaacata ggggatcaaa tttcaacatg   35100
ggatttagag agaacaaata ttcaaactat cttggatgct aaacaaaga ggaaagagaa   35160 ctgttttttt cccttaaaac tgggatgggg gttcatttgt attcaagagg caatagagaa   35220
cctcaacaag gctggggaga tggagtaggc gggaatccag aagacagaat aagtacggaa   35280
aagctggaga gagtctgtgg tttatggcct gtctcaaagt gatggatgca aggaatccta   35340
gtgtattcag atttgatgtg tttctcacat tctagggggga tgctgtgagt cagtgcccag   35400
agccccattc cttggcccct gctcaggacc atgtgtgaag actccactct ggggcatcaa   35460
```

-continued

```
ggtggcagag actgagggtt ccacatggca ggggaggaag gaaggagctg tgggaaaaca    35520
cgtccaggtt taatcatctg ctcatccttc aggaaatgtt tccggagagc ctgttatgtt    35580
cccggtgctg atctcctcct gagatgtctg tggtggttgg acaggcagct ctgagatagg    35640
actgtgccag ctcagccctc ctcctgagtc ctggcgccct ttcccgcatc ccttccacgc    35700
aggcactcag aggatcagag tgggaacagc tttcagagtt gcctatctgg ggcttctcag    35760
cattactcta cagtgggatt ccttagaatg gagtccagca tcaaataatc tagaggtggc    35820
ctgtgaggga ccacctacag agttgcccct cacttagcac cctcttctca cctccccagc    35880
aggcccctaa ggcaccgtgg acacctttga acagccttgc tgtaacccac ttcctgcagc    35940
acccacacac ttcctggggc tgggagcctc ttagagggtt tcctgagact cccaagggtg    36000
cagagggagc tcggttacct tctctaaact ccactgagcc tgatgttgca tggcgtgtga    36060
gctgggccct ccggctggcc ttgcccttct gcggcaaccc ttggccagcc cttctatccc    36120
cacacttaca gtcaggcctc tgcttcagtg gatgttagat ggcagagaca tcaaccccca    36180
gcagggccct ggggcccagg aggagagcta caaggagtgg ggcagtagga gctggcatga    36240
gccctagaaa tcatgagact ccaggaggag ccatgagagg ggccacctgg gatgggcctc    36300
cgcttacccc atccaaagct acctgggccc aacaaggctc caaaacttt gaatctgagt    36360 ccttccctgg atgccctgga tccaacccaa ggcagaaacc agggaaagag gctccttctt    36420
tccagtcacc ccatctcccg gtgccaggct ctcctactgg aaggagggg ttgagagagc    36480 ttgtactcag gtattcatac attgcaagga agccatggac ttgtttctga aaggagtgac    36540
gcctcctcaa gaagagcctc acaacttagt ctaattttcc atttcccta ttgaaggtta    36600 ggttatgtat attttcacaa gtttaaaagc cctttgtttt tcttttatg tgtactattt    36660 atgtcattt gcccattat agttgggctg ctgggtcttg ttgattttta ggaacgttta    36720
aatataaatt aaaatctggt cttttttgga tatatataaa aaaagagcc tcaggcacgt    36780 ccttcaggag ggattccaga agaaggcatt gttctcctag gagatgacag ctctaggcgg    36840
gttatggccc ctgaaggcct tccagtggga caagatgcga aggtggaaga cagcactatt    36900
gctgatcctg accctgtagg cccaggctaa tgtgcgtggg aggtcttagt ttttaacaaa    36960
gacagtttaa aaaagaaaaa aaaaaagac aaagttctaa actagcaaaa acctcataga    37020
ataaggatgt aaagagaaaa aaatttttgt acagctataa aatgtgtttg tttcaagctg    37080
agtgttgtta ctaataagta aagttaaaaa attaaaaacc tcataacatg aaaatgttac    37140
agcaagctaa ggttaatata ttattgaaca aggcaaaata tttaaaaat caatttagca    37200 tagcctagac caggcattgt gtcatgtgta tgtagtccca gctactcagg aggctgaggc    37260
aggaggattg cttgagccca gaagttctgg attgagtgtg tgcactaagt tcagaatcaa    37320
tgggctaacc tcctgcaaga ggagggacca ccaggttgcc taaggtagag tgaaccagcc    37380
caggtcaaaa acggagcagg tgaaaactgt catactgatc agcagtagga tcatacctgt    37440
gagtagtcac tgcactccag cctgggcaac acagtgagac cccagctctt taagaaagtt    37500
aaaaataaaa aatgtatata catttagcat ggccaaggtg tatggtgttt ataaagtcta    37560
catagggtag tttcctagga cttcacgtgc atgcatcact aactcactga cttacccaga    37620
gcaaacagtt ctgctagctc cattcatgag aagtgcccaa tacatgtgta ccattttaaa    37680
aaatattttt aaaaaaatta ttaaaaaata ttttatatca tacatttact gcacctttta    37740
atgtttagaa atgtttattt acttactttt ttttttttgga caaagagact tgctctgttg    37800
cccagactgg agtgcagtgg cgtgatcgcg gttcaccaca cccttaact cccgagctca    37860
```

-continued

```
agtgatactc ccactactga gactacagct gtgcatcacc acacgtagtc aatttttaat   37920
ttttctgtag agacagggtc tcaccatgtt gcccaggctg atctcaaact cttgggctca   37980
agtgatcccc ctgccttggc ctctcaaagt gctgggatta caggtgtaag ccacaatatc   38040
tggctagaaa tgtttagata cacaaaaact actgtgttct aattgcctac ggtattcagt   38100
acagtaaaat gctgtaccgg tttgtggcct aggagcaaga ggccatacca tatggcctag   38160
gtgtgtagta tgtagtaggc tatcccttct aggtttatgt aagtacactt tgtgatggtc   38220
atgccaaaac caaattagct tgttgatagc tgttgtgaga ccttggttct tgtcttctta   38280
gtttaaaaga atttaaacaa gagacacaca gcaaaggaaa tgcagcatag agtaatttat   38340
tgcaaaagga aaagaatatt ttgaaagtta tgtgcagaat agatggtacc tcctgagaga   38400
gagagagagg attcaaaacg ggttgttcat aaggataaga cagcaaagac tggcactagg   38460
gaggctccct ttaagggagt cttcaatgat tattcataag gaggtggaaa gaggtgttgc   38520
aaataagcat gttctgggca gtcctctggg tgcacctgag cagtggctgt atatgcttgt   38580
tcatacattg catagctcat tagcatctta aatctccacc cagggatgtg tttttttacta   38640 ttataatgag caaagggtca gtttgaggac aggtaaagtc aaaatgcaca gaggggaagt   38700
ccctactata gatagctttg ctttaatcag ctcaattaga atgccaatgc tgagtcttat   38760
tgtattgact gttctgccat cactcttgct gcatcctgag aacagggtta cttctttgac   38820
tacctatcct ccctcaagct aatgacacat tactcaggat gtatcccctt cattatgaaa   38880
tatatgaaca tgttaaggaa attgaattga taatttttaat acttctgaaa atatatcttg   38940
aagaccagat attttcacag gagcccttte tttctttttc tttctctttt cttttctttt   39000 tttctttttct tttcttttct tttctttctt tctttctttt tctttttcttt tctttctttc   39060 tttctttctt tctttctttc tttctttctt tcttttcttt tcttttttcttt tttctttttct  39120 ttctttcttt tctttctttc tttcttttttt tgacagagtc ttgctctgtc gcccaggctg   39180
gagtgcagtg gcatgatctc ggctcactgc aacctctgct tcttgggttc aagcgattct   39240
tctgcttcag cttccggcgt agctgagact acaggcacac acccaccatg cccagctaat   39300
ttttgtattt ttagtagaga tggggtttca ccatgttggc caggctggtc tcaatctctt   39360
gaccgcatga tccaaccacc tcggtctccc aaagtgttgg gattacaggc gtgagccacc   39420
gcacccagcc tttcacagga atattttacc aaaaaattaa agaggaatta aaaccaattt   39480
tagctcacac acaccacaca aaaaacagcc atgaaagaga tttgagaaaa ttgtaaaata   39540
tacccaattt agatgatatg aggaaatttt tgttaatttt attaactgtg ataacaatat   39600
tgatcttgta gaaaaacgtc ctcaatcatc agatcaccca ggatggactc catttgcaac   39660
tgcaggtgca tgcatgactg agtgagcagt ggacgtgact atgcaccttc catgcatctc   39720
tgattatagg ggaaattgtt tgtccttcac ttcctatctt cactcttcca gcaggcaggg   39780
acatggacaa atcagtgacc cagcacagac ccagcagatg aggctaatgt cttagggcat   39840
gcaggaggaa tccaagcctt tgaaaagtct tctggagcag agacccctcc tggtattgta   39900
tgagagggaa acaggacata ttttggtcaa agagagggga atatcggcca acttcagatc   39960
cttgggacaa tgtctagcag aagggaatat ttctctaatt agcacaaatt tgccgtacag   40020
gctgatagtg gccctgtctt cagggcctca aatttacctt gattcgttta gactaatcac   40080
cttgtctaat gacaagacat cttcaacaac atcccaacat ctctcattgt tcctcaagtt   40140
ctgagtttct cttctgtaaa actccaaact actggatgtt tgaagcagga agggagagta   40200
```

-continued

```
tagatgaacg gaaatttgca cgtagtaaat gtgcagaggg atgttgcggt tattattggt   40260
caaatatcag catcaggaca cagaagaggc tcatgctgtg accagtcacg gtccccaggg   40320
ggcctggtcc agtcttaaat gccttttctg attttcccac agcagatgcc agagtctgct   40380
gggatgaggt cgcagatggg atggaaaagt ttaggacaga acaaaaatga gtcagagaaa   40440
gaacagcagg agggctgatc tgacaaggaa tggagaacat aagtaaacat ctgagacaga   40500
aggcaaaaca caggactcca tgagcagatg atctccctgc atctctcttc ctcctttaat   40560
atatatttgt gtcaaaagat ctaccaagtt gtgcatcaaa atcttagtaa tggtgactct   40620
tggagtgtgg gatttggggt agacagctga ctttaaaaat ctactctatg tttatagatt   40680
tctaggttat tttataacaa gcatgactat tactattaac attaaggaaa gagacaaaat   40740
tttaaaatcg ggagtaacct caccaagggg ggcctctgag ctctgctcct ggtgggctga   40800
gacctctagg gcaaggcttt tgctgaccac cagctgccca tcatgcgcca tctggtaggt   40860
gagcacatca tccctgtggg cagatatgtt caccaggagc cagcttgtcc agtcgtaggt   40920
gccttccatg ttctcaatga ggatggaggc tgtttctatc tgggacacat ttctgttctc   40980
caaccaggtc agctgtaggt tctaggggta gaaattcttc acctggcagg tgacgttcac   41040
ctggttccct gcctttatgg gctgttgagt aacctccaag aagggtggaa ctgaaacagc   41100
acagggcaga agctctgacc ttgtggcaca gacagatcac agggagggct ccataaagta   41160
gctcccacca ccacggtgag ggcatcacca ggacagagct aggcatgcat caggtgctca   41220
gacattgagg gtgctctttg catatgaatg aaattactaa gcacaacgcc cagcacacag   41280
taggtgctca aggactggta gctcctacta ggctaagaat gagtgaaatc tgcaagcaca   41340
acccctggca tgcagttgaa atgtcataac tgcagcaaaa tcaatgaaat caccaggcac   41400
acagggcctt ggctcatagt aggtgctcat taatcgtagt tgctcttggt gaaataaatg   41460
aaactatcta gcatagagct tgctagctat ctagcaagct agcaagctat ctatctatct   41520
agcacagatg tctaccacct ggtgggtgga catctagctg ctaccatgga aatgatagta   41580
agtgaccagt acatctaggt gcatggaagg tgggcagcac agttaggaat tagattccag   41640
gaaatccaag ccctggagta aaagccagag aggaggagca ggcttggcaa ccagatatgg   41700
gattgggcta ggagtgagga ttctctacct tgaatggttt cagacaagtt ttcagtccca   41760
caaagagggt ccccctgtaa agtgatgtgg gccacctcgc agatgacctg aaggcaaagg   41820
tctccagagg ccagcaccat cctggctgtg ctgcaggtgc tataggcat  actttctcct   41880 gcagggtcca cgttgatctg gaagcctgag agctcattcc tattttttgga ccatttcagg   41940 gtggtgtttc agggggagaa gccgtgggac tcacaggtga agctcactgt atgctcagct   42000
gtggtcctca ctgcagtgca tgataccaca ggggcagagg atttggctac aaaaggagca   42060
tcgataaaca ggagacatga ctgagatgac catcactaat gatgagtgtg tgacatgtta   42120
agaaccttca tggacattag ttttttaatcc ttctaataat gtggagaggg tggtgtcctc   42180
attttaccga ccaggctgga aaggctctga gaggtgagga agtccagacc tgagttcaaa   42240
gttctcctct ctaaacaggg tgacttccac caatctgggc acaggaacaa agttactgat   42300
tggtctccct ctgtgtatgg actggtccta gcctgcctcc cctggagagt tcaccaatct   42360
cagagagtgc cgagaccagc tcggtcaggg agaccctaac ccagcggcgc tagaggaatt   42420
aaagatacat agaaagtata gaggtgtgga gtgggaaatc aggggtctca cagccttcag   42480
agctgagagc cttgaacaga gatttaccca catatgtatt gacagcaagc cagtgataag   42540
cattttttct atagattata gattaactaa aagtattcct tatgggaaat aaagggatgg   42600
```

-continued

```
gccgaagtaa agggatgggt ctggctagtt atctgcagca ggagcatgtc cttaaggcac   42660
agatcgctca tgttgttgtt tgtggtttaa gaacgccttt aagtggtttt ccaccctggg   42720
tgggccaggt gttccttgcc ctcattccag taaacccaca accgtctgga gtgggcatca   42780
tggccatcac gaacatgtaa cagtctgcag agattttgtt tatggccagt tttggggcca   42840
gtttatggcc agattttagg gggcctattc ccaacaagag agggcattta cagaagccaa   42900
tacagggaac aatggtgaag tggtgccatt gtgagagctg gaaccaggcc gctcagccca   42960
ggagacgggt ggcctgacac atccagctcc tcttctgtaa aataggacag catttctgct   43020
tcccgggatg cagtgaggat taaatggggc cctgtttgct ttggatcaaa cacagaggat   43080
gcttcatata agtgaacaca gttctatctt taacccaaat ttcgtgaata caccgagatc   43140
tctctgaggt atttatgaat ttgttccata tagttcattc ttttcacaaa tattccagca   43200
ggatctgtga aagaaaatga agtaattaag gctaaagctt taacgaagag ccgagagttt   43260
gtaagaacat tgcacccaca cctgctaaag gtcaagccac aggatgttgc tgtagatctg   43320
agtaacaact gaagtcaagg tacgtgggat tttgatctct ctcatcctgg agtactttaa   43380
gtaaccaatg aaaacaggtt tgcagtttag aatttttgcc cagccattga attgtctcca   43440
aaaccaactt ttttgaaaat cccctataca aaaccttttcc cgcactgctg tatgagactc   43500
tattcagcac ttctctgact ctgtataccc aaagtacaat tctttatttc ccaaataaat   43560
gctatttctt ttggctttttc ggccaatcat ttgttgttgt tgttgttgtt gttagcaggc   43620
ctaatttgtg ccaagtgctg cctttccaaa gagggaacgt ttttggaatc tgggtcttca   43680
gttgggtcag gtttgggttg acaaacaaga tcactgagta ctgagaaagc caaaggtggt   43740
taatgttttc atcattagtt aactacaaga aacacagacc caggccatct aagcaggcag   43800
gcactcatcc tgcgtcctga aagcacacag attagagaat cagaaaaatg aaggcagttt   43860
ctttccatag agaggtccta aagggcacct ccaaattgtg aattactacc ctacatcttc   43920
tacaacaatc accaggaagc atatatcaca catatttgcc tttgtacata ttaacctgct   43980
ccctaacatg tgtcagacat tttgagggca cagtaaagag ggtgtcactt gaagaagaga   44040
agttatcaag ataccaccag catggcgacc ctaacgggat gagaggatgt aatcaatttc   44100
catttatggg agcctgatgc tgcctgctcc ctctatacct ctctttaatc ttttttaaccc   44160 ccctccatcc ctgtgagggg gtcctaatgt gagccccttt ataggatgag gctcagagag   44220
gaggcccggc tggccaagga ccaaaagtgg acacaaaccc caccctggta agataagaga   44280
agacaagtga aaagcacaga gcctggcatg tcgtaggtgc ttaacaaatg acccctgtga   44340
ctgttttcag gaggtttggt cattactgct tctaaatcta cacatttatc ctttaggcag   44400
cagaacaaag aggagcagaa acaccgagaa aaggctcaaa ccctgctccc tgcggctcat   44460
gacaaaccca aatgacaaaa ggagcagaaa ccaccaagtg aggattctct ccccttttct   44520
gaacaatccc ctcaggaaac aagtttggca aattggcttt caaaacacaa acaagatcac   44580
agatgcttcc ctccagagga gctatttaca gaagctggaa gcattttgga aggaatagga   44640
aacagattcc tccatgacat cttcgtgtgt ggaggcaggg aggctcctgg ggctgaggag   44700
tgaggatttg ctgggatttc agtgctgttt aaacacaaac ttgttaaagt tgttcccaac   44760
actgaggctg ggatctgagc aggacttaga ccaggcttct cctccttgtc ccctaaggcc   44820
tgctccatgg gaagggtcct ggccaggcca ctgggccctt ctgagatgtc tctggcccat   44880
gttattctga agcatccaca tccagaaaag ctgctgtcaa tgctcaacac aatggaggac   44940
```

-continued

```
cacttttgct agggggctgt gtattagaat cttctggagt cactgagaac tttgcatgcc   45000
caggctcatg tcagaccaat taaactggca ttttttttta ggagggagcc ttgggctgga   45060
tttaaatttt ttttttttcaa atttcccaga tgattctaat gagcagccaa gatcgaaagc   45120
caccagaccc caccccaaac cccatgtatc cttgaggcct ggagaagcac tgacccatct   45180
gaggtctcat agcttcgaca tcacacagtt catatttatg gaacatttac tgcactccag   45240
gtgctgctct gagcatttaa aaggatttaa ctccttcagt ttctgtcccc agtcgtgag   45300 gtcagtgtta tcatcaacag gtgcggacac tgagactcac tgtggtagag caccttgtcc   45360
caggtcacag agccaggaag taccagagcc cggaagtggc ccaggcagtt gggctcctgc   45420
ctgccctgca ctaaccactg ttctgcggaa gctcagtaat aacctgaaca acaccaccat   45480
tcaggactct gtgcacatcc tctcccatcc tcacagaacc cagagtgggt ttggtgcatg   45540
attatcagca ttgcacagat agggaaactg gggactcaag ggaaggcaag actggcccaa   45600
gatcacaaga aataacagct tgatttaggg gtgcctacaa tgtgctaggt gatttacaga   45660
gagaacctca aatcctatcc cctctcctaa aggagtcgtg atgatcacca ttttacagat   45720
gaggaaactg aggctgagag aaatgaaggc actgcctcct tgtcctccat gtgtcccagt   45780
gggcacttcc tgtgtcctac caagcactca tgtccattaa cagagcaagt gccctgaatt   45840
cttgagcccc aacactgact gcacacccaa ttgtcccttt gagattcttg actttatgca   45900
attctagaga gaagcctccc tcctgggtgc ccgggcccag ataccctgta gccataaaac   45960
actatgggct cctgacagcc caaggggaga atggaaactc ttgcttacag tggccccact   46020
cacccactac gaaatacctc atctcctcat ccttagtcct cagcaccaag aaggggtggg   46080
cacgtgctct gctgggctgc aggaggcccg actttgctcc acagatgctg ctgagtgaag   46140
gagaaacagc acaacatggg ggaagagtcc taaatgcttc atgtgtgctg agacctgtcc   46200
tttaggaaca ggcttgacat ataatgagcc atctgcagaa cctttctaaa gagagtgtaa   46260
agccagcccc tcctacccct acaggacttt ttttgtttgt ttggtgttga atgctttttg   46320
ctgtaaaaca gagcaatgca agagtttaga atgaggttag agcatttctt cacactttaa   46380
aaagcatagc tgagggttgc agagacaggg gctgtgagtc aggctgggtt gggatcagac   46440
cttggctccc tgacctgctc accactcagg tctcctctct gagctttagt gcctcatctt   46500
taacccatac cctgtttgct ccaagaatac tcttgtctct aattctaatg taacatcaag   46560
tacatttctg ttacattagg attagagaca agttctgttt agaaataact ccaagaacag   46620
tttttatatt ttattttcac aatgaaaatc agtcagattt gcttcaacct caaagagcat   46680
gtttgtgtaa aattaaatga gctctggcag tgagctgcac tgttttttttt ctttctaagt   46740 gggttaaaag aggcaacaag tggctcctcc ttcctagaac tggttatgag gagactctgg   46800
cacagctgct gctccctgct tccctccctg cctccctcct ttctcatcca gggatcaatt   46860
aggctgataa tatggcaaag aggagtgagc acttcactag gaagtagcag attggggtca   46920
cacctgagcc acttactcga tgtgattgcc tagggtggga atgcatcaac tgggaacttg   46980
cgtctttatc tgtaataact gcaaaatcag gataaagccc ccttctccat ctatgtttaa   47040
gggttgttag gagtctcgat tgctaatgat ctaggaagga aattaggcag tgttcttaca   47100
tatgaaaaca cacacaccct ctgacctagc aatgccacct ccagtgggca tttgtcacct   47160
gagtaggata acacatgtac aaggtcaccc actgcagggt tctttttaata gttcaacatt   47220 gggagcaact tacatatttta tcaacagaat actgtaaaac aaatttgata ttttcataaa   47280
ttggactatt ctgcagctgt caaagagtgg aacagctctc tatgtcctga cgtggaatct   47340
```

-continued

```
caataaggaa tgataggggtt tatgtttgga agagtttttc caatcaccaa tgggctttag    47400
tgtctgaatg tgaggtgcat tctgagcctt tgggaaaccg atgaaaagga gaattgctgg    47460
ctcttcggtc agtggttttg tttaaggagc ttttatttag ctcctcgaac atagtccgtg    47520
ttgtttctct ttgtctagtc tgaaatagtt gttacctggg gaaagtagcc ttctcttgga    47580
ctgtagatta attcgtggcc tggtccagct cctctgaacc actggacagg ccccacaggg    47640
aacagggagg tcgcagtgca gtgcagagtg gacatctctc cagctgcgac tgacatgaac    47700
ttctcaggct gaatcacctg caactcctcc tcagctttca ctttcatgac aaagcagtca    47760
tttattcatc cttacatgat cctgtgtgtt tcctcatgtg tatcaaagac tttcattgat    47820
cgagtgcata tcaggagcag agcttgagct cagcacattg catatattat ctcatttaac    47880
cttcacaaca agcctgtagc ttgttgtgac atgagactgt attagaagtg aggacaatga    47940
ggcgcagaga ggttcaattt taagatagag cttaaacatg agactgtatt agaacatgag    48000
actgtattag aagtgaggac aatgaggcac agagaggttc aattttaaga tagagctttg    48060
ggttgaggac ctgaatggag ctcctgagcc ctctttggaa gtgtcatact ttgctaaata    48120
tttttgcctt cactttctgg ccatatggag tattgcaatt tctggaccat ttcattgact    48180
gaggtcatgt aactgcttta gaccattgag tcatgagtag aaatgatgag cataatacgt    48240
ggactgtgca ttcaaatgca agaacctcta tggatcacct tctcccttcc gcagagaccc    48300
acaaggctct gatggagtct gctccatcag cctggattcc tgagtgacag tgacatgcag    48360
aatccccaac acaccatgaa gatgcagctt aaaaagaaat aacattgttt taagcccctg    48420 ggaattttc acccatagca taagtttcct aatgctgata cgactaatta ccaaaacttg    48480
gtgtgttaca acaaaagaaa tgtatcatat tgtagttctg gaattcagaa gcccaaaatt    48540
gtgtgactgc gttacaatca agaagaaaag tcaagtatgt aaaggtgaag aataaaatgg    48600
tactgaccag ggtgaagtgc agggaggtaa tggtgagata caggtcaaaa aatacaaaat    48660
tgaagatagg tcagatgagg aagtccagag atcgaacatg ccatatatcg acaactagag    48720
ttaacaatat tgtattgaat ttagtatttt tgcttaaaga gtatatttca tgggctcttg    48780
acacacaccc acatgcagag taactgtgag atgatggata tgttcatttg cttgactata    48840
ataatcatta cactatgtat atgtatagga aagcatcatg tggtacacct tacatatata    48900 caatttttt aaaaaacagc tatgtttct ggagtctctg ttctttgcct ttactaattc    48960
tggaagctgg taacatttct tttctcatag ttacgtcttc ccatcactcc agcctctggc    49020
ttgcatcctc acatgtgctt ctctaactcc taatttcctg cctcctcctt cttataagga    49080
ctcatgtgat acactgtggg cccaccctga tgctagacca agatgttaaa accactgtct    49140
tcaacacgtt caaagagcta aaggaaacaa tagacaaaca actaaaataa ttcaggatta    49200
tgatacagta acaaaataag aactgtaaca aagagaaatt ataaaagaa atcaaacgag    49260 aactttagag ttgaaagtat tacaactaaa agttcattaa agaggttctc taacaagtga    49320
gcaggtggga aaaaatcaa gaaactggaa gatgaaatca ttgaaattat tgacagtgag    49380
gtatagatac aacaaaaatg aaagataata gaatctaagg gaatgatgat acattatcaa    49440
atcgataaaa atacacatta ctagagttct ggggaaaag agaaaaagag aaaggggcag    49500
aagattattg gaagaaatca tgaacaaaat cttcccaaac ttgataaaat acatgaatct    49560
acaagcttaa ggtgccaagg aaacccaaat ttaactcagc gataaagtca aagagaccca    49620
cattaagaca cattataatc caactgtcga caattaaagt caaggaaaga attctgaaag    49680
```

-continued

```
cagcaaaaga gaagcgattc ctctcacgcg agagatcctt gtaagattat cagctgagtt   49740
cttatcagaa gcattggagg ccacaagaca gaggaatgat atgtttaaaa tgctgaaaga   49800
ggaaaaacct atcaaccaag aactctacac ctggcaaaca tccttcaaac acaagggaga   49860
aattaagata ttctcagata aatcctcagc catggatcct tgcgtgaata gcacgatgtc   49920
tccaggccca aacttccctg atctgtagaa ggggtggcat caggtcatga aaatgagcac   49980
ccaccaccac acccaactgg tgtggtgaga gtttatgacc actaaacctt acctacaaaa   50040
acgctaaaag gagtgctttg ggtggaaatg aaaggatgct acatggcact caaaattgta   50100
tgaggaaata aagatgtcca gttaggtgta catttaaaaa attcatattt tcctgatgcc   50160
tcaacatccc tgaaacaagc tgtgagcacc ctaccaaatg accaggtaca gcagtgtgat   50220
aaagctggtc cctgccacaa ttcccctttt tgtcctcctc tgctgtgacc tagtagagta   50280
gtggcattaa aacataccag tgaatccatc atggtttttg tgtcctccac cctaactccc   50340
agtaagacac ttgcctgggg ttccaatctg tcttgcttcc ccatctgctt ggttgagcct   50400
gcttcacgga agctccttcc atatggcttc ctacctggca tgccataccc cactctctgg   50460
gaactatgag tagaataaat tgttcatctt catatgtctc tccaaatgaa attttcacag   50520
tcatgttaga gtgttcttta tagacccaat cagcaggact tactctacca tttttcaacac  50580 taatggcaat gagaatggga tcattctaaa ctagggtgga aagttcctag gagattccct   50640
ttgaatgctc atggcttgct aatttgctac tctgattggc tcaaccattt gggagatgct   50700
attaccctga tggctttctt gtactctgct ttcttcagct ttgtgttgcc ttttgggagt   50760
gttaccaaga ctctccatcc taaagtgggg atcatgtctc aatatcaata atggcatcca   50820
cctttcttca ggagcacaga gatgacatta cattgataac aacatcttta aaacagattc   50880
atttgacaca cgtattaatg tcatataatc caacaccttt aagtttctgt taaatgctag   50940
tggcaacata ttcttttaca catcatcgaa aacaatactc ttgttagtgc cttcaaacaa   51000
acggacaaac aaacaaaaat acctcttctc tataaaaatt ttgccaactt ctttcatgcc   51060
tgttggagtc tcttcaccac tcatgttggc catgaatttc cccagggctt ttgatgcaga   51120
aacaatgccc ctcttggcct catcctatat tccattaaaa caacaaatga ctggttacct   51180
actgggatcc cctggtctgg agtacagttc tacaaggcat actttcctgt tgcaatcatt   51240
aaccataaat tgtcccacat ccaggctttg ctcacctgat atgaagcgca ttggaaacta   51300
agcttccact agaacacaaa attaaaatca ctgccaggtc cagctgcaca ccattctgtt   51360
gacagttggc attattactg ctaggtttgt taatgcaaaa atactcaacc aaatactagc   51420
aaactgaatt gaatagcata gtagaaggat aatacaccat gagcagataa tagttattcc   51480
tgaaatccaa ggatgtttca gtaaacaaat gacaacaatg taatgtacca tatttatgga   51540
ataaagggaa aaacacatga ttatccattt gatgcagaaa agcctttgac aaatgtggct   51600
atctttctat gacaaaaata atcaataaaa ggaatatatg aaaacattca aaattataag   51660
tcatatactc atactttctt gttttttttgg cactatctaa tttactattc actgtctaat   51720
ttactatttt atttacctcc ttatcatggg tattggttac tgtcattctc cagtggatat   51780
aaggaacaaa agggaaacta ctttttctat tttattcacc agtgcaccca acatttctat   51840
gtcaggtcct ggaacatagt agatatccaa taaatatgtg tataatgtgt gaattgctca   51900
gtgggatact ttcttaagag actgaaatct tttattttaa atggattgtt tctgttgaat   51960
ttggagaaaa taaatttccc atgtagatga gttggtgaag aaaaaatcaa tttgcaatca   52020
tacagaaagc agaagagccc aggagaagaa aactacacat cctcttcctc ataccacacc   52080
```

-continued

```
cctgcacaca ctcatactag cagcagctgc agaaatctca tggaatagaa tcagggccag   52140
aagtatttgg gaagagtaat ggtgaaaact gtgatctcta gattaagagt gcctgagctc   52200
aaatcatagc tctgccaatt accaatgaat gaccttggaa tgctttgtgc ttctgtttcc   52260
ttatctatgt gtgtgtgtgg tgggggggcag ggggtgataa gaatctctac cttggatata   52320
atgatcatcc aaagtaagag ctgtaagatg tttccaacag tgtctgccac atggagggtg   52380
ttcaaaaatt ataaagttgg ccaggcacag tggctcaagc ctgtaatccc agtactttgg   52440
aaggctgagg tgggcagata cctgaggtca ggagtttcag accagcctgg ccaacatggc   52500
aaaaccctgt ctctactaaa aataaaaata aaaaaatagc tgagggtggt ggcacacccc   52560
tgtggtccca gctattcagg aggcagaaac atggcaatca cttgaaccca ggaagcagag   52620
gttgcagtga gctgagatcg caacactgca ctccagcctg ggtgacagag tgagaccttg   52680
actcaaaaaa atgaataaat aaataaaata aagtttttac tcagtagatt tcctgaagct   52740
tggaggcttc aatggacatt agatgatgag gatataggta tgactatgga tatggatata   52800
actaatataa ctatagatat agttactata tagatataga tgctataggc cgaagtttct   52860
gcaactttat ccacttcttt cttcctcaca cctacccttc atgaaagtgg gaacactaat   52920
agagtaatgc atggaagttc tattttgagg gactatgcat tttaccaaga ggtttgctta   52980
tctattgctt atcttaacag attggggggac tttgaggggt aagatcagag aagtaaaaaa   53040
gaagagagag tgtgggcaac agggaaaacc aaatatctct ttaatgtgca tttcatatag   53100
actaagaaat ggttagaagg aaataataag aaaagtcttt taaaaatcct gtgtgtgttt   53160
cgcatagtca agtgagattt atcccaggaa tgtaaggatg ggtcgatatt cagcaatctc   53220
tccatgtgac acactacata aacagaatga gtgacaaaaa ccctatgacc atctcaacac   53280 aggcccaaa aatgcatatg aaaaaattca acatttttaa gtgataaaaa ctgtcaatga   53340
attacatata ggatgattgt tcctcaacat aataaatgcc atatgggaca actccataaa   53400
aatgaactca catatttaca cttaattgat ctttgataaa agtttcaagg acacacaata   53460
gggaaaagtc aatctcttca aaaatgttat tgagtaaact ggatatccat gtatagagaa   53520
ataaaattgg aacttcatct cataccacat acaaaaatca actcaaaatg gattaaagac   53580
ttaaatgtaa gatctgaaac tgtaaagtac tagaagaaaa gttctgtaac attggtctag   53640
gcaatcagtt tctagatatc agcccaaaag cacacacaac agaagcaaaa atagacaaat   53700
tgaattacaa caaactaaaa agcttctaca tgtgcatttc tcgtggatat agaaatgaat   53760
gtgggattac atacatagcc aagaaaacaa tcaacagagt gaagagacaa catacagaat   53820
gggaaaatat atttgcaaat tatacatttg ataaggagtc aatacacaaa acatataaag   53880
aactcaagca actcaattat aaggcaacaa ctcactcaat taatatatgg gccaaagacc   53940
tgaatagaca tttctcaaaa gaagacatta aaatggccag caggcatata aaaaataccc   54000
aatcttacta ttcatcagag aaatgcaaat taaatccata gtgaggtatc atctcacacc   54060
tgttagaatg gttattatca aaatgaggaa atttaagtag cattggagag tatgtggaga   54120
aaagagaatc caacccactg ttggtgagaa tgtaaattag tacagccatt attgaaaaca   54180
gtatggagtt tcctccaaaa attaaaaata gaactatcat tagatccagc aatctcactt   54240
ctgggtgtat atccaaagga agtaacatca gcatgtcaca gcgatatctg cacccatatc   54300
cattgcagca ttatttacag tagcaaaaat ggaatcaacc taagtgtcta tcaacagatg   54360
aatggagaaa gaaaatgtgg tatatataca caatgaaatt ctaatcagcc ttacaaaaga   54420
```

-continued

```
aggaaattct gtcatttcca acctggagga tactatgcta agtgaaataa gccaggcaca   54480
gaaagacaaa taccacatgg tctcactcat acactgaatc taaaaaagtt gaactcacac   54540
aagtagagag tagagcctat aatcacagca ctttgagagg ctgaggcagg tggatcacct   54600
gaggtcagga gtttgagacc agcctggcca acatggtgaa accccgtcac tactaaaaat   54660
acaaaaaatt agccgggcat ggtggcggac atctgtaatc ccagctactc gggaggctga   54720
agcaggagaa tcacttgaac ccaggtggtg gaggctgcag tgagccgaga tctcaccatt   54780
gcactccagc ctggacaaca agggtgaaac accgtctcaa aaaaaaaaa gaagtagaga   54840 ctagagtggt ggttaccagg ggcaggggag ggggtgtagt tgggagatac tggtcaaagg   54900
atacaacatt ttagtttaga taagagaaat aagtttaaga gatgtattgt acgatatgat   54960
ttctagagtg aataacatga attgtattgt tgaaaattgc taagagagca gagttttataa  55020 gttctcacca caaaaagtga tatacatgta aggtaatgca taggttaatt agctcaaatt   55080
aatcatgtac acatatttta taatatgttg tacatgataa gtatatatgc ttttctcaaa   55140
caaaaataaa atacatttct tttctgagac atttcattgc aaataaaaag ataacaataa   55200
atgtgaaatc ttatgtacat gtatgtacac ttatagtcac ttatacacac atatatatat   55260
gtatacatat atacacatgc attcacaaat atatataaaa gtttgttctg tccttatact   55320
atataaagat gttttgtgca ttaaataaaa ttatgaaacc tgttaaaatc tcagtaaaat   55380
atttggcaca taaaagtcat ccaacacatt tgtaacaaat gttgggagta tatacaccag   55440
cgttttaact ctgagtgtca cttctctgac tggtgtgatg ggtgatgatt attcctatgt   55500
ttacttccct gcatgtgcta atatttctac aagtagcata acatggctaa aagaatgaac   55560
tctggagttg gtccacctgg acttgaatcc cagctgctcc actgactgag gtaggggaca   55620
atggacaagc tcctccctct gcctgactcc ttgtttttcaa ataggagtta ataggtgtag   55680
ctttcaaata gggatgttgt gaggattagt agagttaagt agagttaaaa tacacaaatt   55740
actaagaact gtgtctacct tgtaggaaga gctcaattgc tgaactctta ccactgtcat   55800
ttgggtaaag tgtatatgta agaaagataa tttgaaaagt gagaaccttg tcctctagga   55860
cctgtgaggt gactcacagc aggggccagt ggggagcagg gaggctgctg tgcccagccc   55920
tgtgattctg gggtcagctc cctggcctga gtagggtgtg aggacaggca gcctgtctgt   55980
gggctgtgag cagggctctc ccaggctgca ccaggaaagg tcttccaatc ctgcctgtcc   56040
tggggaaggg aaaataaatt ctccatggta aagtcgaaag aaccaaggta gattgtggta   56100
cttgttatgg gctgaatgtg tcccccaaaa tgcatgtgtt gaagccccag tccccagaac   56160
ctcagaattt gactgtattt ggagacaggg tctttaagaa gctatttagt tacatgaggt   56220 cattggggggg gtcttaatct aatatgactg gcgatctcag aagaagagga gatgaggaca   56280
cagacacaca ctgagggaag aacacgtaat aagacacaga gcagagacgg ccatctacga   56340
gccagtaaga aagacctcag tacagactaa ccctgccaac accttgatct tgcattcagc   56400
ctccaaaagt gcaggaagt aaatgtctgt aattttagct gcccagtctg tagtactttg    56460
ttatgcaagc cctaggaaag gattacaggg cccagaaagc agcaaattcc ttcttaaaga   56520
ggaagagggc acaaaaaaat gggtggtaac actgagatta cagaggagtg ggaagcaggg   56580
ggaacagagg gcaaagtatg cagcatcctg aagaaggaca gtggctgaac atccccggga   56640
aacattgctc ccctgcccaa ctcaggcact gtttcagact tcacatcctc agggtgctga   56700
acagagggct gagcctggag ccacacaccc tgtcaggctg tctctcagct cactctgtgg   56760
ccttgggcag atggtttttgc ctcctggagc ctcaaggctc cagcctcaag gctcctgctc   56820
```

-continued

```
ctcagtttgg ggcagcagaa gggttcccaa aacctactgc tcaatatttg acaggaacca   56880
ggtctgcttc tggtaaggat ttaaataatg attcttctgt gtttgtcaaa tgaaatatta   56940
tttttaaaat gtaactaatt atggtgctgg ttgaaggatc acctgattcc atcccttggt   57000
agccagctgc agatccacag agaaagtgct cagctccctg atcttctgct ctcagacaat   57060
gcccagtcct tgacctacct tgggagcact tgtgtttgtc tggaatccct gaaagcccag   57120
gggcagggat ttcagggctg caagcagaga gaaagggttc tagcccaagg cagtgctcac   57180
ctgtgcatcc ccgcagcaga atcagcagca ggaaaggacc aggagggtgg ggccaggagg   57240
ctgggatggg tatcctgaag acctcaggag cctgctccgt ccaaatatct gtgctgggga   57300
gatgtcaaac ttctctgagg agagaagaca agcactgtct cccttgattc aagaggaagt   57360
ggcaa                                                                57365
```